US010323057B2

(12) United States Patent
Burke et al.

(10) Patent No.: US 10,323,057 B2
(45) Date of Patent: Jun. 18, 2019

(54) AMPHOTERICIN B DERIVATIVES WITH IMPROVED THERAPEUTIC INDEX

(71) Applicant: The Board of Trustees of the University of Illinois, Urbana, IL (US)

(72) Inventors: Martin D. Burke, Champaign, IL (US); Stephen Davis, Westfield, IN (US); Brice E. Uno, Champaign, IL (US); Justin Struble, Ballwin, MO (US); Ian Dailey, Maplewood, MN (US); Kaitlyn C. Gray, Freeland, MI (US); David M. Knapp, Washington, DC (US); Pulin Wang, Austin, TX (US); Nagarjuna Palyam, Florence, KY (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 330 days.

(21) Appl. No.: 15/026,520

(22) PCT Filed: Oct. 6, 2014

(86) PCT No.: PCT/US2014/059334
§ 371 (c)(1),
(2) Date: Mar. 31, 2016

(87) PCT Pub. No.: WO2015/054148
PCT Pub. Date: Apr. 16, 2015

(65) Prior Publication Data
US 2016/0215012 A1 Jul. 28, 2016

Related U.S. Application Data

(60) Provisional application No. 62/045,956, filed on Sep. 4, 2014, provisional application No. 61/887,729, filed on Oct. 7, 2013.

(51) Int. Cl.
*A01N 43/90* (2006.01)
*C07H 17/08* (2006.01)
(52) U.S. Cl.
CPC .......... *C07H 17/08* (2013.01); *A01N 43/90* (2013.01)
(58) Field of Classification Search
None
See application file for complete search history.

(56) References Cited

U.S. PATENT DOCUMENTS

| | | | |
|---|---|---|---|
| 5,204,330 | A | 4/1993 | Driver et al. |
| 2007/0238746 | A1 | 10/2007 | Brandl et al. |
| 2009/0221520 | A1 | 9/2009 | Malpartida Romero et al. |
| 2012/0015896 | A1 | 1/2012 | Miyake et al. |
| 2014/0256663 | A1 | 9/2014 | Antillon Diaz et al. |

FOREIGN PATENT DOCUMENTS

| | | |
|---|---|---|
| WO | WO-1993/016090 A1 | 8/1993 |
| WO | WO-2009/004322 A2 | 1/2009 |
| WO | WO 2014/165676 A1 | 10/2014 |

OTHER PUBLICATIONS

Ichikawa, Y. et al., "Urea glycoside synthesis in water", *Syn. Lett.*, 6:1019-1022 (2004).
Volmer, A. A. et al., "Synthesis and biological evaluation of amphotericin B derivatives", *Natural Product Reports*, 27:1329-1349 (The Royal Society of Chemistry, 2010).
Wilcock, B. C. et al., "C2'—OH of amphotericin B plays an important role in binding the primary sterol of human cells but not yeast cells", *JACS*, 135:8488-8491 (USA, May 29, 2013).
International Search Report and Written Opinion from parent PCT application PCT/US2014/059334 dated Jan. 6, 2015.
Byrne et al., "Biosynthesis of deoxyamphotericines and deoxyamphoteronolides by engineered strains of Streptomyces nodosus," Chem Biol Curr Biol, 10(12): 1215-1224 (2003).
Davis et al., "C3—OH of amphotericin B plays an important role in ion conductance," J Am Chem Soc, 137(48): 15102-15104 (2015).
Davis et al., "Nontoxic antimicrobials that evade drug resistance," Nat Chem Biol, 11(7): 481-487 (2015).
Geiser, "Antifungal design: the toxicity-resistance yin-yang," Nat Chem Biol, 11(7): 453-454 (2015).
Supplementary European Search Report for European Application No. EP 14853012.4 dated Feb. 9, 2017.
Tevyashova et al., "Structure-antifungal activity relationships of polyene antibiotics of the amphotericin B group," Antimicrob Agents Ch, 57(8): 3815-3822 (2013).
International Search Report and Written Opinion from PCT application PCT/US2015/049647 dated Mar. 14, 2017.
Brautaset et al., "New nystatin-related antifungal polyene macrolides with altered polyol region generated via biosynthetic engineering of Streptomyces noursei," Appl Environ Microbiol, 77(18):6636-6643 (2011).
Matsumori et al., "Mycosamine orientation of amphotericin B controlling interaction with ergosterol: sterol-dependent activity of conformation-restricted derivatives with an amino-carbonyl bridge," J Am Chem Soc, 127(30):10667-10675 (2005).
Zhen et al., "Structural modifications of an antifungal agent: Amphotericin B," Chinese Journal of Antibiotics, 35(8):571-575 (2010).

*Primary Examiner* — Shaojia A Jiang
*Assistant Examiner* — Bahar Craigo
(74) *Attorney, Agent, or Firm* — Dana M. Gordon; Foley Hoag LLP

(57) ABSTRACT

Provided are certain derivatives of amphotericin B (AmB) characterized by reduced toxicity and retained anti-fungal activity. Certain of the derivatives are C16 urea derivatives of AmB. Certain of the derivatives are C3, C5, C8, C9, C11, C13, or C15 deoxy derivatives of AmB. Certain of the derivatives include C3' or C4' modifications of the mycosamine appendage of AmB. Also provided are methods of making AmB derivatives of the invention, pharmaceutical compositions comprising AmB derivatives of the invention, and methods of use of AmB derivatives of the invention.

9 Claims, 33 Drawing Sheets

| Compound | R | R' |
|---|---|---|
| amphotericin B (AmB) | COOH | sugar with Me, OH, OH, NH₂ |
| amphotericin B methyl ester (AmBME) | COOMe | sugar with Me, OH, OH, NH₂ |
| amphoternolide (AmdeB) | COOH | H |
| C2'deoxy amphotericin B (C2'deOAmB) | COOH | sugar with Me, OH, NH₂ at 2' |

*total synthesis via iterative cross-coupling*

Scheme 3

Scheme 5

Scheme 6

Scheme 7

Scheme 9

Scheme 10

Scheme 11

Scheme 12

Scheme 15

Scheme 17

Scheme 18

Scheme 20

Scheme 21

Scheme 23

Scheme 24

Scheme 25

Scheme 26

Scheme 27

AMPHOTERICIN B DERIVATIVES WITH IMPROVED THERAPEUTIC INDEX

RELATED APPLICATIONS

This application is the U.S. national phase of International Patent Application No. PCT/US2014/059334, filed Oct. 6, 2014, which claims benefit of U.S. Provisional Patent Application No. 61/887,729, filed Oct. 7, 2013, and U.S. Provisional Patent Application No. 62/045,956, filed Sep. 4, 2014.

BACKGROUND OF THE INVENTION

For more than half a century amphotericin B (AmB) has served as the gold standard for treating systemic fungal infections. AmB has a broad spectrum of activity, is fungicidal, and is effective even against fungal strains that are resistant to multiple other agents.[1] Surprisingly, clinically significant microbial resistance has remained exceptionally rare[2] while resistance to next generation antifungals has appeared within just a few years of their clinical introduction.[2e, 3] Unfortunately, AmB is also highly toxic.[4] Thus, the effective treatment of systemic fungal infections is all too often precluded, not by a lack of efficacy, but by dose-limiting side effects.[5] Some progress has been made using liposome delivery systems,[6] but these treatments are prohibitively expensive[7] and significant toxicities remain.[8] Thus, a less toxic, but equally effective AmB derivative stands to have a major impact on human health.

SUMMARY OF THE INVENTION

An aspect of the invention is AmBMU or a pharmaceutically acceptable salt thereof

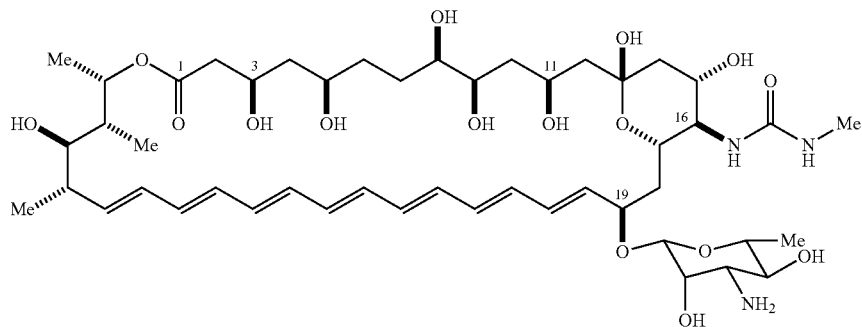

AmBMU

An aspect of the invention is AmBAU or a pharmaceutically acceptable salt thereof

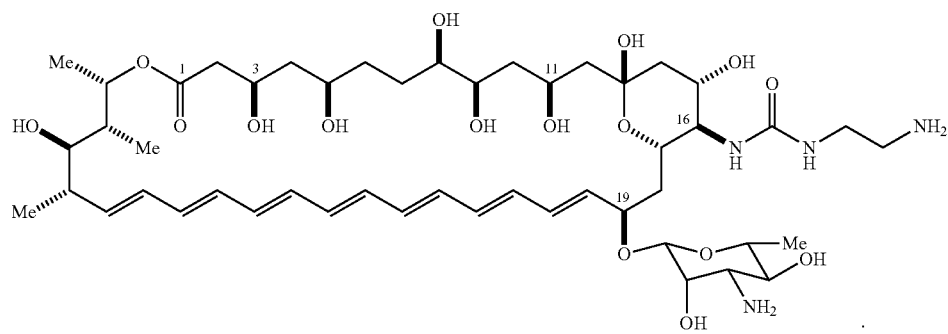

AmBAU

An aspect of the invention is AmBCU or a pharmaceutically acceptable salt thereof

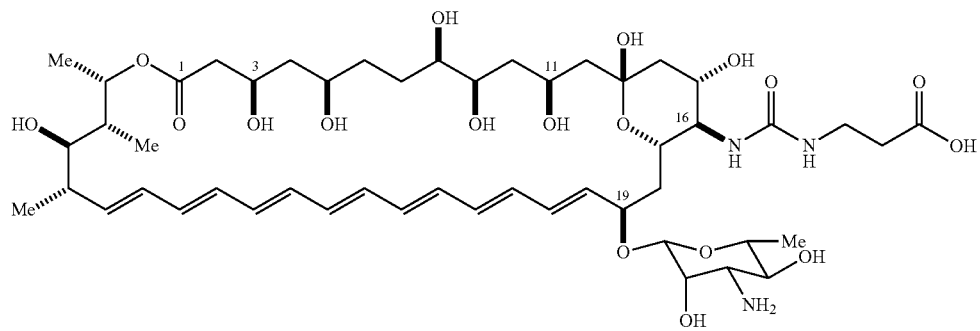

AmBCU

An aspect of the invention is C3deOAmB or a pharmaceutically acceptable salt thereof

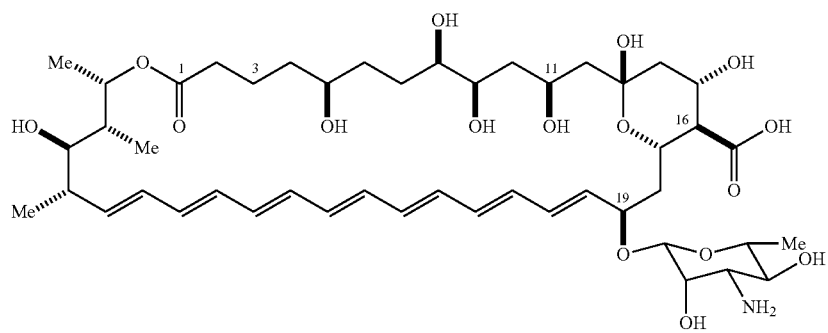

C3deOAmB

An aspect of the invention is C9deOAmB or a pharmaceutically acceptable salt thereof

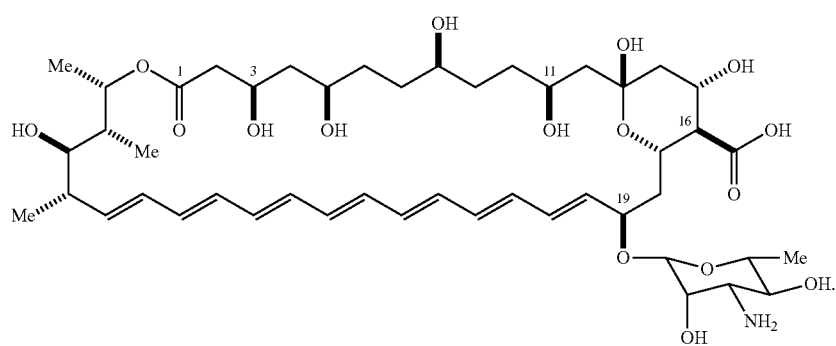

C9deOAmB

An aspect of the invention is C5deOAmB or a pharmaceutically acceptable salt thereof

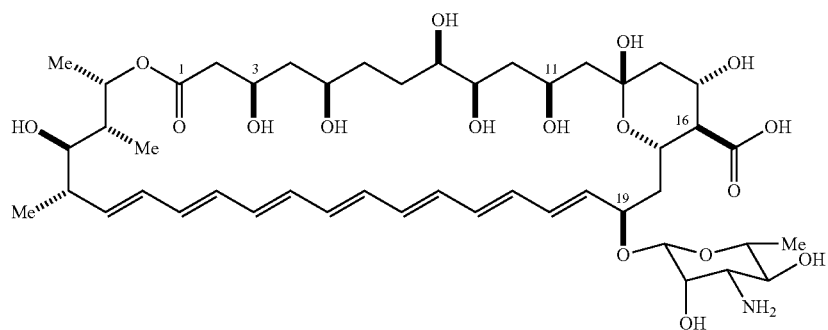
C5deOAmB
An aspect of the invention is C8deOAmB or a pharmaceutically acceptable salt thereof
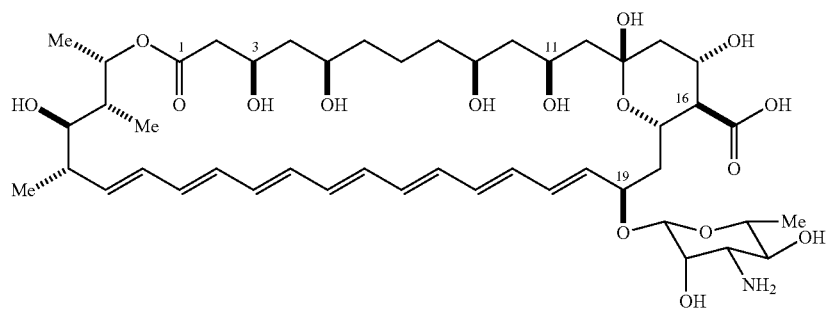
C8deOAmB
An aspect of the invention is C11deOAmB or a pharmaceutically acceptable salt thereof
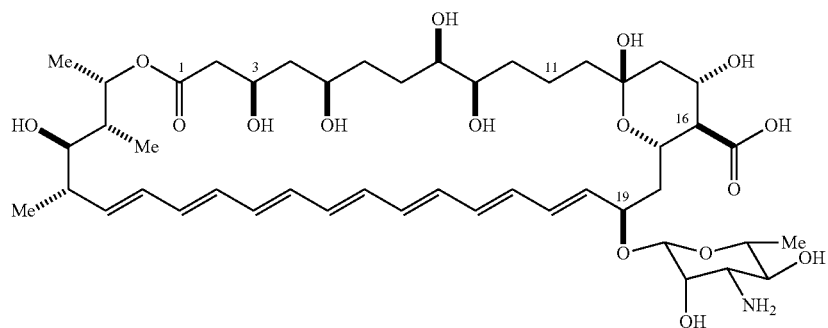
C11deOAmB
An aspect of the invention is C13deOAmB or a pharmaceutically acceptable salt

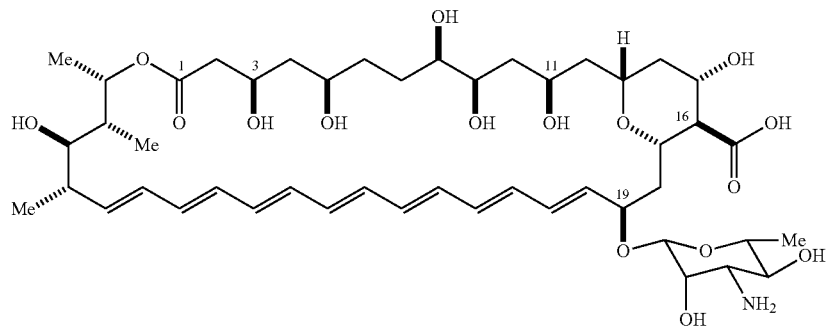
C13deOAmB
An aspect of the invention is C15deOAmB or a pharmaceutically acceptable salt thereof
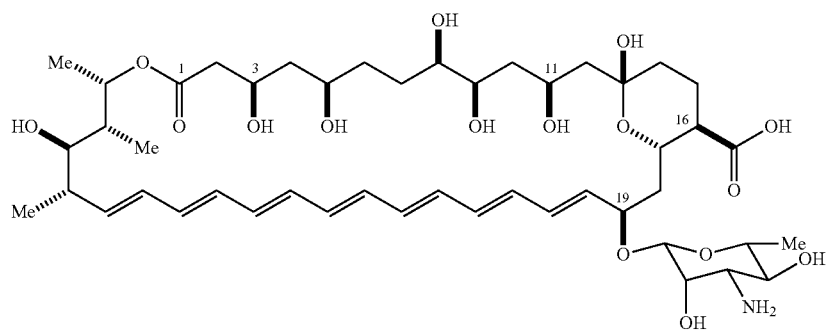
C15deOAmB
An aspect of the invention is C3'deNH$_2$AmB (C3'deamino AmB; C3'deAAmB) or a pharmaceutically acceptable salt thereof
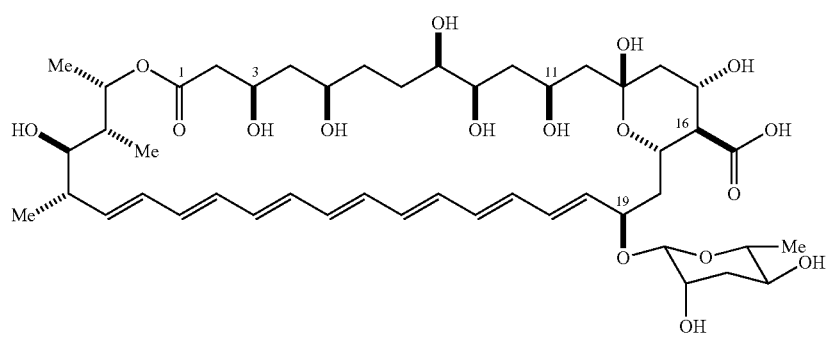
C3'deNH$_2$AmB
An aspect of the invention is C4'deOAmB or a pharmaceutically acceptable salt

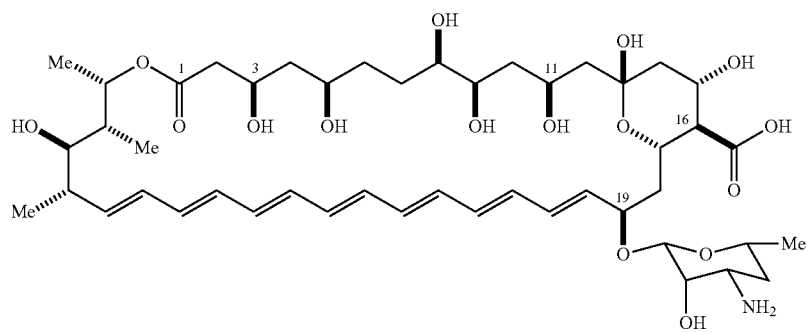
C4'deOAmB
An aspect of the invention is Compound X
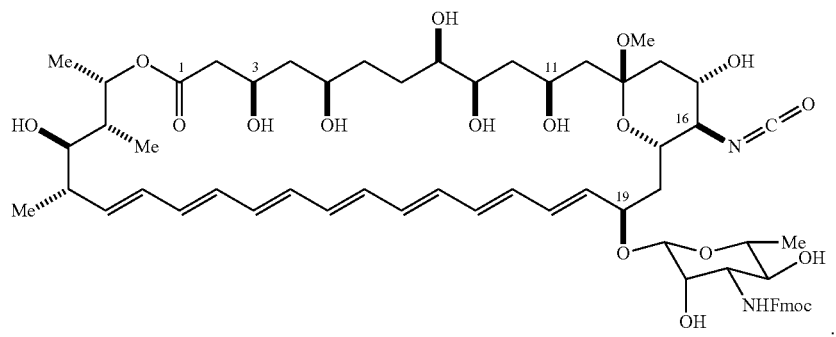
X
An aspect of the invention is Compound 1
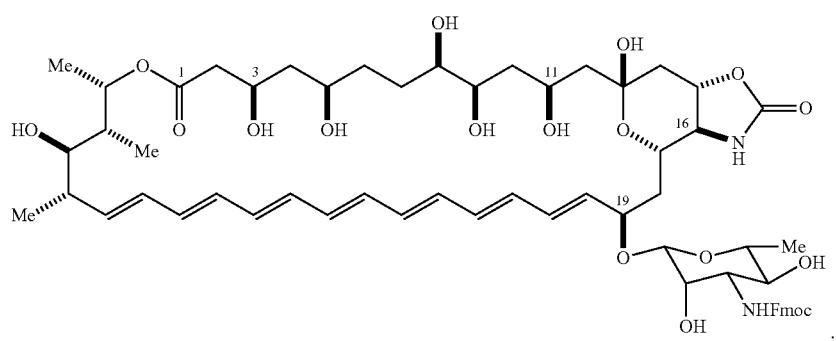
1
An aspect of the invention is a method of making compound 1 as disclosed in the specification and drawings.
An aspect of the invention is a method of making a C16 urea derivative of amphotericin B according to any one of the six transformations shown in Scheme 2:

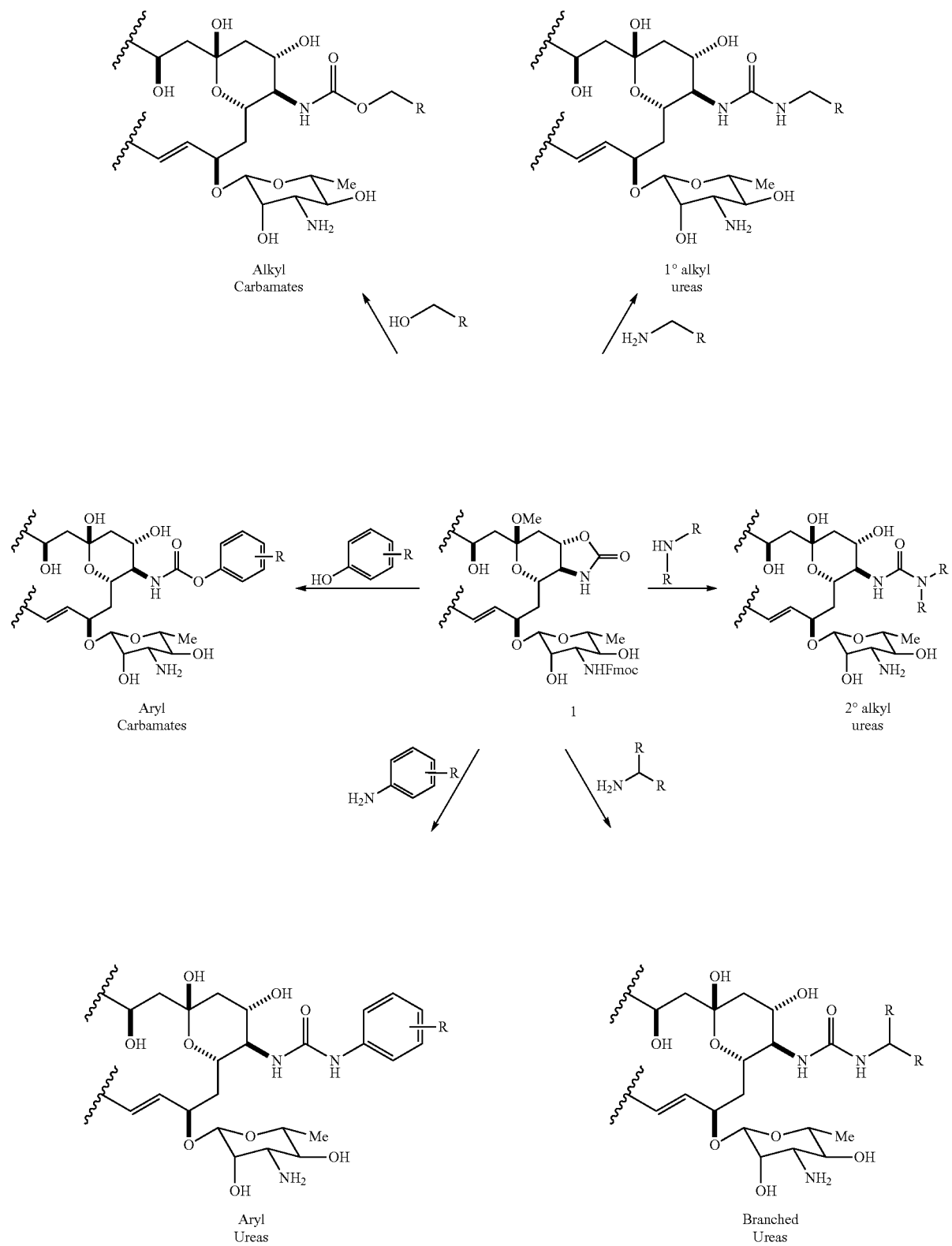

wherein 1 represents

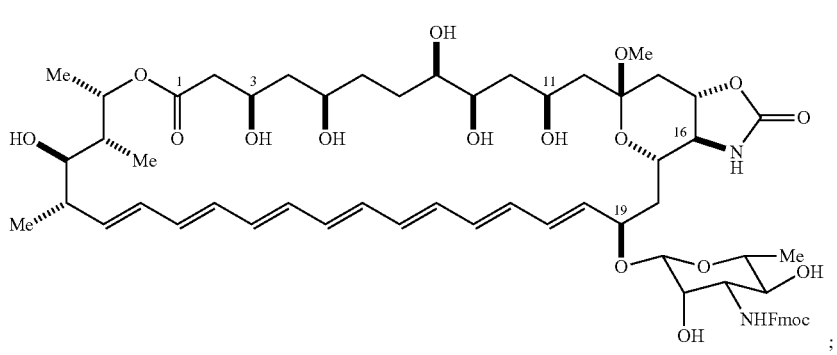

and each R is independently selected from the group consisting of hydrogen, halogen, straight- or branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

An aspect of the invention is a method of making AmBMU as disclosed in the specification and drawings.

An aspect of the invention is a method of making AmBAU as disclosed in the specification and drawings.

An aspect of the invention is a method of making AmBCU as disclosed in the specification and drawings.

An aspect of the invention is a method of making C3deOAmB as disclosed in the specification and drawings.

An aspect of the invention is a method of making C9deOAmB as disclosed in the specification and drawings.

An aspect of the invention is a method of making C5deOAmB as disclosed in the specification and drawings.

An aspect of the invention is a method of making C8deOAmB as disclosed in the specification and drawings.

An aspect of the invention is a method of making C11deOAmB as disclosed in the specification and drawings.

An aspect of the invention is a method of making C13deOAmB as disclosed in the specification and drawings.

An aspect of the invention is a method of making C15deOAmB as disclosed in the specification and drawings.

An aspect of the invention is a method of making C3'deNH$_2$AmB as disclosed in the specification and drawings.

An aspect of the invention is a method of making C4'deOAmB as disclosed in the specification and drawings.

An aspect of the invention is a method of inhibiting growth of a fungus, comprising contacting a fungus with an effective amount of a compound selected from the group consisting of AmBMU, AmBAU, AmBCU, C3deOAmB, C5deOAmB, C8deOAmB, C9deOAmB, C11deOAmB, C13deOAmB, C15deOAmB, C3'deNH$_2$AmB, and C4'deOAmB, and pharmaceutically acceptable salts thereof.

An aspect of the invention is a method of treating a fungal infection in a subject, comprising administering to a subject in need thereof a therapeutically effective amount of a compound selected from the group consisting of AmBMU, AmBAU, AmBCU, C3deOAmB, C5deOAmB, C8deOAmB, C9deOAmB, C11deOAmB, C13deOAmB, C15deOAmB, C3'deNH$_2$AmB, and C4'deOAmB, and pharmaceutically acceptable salts thereof.

In one embodiment, the compound is administered orally or intravenously.

In one embodiment, the compound is administered orally.

In one embodiment, the compound is administered intravenously.

An aspect of the invention is a pharmaceutical composition, comprising a compound of selected from the group consisting of AmBMU, AmBAU, AmBCU, C3deOAmB, C5deOAmB, C8deOAmB, C9deOAmB, C11deOAmB, C13deOAmB, C15deOAmB, C3'deNH$_2$AmB, and C4'deOAmB, and pharmaceutically acceptable salts thereof; and a pharmaceutically acceptable carrier.

In one embodiment, the pharmaceutical composition is an oral or intravenous dosage form.

In one embodiment, the pharmaceutical composition is an oral dosage form.

In one embodiment, the pharmaceutical composition is an intravenous dosage form.

BRIEF DESCRIPTION OF THE DRAWINGS

FIG. 4A depicts a scheme for stereoselective hydroboration of BB1 to install the C11 stereocenter.

FIG. 4B depicts a scheme for hydroboration of C9-deoxy BB1 resulting in a mixture of diastereomers at C11.

FIG. 39A, 1 mg/kg AmB, AmBMU, or AmBAU. FIG. 39B, 4 mg/kg AmB, AmBMU, or AmBAU. FIG. 39C, 16 mg/kg AmB, AmBMU, or AmBAU.

DETAILED DESCRIPTION

Figure 1:
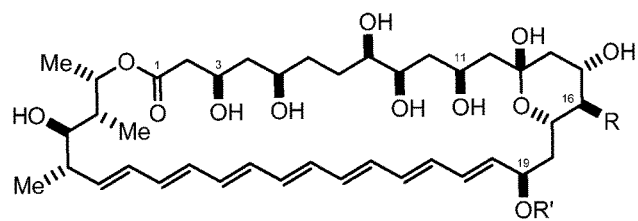
FIG. 1 depicts structural formulas of AmB and certain derivatives thereof.

A lack of understanding of the mechanism(s) by which AmB is toxic to yeast and human cells has thus far hindered the rational development of a clinically successful derivative. The longstanding accepted mechanism of action of AmB has been ion channel formation within a cell's membrane leading to electrochemical gradient disruption and eventually cell death.[2d, 9] This model suggests that development of a less toxic derivative requires selective ion channel formation in yeast versus human cells.[10] Contrary to this longstanding model, our group recently discovered that the primary mechanism of action of AmB is not ion channel formation, but simple ergosterol binding.[11] Gray, K C et al., *Proc Natl Acad Sci USA* 109:2234 (2012). Yeast and human cells possess different sterols, ergosterol and cholesterol, respectively. Therefore, the new model suggests a simpler and more actionable roadmap to an improved therapeutic index; i.e., a less toxic AmB derivative would retain potent ergosterol binding capability, but lack the ability to bind cholesterol. Recently our group reported that removal of the C2' hydroxyl group from the mycosamine sugar produced a derivative, C2'deOAmB (FIG. 1), which surprisingly retains ergosterol-binding ability, but shows no binding to cholesterol. Wilcock, B C et al., *J Am Chem Soc* 135:8488 (2013). Consistent with the preferential sterol binding hypothesis, in vitro studies demonstrated that C2'deOAmB is toxic to yeast, but not human cells.

To explain why removal of the C2' alcohol results in loss of cholesterol binding ability, while maintaining efficient ergosterol binding, we hypothesized that the AmB structure exists in a ground state conformation capable of binding both sterols. Removal of the C2' alcohol potentially results in a conformational change of the AmB structure which retains ergosterol binding ability but is incapable of binding cholesterol. A generic molecule is capable of binding two different ligands in a common binding site. Modification at a site distal to the binding pocket alters the binding site conformation. This principle of allosteric modification causes preferential binding of one ligand over the other. To our knowledge, such ligand-selective allosteric effects have not been previously observed in small molecule-small molecule interactions. Encouragingly, ligand selective allosteric modifications have been observed in proteins which bind multiple ligands in a common binding site.[13] We thus hypothesized that removal of the C2' alcohol allosterically modifies the sterol binding pocket, accounting for the decrease in cholesterol binding ability.

Interestingly, we noticed in a previously obtained X-ray crystal structure of N-iodoacyl AmB a prominent water bridged hydrogen bond joining the C2' alcohol to the C13 hemiketal.[14] We recognized that if such a water bridged hydrogen bond helped rigidify the ground state conformation of AmB, it would follow that removal of the C2' alcohol abolishes this interaction and thereby potentially enables adoption of an alternative ground state conformers having altered affinities for cholesterol and ergosterol. Intrigued by this capacity of the crystal structure to potentially rationalize our observations with C2'deOAmB, we hypothesized that this crystal structure may represent the ground state conformation of AmB which is capable of binding both ergosterol and cholesterol. Following this logic, we proposed that disruption or removal of any other rigidifying features observed in the crystal structure might similarly allow access to alternative ground state conformations and thereby alter the AmB sterol binding profile. Guided by this logic, careful inspection of the X-ray crystal structure revealed three additional intramolecular rigidifying features with the potential of stabilizing the AmB ground state: 1) a salt bridge between the C41 carboxylate and C3' ammonium, 2) a 1,3,5 hydrogen bonding network between C1 carbonyl O, C3 and C5 alcohols, and 3) a 1,3,5 hydrogen bonding network between the C9, C11, and C13 alcohols. We thus set out to systematically interrogate the consequences of perturbing each of these intramolecular stabilizing features to test the validity of the allosteric modification model as a new way to rationally access AmB derivatives with an improved therapeutic index.

New Allosteric Site #1: C41-C3' Carboxylate

The salt bridge interaction is the energetically strongest of the proposed rigidifying features. Thus, systematic modification of the group appended to the C16 carbon was targeted as the first series of derivatives to further probe this allosteric modification model. Multiple AmB derivatives modifying the C41 carboxylate have been reported including esters and amides among others.[10c, 10e, 15] However, all previous AmB derivatives maintain a carbon atom appended to the C16 carbon. We hypothesized that appending a heteroatom to the C16 carbon would have a great impact on the salt bridge interaction. Therefore, we sought an efficient, chemoselective synthetic strategy to gain access to such a derivative. Complicating such a goal, AmB possesses a dense array of complex and sensitive functional groups, making the direct synthesis of derivatives difficult.

In accordance with the invention, we discovered that a short three-step sequence of Fmoc protection, methyl ketal formation, and Curtius rearrangement, promoted by diphenyl phosphoryl azide, provides an intermediate isocyanate which is trapped intramolecularly to generate oxazolidinone 1 (Scheme 1).[16]

Scheme 1: Synthesis of C16 AmB derivatives

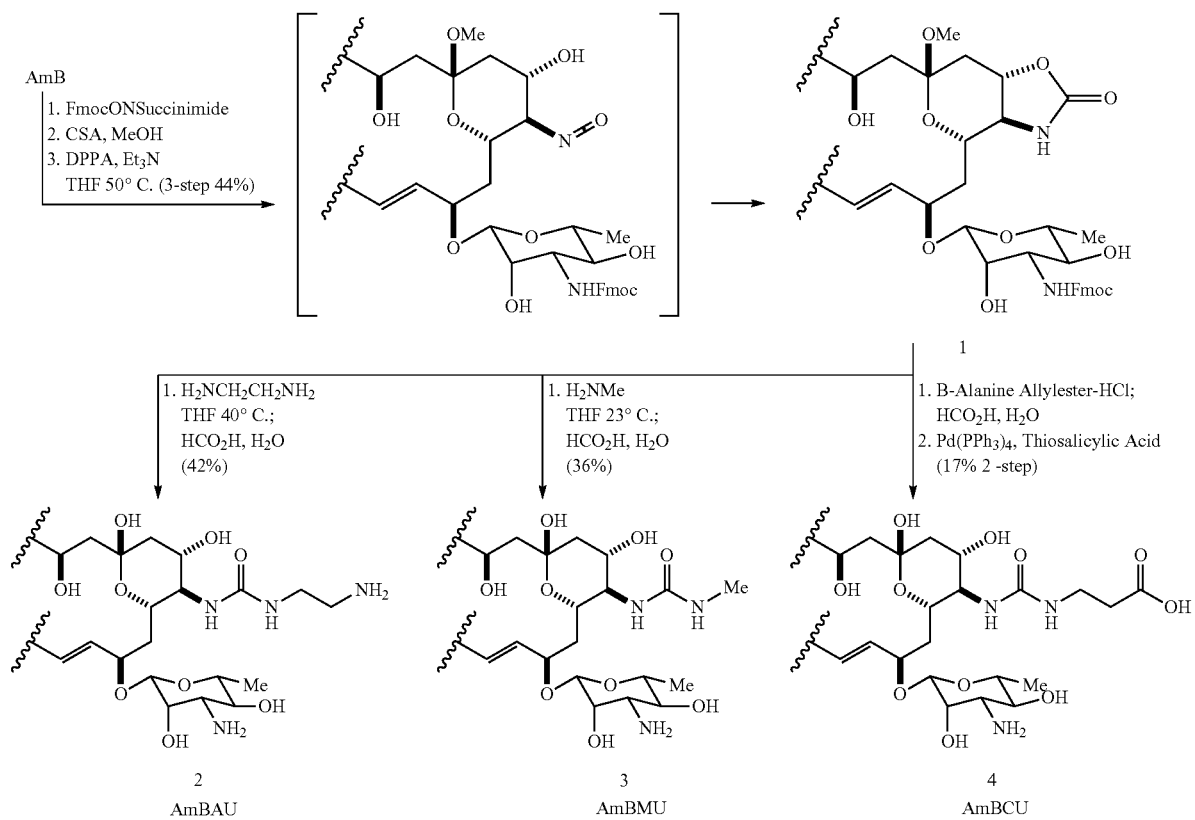

This facile sequence quickly generates gram quantities of versatile intermediate 1 in a chemoselective manner from AmB. Interception of 1 with a variety of amine nucleophiles efficiently opens the oxazolidinone while concomitantly cleaving the Fmoc protecting group. For example, exposure of 1 to ethylene diamine, followed by methyl ketal hydrolysis in acidic water generates aminoethylurea (AmBAU) 2 in 42% yield.[17] Similarly, utilizing methylamine accesses methyl urea (AmBMU) 3 in 36% yield from 1. Exposure of 1 to β-alanine allylester followed by allyl removal with Pd(PPh$_3$)$_4$ and thiosalicylic acid yields ethylcarboxylateurea (AmBCU) 4. This versatile synthetic strategy allows efficient access to a diverse array of AmB urea derivatives and is capable of generating large quantities of urea derivatives due to its synthetic efficiency.

With efficient access to this novel AmB chemotype, ureas 2-4 were compared to AmB and a range of previously reported AmB derivatives in an in vitro antifungal and human cell toxicity screen. Yeast toxicity was measured with broth microdilution assays (MIC) against Saccharomyces

*cerevisiae*. Human cell toxicity was studied by determining the amount of compound required to cause 90% hemolysis of human erythrocytes ($EH_{90}$). These results are summarized in Table 1. Amphotericin B inhibits *S. cerevisiae* growth at 0.5 µM while 90% red blood cell lysis occurs at only 10.4 µM. Removal of mycosamine (AmdeB) completely abolishes cell-killing activity in both yeast and human cell assays.[15e, 18] Methyl esterification (AmBME) retains antifungal activity at 0.25 µM against *S. cerevisiae*, while decreasing hemolysis concentration to one third that seen with AmB. C41MethylAmB shows, similar to AmBME, an MIC of 0.5 µM while causing hemolysis at 22.0 µM.[15e, 18] As previously observed, simple amidation to form amino amide AmB derivative AmBAA or methyl amide AmBMA increased potency against yeast to 0.03 µM and 0.25 µM respectively. Hemolysis activity remained similar to AmBME and C41MeAmB. Bis-amino alkylated amide derivative $AmBNR_2$ was previously shown to moderately improve the therapeutic index.[19] Consistent with precedent, $AmBNR_2$ shows increased antifungal activity compared to AmB, while requiring elevated concentrations to cause hemolysis at 48.5 µM.

TABLE 1

In vitro biological activity of AmB derivatives

| Name | Compound | MIC (µM) *S. cerevislae* | EH90 (µM) red blood cells |
|---|---|---|---|
| AmB | [structure] | 0.5 | 10.37 ± 1.17 |
| AmdeB | [structure] | >500 | >500 |
| AmBME | [structure] | 0.25 | 30.67 ± 5.38 |
| C41MeAmB | [structure] | 0.5 | 22.03 ± 6.26 |

TABLE 1-continued
In vitro biological activity of AmB derivatives
| Name | Compound | MIC (μM) S. cerevislae | EH90 (μM) red blood cells |
|---|---|---|---|
| AmBAA | 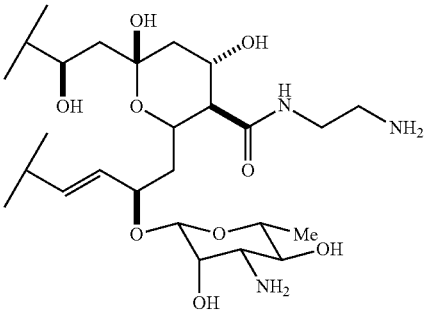 [SMILES: CC(C)/C=C/[C@@H](CC1O[C@](O)(C[C@@H](O)C(C)C)C[C@H](O)[C@H]1C(=O)NCCN)OC1OC(C)C(O)C(N)C1O] | 0.03 | 33.96 ± 8.85 |
| AmBMA | 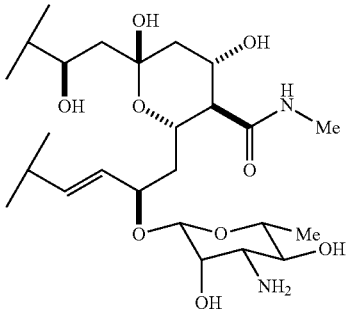 | 0.25 | 15.32 ± 3.39 |
| AmBNR$_2$ | 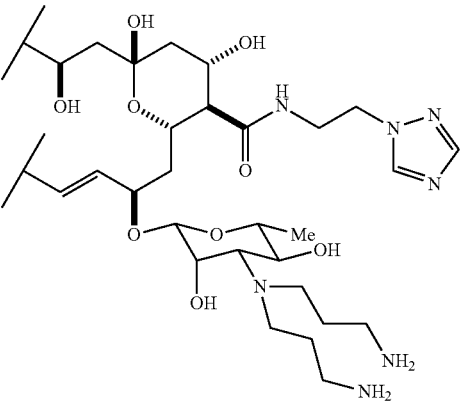 | 0.25 | 48.5 ± 8.7 |
| AmBMU | 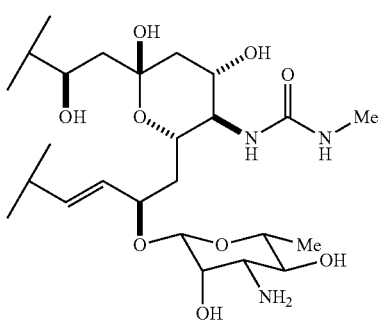 | 0.25 | >500 |

TABLE 1-continued

In vitro biological activity of AmB derivatives

| Name | Compound | MIC (µM) S. cerevislae | EH90 (µM) red blood cells |
|---|---|---|---|
| AmBAU | 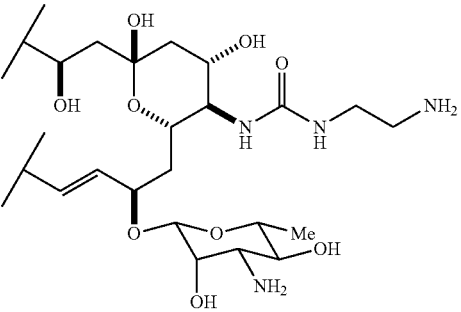 | 0.125 | >500 |
| AmBCU | 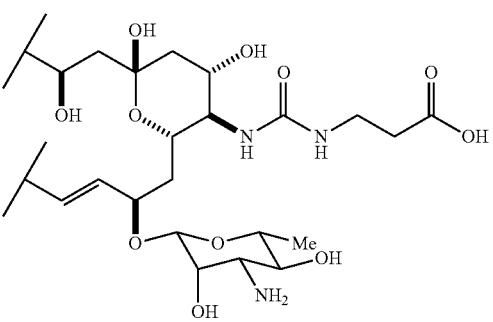 | 3 | 323.8 ± 30.2 |

Urea derivatives 2-4 maintain potent antifungal activity ranging from 0.125 µM to 3 µM against *S. cerevisiae*. Surprisingly, 2-4 possessed drastically decreased toxicity towards red blood cells. AmBMU and AmBAU did not reach an $EH_{90}$ even at 500 µM, greater than 45× that observed with AmB. AmBCU required 324 µM to cause 90% hemolysis in red blood cells, more than 30× required by AmB. Encouraged by this initial therapeutic index screen the urea series was further tested against the clinically relevant fungal cell line *Candida albicans*. *C. albicans* is the most common human fungal infection. AmB inhibits yeast grown of *C. albicans* at 0.25 µM. Similar to the trend seen with *S. cerevisiae*, the potency of urea derivatives 3-5 increased with increasing amount of cationic character. AmBAU, AmBMU, and AmBCU require 0.25, 0.5, and 1 µM respectively (Table 2).

TABLE 2

In vitro antifungal activity of AmB urea derivatives against *C. albicans*

| Compound | AmB | AmBMU | AmBAU | AmBCU |
|---|---|---|---|---|
| MIC (µM) | 0.25 | 0.5 | 0.25 | 1 |

Following the allosteric modification model, ureas 2-4 are hypothesized to maintain potent ergosterol binding ability, yet have lost the ability to bind cholesterol. To test this hypothesis a solid-state NMR assay is currently underway to determine binding constants of AmBMU, as a representative of the novel urea class, to both ergosterol and cholesterol.

Figure 2:
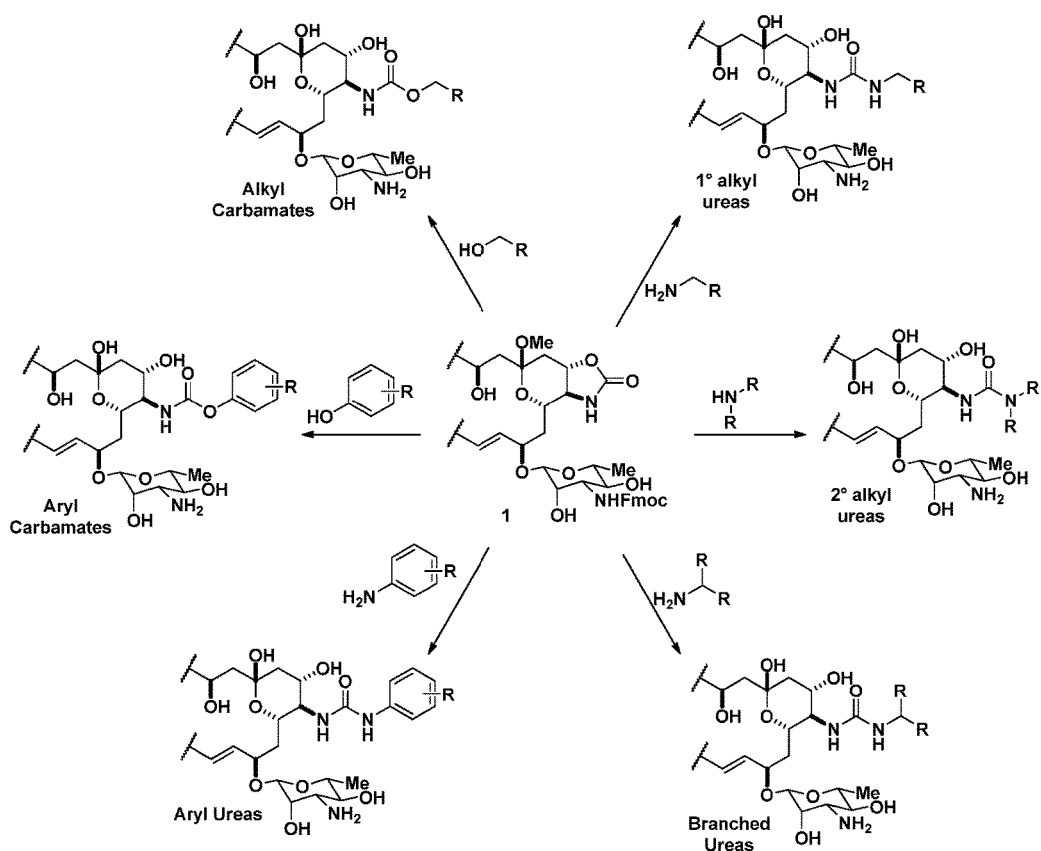
FIG. 2 depicts a number of synthetic schemes for preparing C16 amino AmB derivatives by reacting urea 1 with any of a wide range of heteroatom nucleophiles.

The strategy presented above can be used to access a wide variety of AmB derivatives with an amine appended to the C16 position. The opening of oxazolidinone 1 with a variety of nucleophiles (e.g., amines, alcohols, and phenols) could efficiently access a wide range of urea or carbamate derivatives. A small subset of the possible accessible derivatives is outlined in Scheme 2 (FIG. 2). Oxazolidinone 1 could be intercepted with primary amines to generate primary ureas, secondary amines to generate secondary ureas, and primary amines with alpha branching to create ureas with stereochemistry introduced at the alpha position. Additionally, oxazolidinone 1 could be opened with anilines to create aryl ureas, phenols to create aryl carbamates, or alcohols to generate alkyl carbamates.

Examples of amines include, without limitation, 1-(1-Naphthyl)ethylamine; 1-(2-Naphthyl)ethylamine; 1-(4-Bromophenyl)ethylamine; 1,1-Diphenyl-2-aminopropane; 1,2,2-Triphenylethylamine; 1,2,3,4-Tetrahydro-1-naphthylamine; 1,2-Bis(2-hydroxyphenyl)ethylenediamine; 1-Amino-2-benzyloxycyclopentane; 1-Aminoindane; 1-Benzyl-2,2-diphenylethylamine; 1-Cyclopropylethylamine; 1-Phenylbutylamine; 2-(3-Chloro-2,2-dimethyl-propionylamino)-3-methylbutanol; 2-(Dibenzylamino)propionaldehyde; 2,2-Dimethyl-5-methylamino-4-phenyl-1,3-dioxane; 2-Amino-1-fluoro-4-methyl-1,1-diphenylpentane; 2-Amino-3,3-dimethyl-1,1-diphenylbutane; 2-Amino-3-methyl-1,1-diphenylbutane; 2-Amino-3-methylbutane; 2-Amino-4-methyl-1,1-diphenylpentane; 2-Aminoheptane; 2-Aminohexane; 2-Aminononane; 2-Aminooctane; 2-Chloro-6-fluorobenzylamine; 2-Methoxy-α-methylbenzylamine; 2-Methyl-1-butylamine; 2-Methylbutylamine; 3,3-Dimethyl-2-butylamine; 3,4-Dimethoxy-α-methylbenzylamine; 3-Amino-2-(hydroxymethyl)propionic acid; 3-Bromo-α-methylbenzylamine; 3-Chloro-α-methylbenzylamine; 4-Chloro-α-methylbenzylamine; 4-Cyclohexene-1,2-diamine; 4-Fluoro-α-methylbenzylamine; 4-Methoxy-α-methylbenzylamine; 7-Amino-5,6,7,8-tetrahydro-2-naphthol; Bis[1-phenylethyl]amine; Bornylamine; cis-2-

Aminocyclopentanol hydrochloride; cis-Myrtanylamine; cis-N-Boc-2-aminocyclopentanol; Isopinocampheylamine; L-Allysine ethylene acetal; Methyl 3-aminobutyrate p-toluenesulfonate salt; N,N'-Dimethyl-1,1'-binaphthyldiamine; N,N-Dimethyl-1-(1-naphthyl)ethylamine; N,N-Dimethyl-1-phenylethylamine; N,α-Dimethylbenzylamine; N-allyl-α-methylbenzylamine; N-Benzyl-α-methylbenzylamine; sec-Butylamine; trans-2-(Aminomethyl)cyclohexanol; trans-2-Amino-1,2-dihydro-1-naphthol hydrochloride; trans-2-Benzyloxycyclohexylamine; α,4-Dimethylbenzylamine; α-Ethylbenzylamine; α-Methylbenzylamine; and β-Methylphenethylamine.

New Allosteric Site #2: C1 Carbonyl O, C3 and C5 Alcohol Hydrogen Bonding Network Having remarkably developed a second set of derivatives supporting the allosteric modification model as a guide for developing less toxic AmB derivatives, the polyol hydrogen-bonding frameworks were targeted. Ideally, simple removal of either the C3 or C11 alcohol would completely abolish the observed extended hydrogen-bonding network. A chemoselective degradative synthesis of either deoxygenated derivative is a challenging synthetic undertaking as chemoselectively targeting one of the nine secondary alcohols present on the AmB framework is nontrivial. A reaction byproduct hinted that the C3 alcohol could potentially be chemoselectively targeted due to its position beta to the C1 carbonyl. Encouraged by this preliminary result, the synthesis of C3deoxyAmB was pursued.

Figure 16:
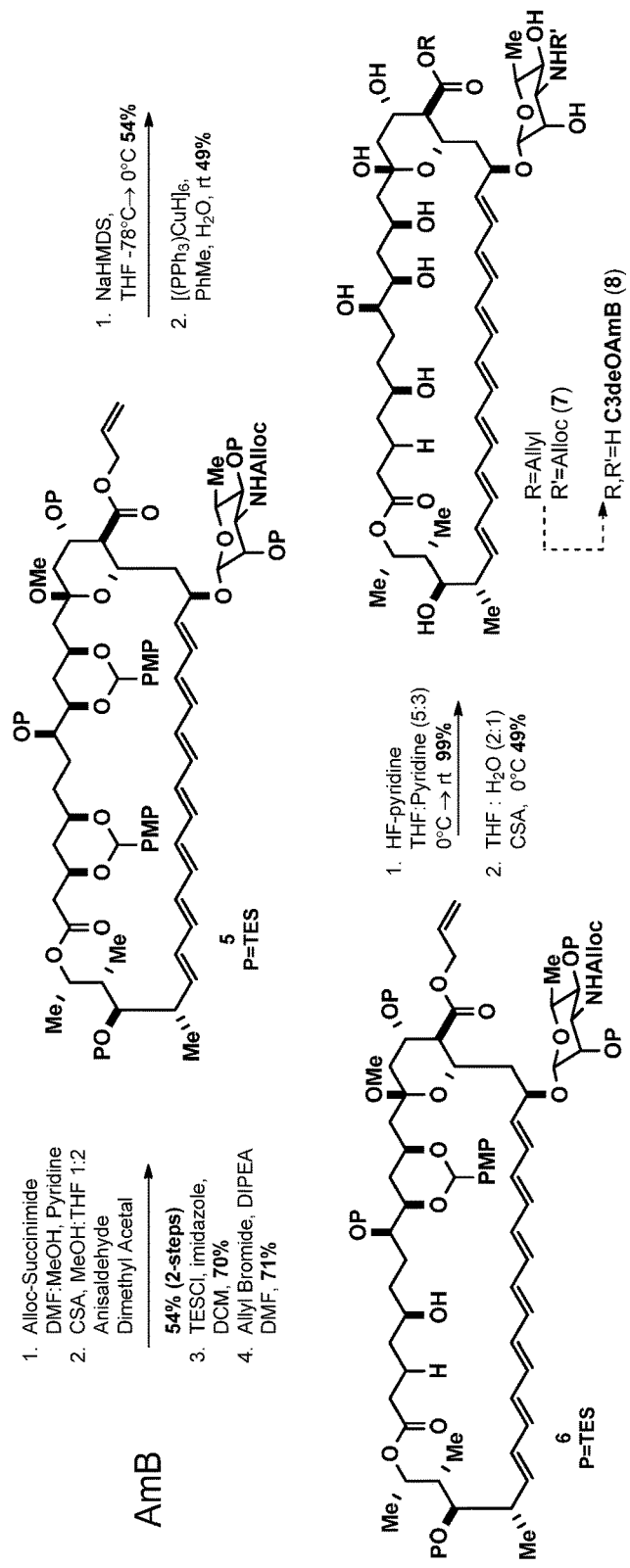
FIG. 16 depicts Scheme 3, a scheme for synthetic efforts toward C3-deoxy AmB (C3deOAmb).

A suitable fully protected intermediate was quickly generated from AmB (Scheme 3, FIG. 16). This sequence involved Alloc protection of the amine, C3/C5 and C9/C11 p-methoxyphenyl acetal formation, TES silylation of the remaining alcohols, and lastly TMSE formation of the C16 carboxylate to form fully protected intermediate 5. Exposure of 5 to NaHMDS at low temperatures smoothly eliminated the C3 alcohol, generating an α-β unsaturated lactone. Stryker reduction of this intermediate efficiently reduced the unsaturation yielding 6, leaving only a deprotection sequence to generate C3deOAmB. Exposure of 6 to HF cleanly removed the TES groups, followed by TBAF-promoted TMSE removal. Methyl ketal and PMP ketal hydrolysis was achieved concomitantly under acidic conditions with HCl. Efforts are currently underway to achieve the final Alloc deprotection of 7 and synthesize C3deOAmB.

New Allosteric Site #3: C9, C11, C13 Hydrogen Bonding Network

Figure 3:
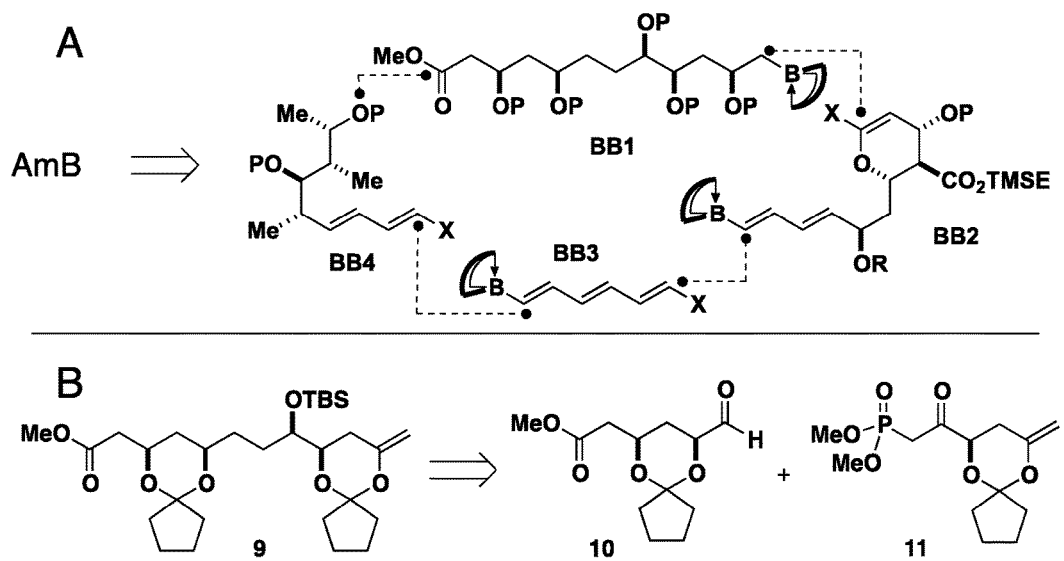
FIG. 3A depicts a retrosynthetic analysis of AmB based on an iterative cross coupling strategy using four building blocks, BB1, BB2, BB3, and BB4.
FIG. 3B depicts a scheme for retrosynthetic analysis of BB1 into two smaller fragments.

Although multiple AmB derivatives can be accessed using natural product degradation, many derivatives are not readily accessible from this platform. An efficient and flexible total synthesis would complement degradative synthesis as a platform for accessing AmB derivatives:[20] For example, total synthesis is a strategy capable of generating either C9 or C11 deoxy AmB to probe the final proposed site of allosteric modification. With this goal in mind, a total synthesis strategy relying on the efficient and flexible iterative Suzuki-Miyaura cross coupling (ICC) platform was developed.[21] As shown in FIG. 3A, AmB is retrosynthetically divided into four building blocks (BB1-4). Using only the Suzuki-Miyaura cross coupling in an iterative fashion we aim to form bonds between building blocks 1 and 2, 2 and 3, and 3 and 4. Subsequent macrolactonization and global deprotection would then complete the total synthesis. Using this strategy, synthesis of C11 deoxy AmB could be achieved by simply substituting BB1 with C11 deoxy BB1, leaving the remainder of the synthesis unchanged.

In order to achieve this challenging synthetic undertaking, the synthesis of BB1 preferably will be efficient, scalable, and capable of long-term storage. As shown in FIG. 3B, we plan to generate protected BB1 (9) by joining fragments 10 and 11. Hydroboration of 9 with 9BBN-borane readies it for Suzuki coupling with BB2. Two key contributions to this total synthesis effort have been made. First, a scalable route to key fragment 10 was devised. Then, upon completion of the synthesis of BB1, the cross coupling of BB1 to BB2 in a model system was investigated.

Figure 17:
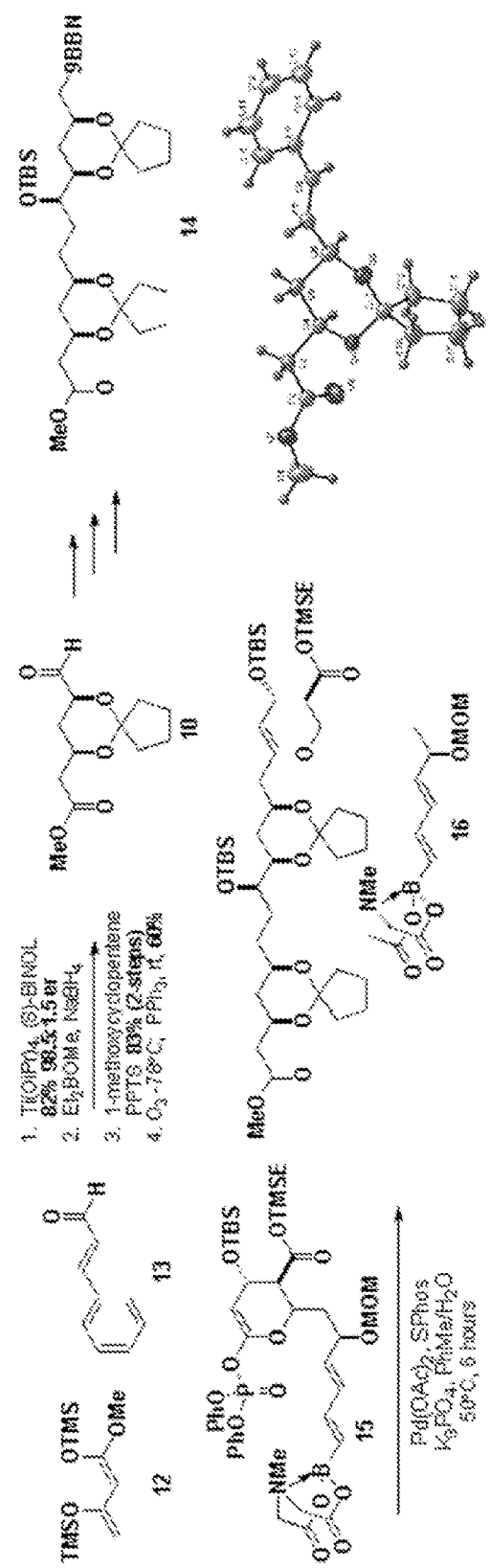
FIG. 17 depicts Scheme 4, a scheme for synthesis of left half of BB1 and efficient coupling of BB1 to BB2.

Three aspects of the initial synthesis of 10 invited improvement.[22] The existing route proceeded in 3% overall yield, required large-scale use of toxic reagents, and proceeded through intermediates not amenable to long-term storage. A second-generation synthesis of 10 (Scheme 4, FIG. 17) was developed to address these issues. Combination of Chan's diene and cinnamaldehyde in the presence of a Titanium/BINOL complex effected an enantioselective extended aldol reaction.[23] Then, a sequence of syn reduction, ketalization, and ozonolysis generated desired aldehyde 10 with an overall yield of 40% from 12. This synthesis eliminates multiple steps, while avoiding unwanted toxic chemicals. The styrene precursor to 10 proved to be highly crystalline. This property proved advantageous, as it could be stored for extended periods of time without decomposition.

With efficient access to 10 established, combination with β-keto phosphonate 11 followed by a 5-step sequence yielded borane 14. With 14 in hand, a reproducible cross coupling with BB2 was targeted. This transformation was predicted to be the most difficult in the ICC sequence as it is the only sp2-sp3 cross coupling. Under anhydrous conditions, we observed no productive coupling between 14 and BB2 surrogate 15, in which the sugar is mimicked with a MOM group. However, addition of 3 equivalents of water, equimolar to the base, promoted desired bond formation. The MIDA boronate on BB2 is stable to these semi-aqueous reaction conditions. These conditions translated to the coupling of BB1 to the glycosylated BB2 in a 60-70% yield. Current efforts are focused on completing the ICC sequence, macrolactonization, and deprotection.

Figure 4:
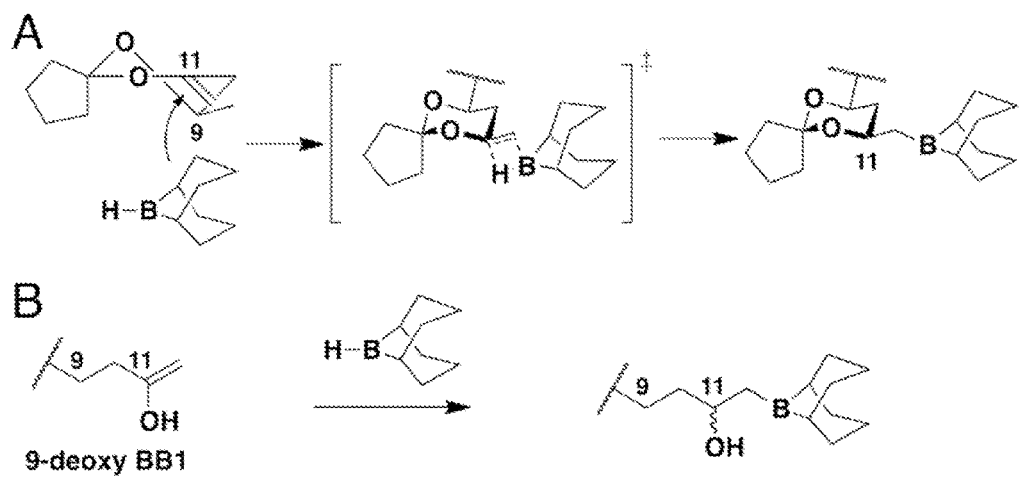
Figure 5:
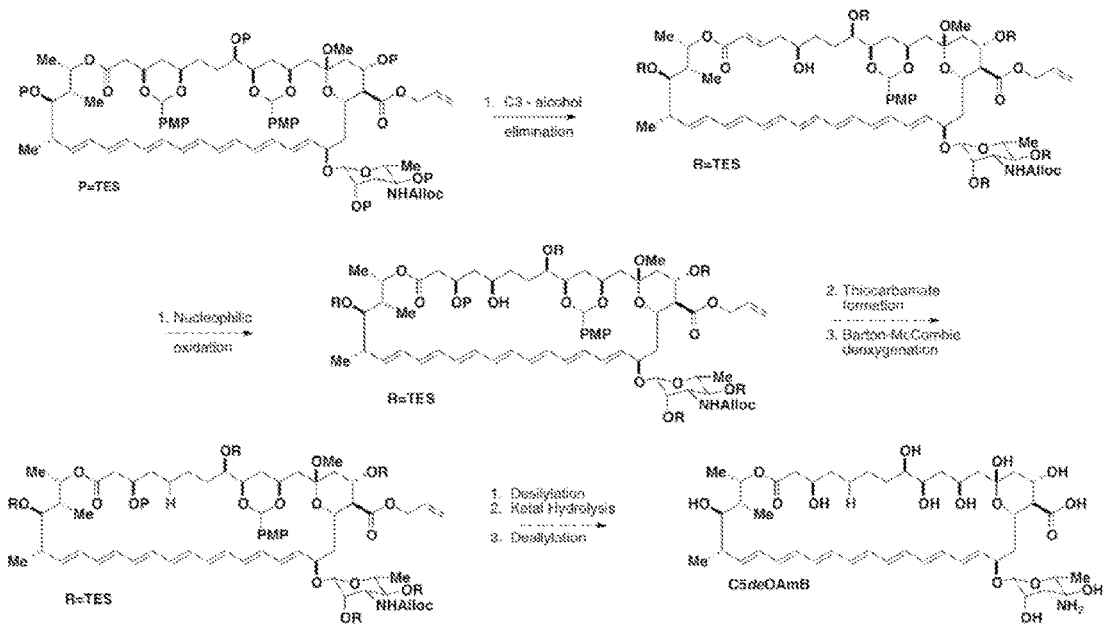
FIG. 5 depicts a generic synthesis of C5deOAmb using a degradative strategy.
Figure 6:
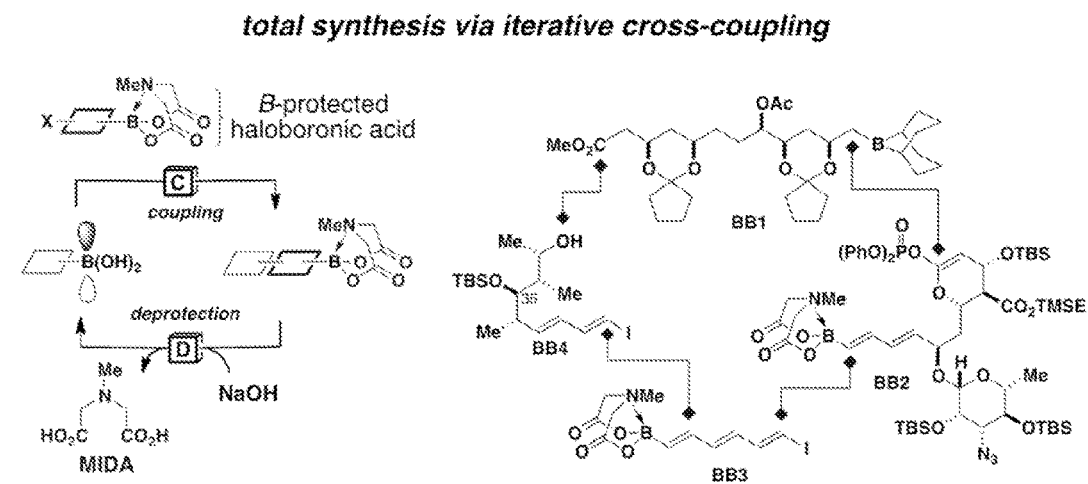
FIG. 6 depicts total synthesis of AmB via iterative cross-coupling.
Figure 7:
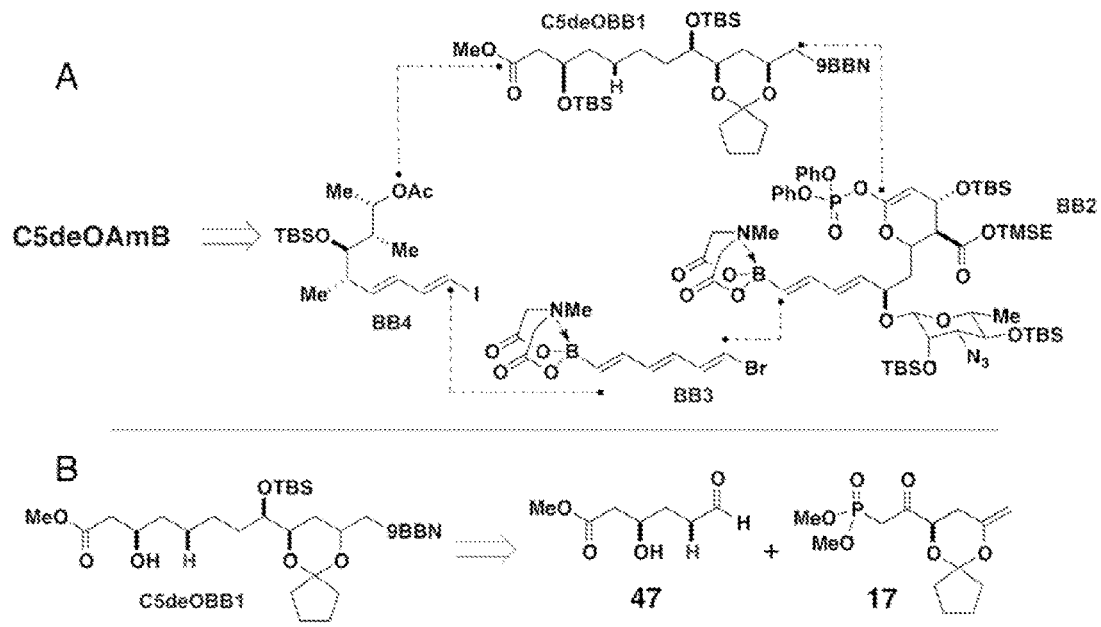
FIG. 7A depicts a retrosynthetic analysis of C5deOAmB leading to four building blocks, BB1, BB2, BB3, and BB4.
FIG. 7B depicts a scheme for retrosynthetic analysis of C5deOBB1 into two smaller fragments.
Figure 8:
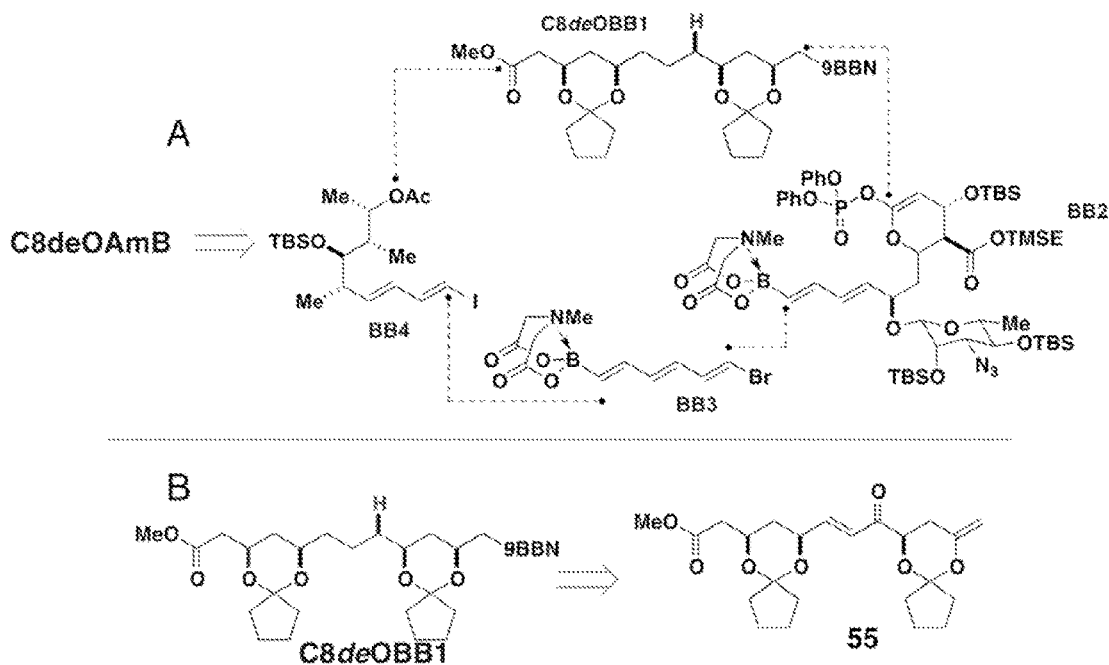
FIG. 8A depicts a retrosynthetic analysis of C8deOAmB leading to four building blocks, BB1, BB2, BB3, and BB4.
FIG. 8B depicts a scheme for retrosynthetic analysis of C8deOBB1 based on reduction of 47.
Figure 9:
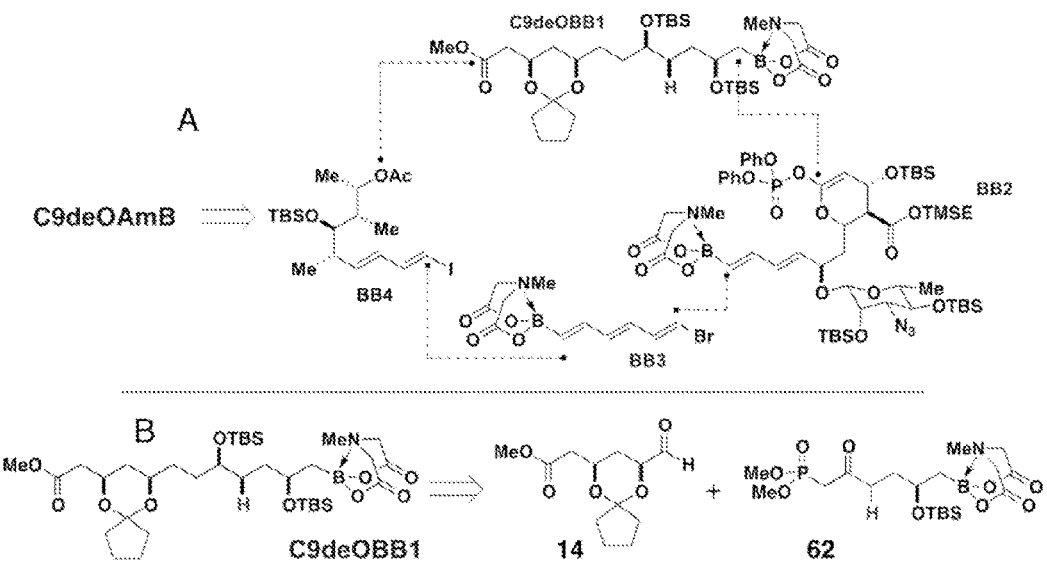
FIG. 9A depicts a retrosynthetic analysis of C9deOAmB leading to four building blocks, BB1, BB2, BB3, and BB4.
FIG. 9B depicts a scheme for retrosynthetic analysis of C9deOBB1 into two smaller fragments.
Figure 10:
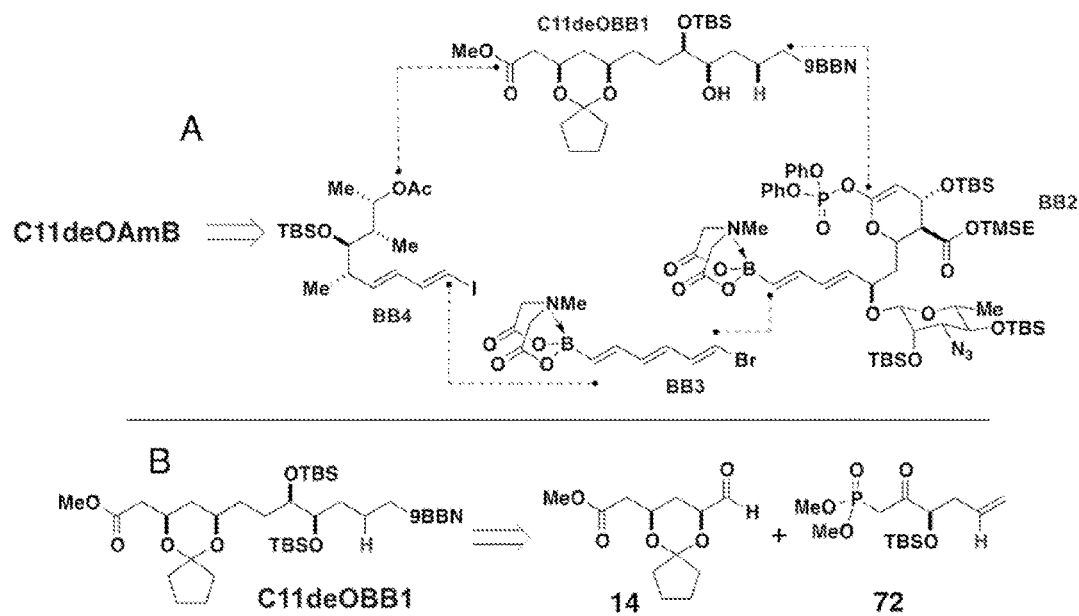
FIG. 10A depicts a retrosynthetic analysis of C11deOAmB leading to four building blocks, BB1, BB2, BB3, and BB4.
FIG. 10B depicts a scheme for retrosynthetic analysis of C11deOBB1 into two smaller fragments.

Derivative synthesis of AmB using the ICC strategy involves only a simple swapping of one of the building blocks for a suitable deoxygenated building block. As a demonstration of this inherent flexibility, efforts have been made towards the synthesis of C9 deoxy BB1. Installation of the C11 stereocenter for BB1 14 is achieved via a stereoselective 9BBN hydroboration which proceeds through a chair-like transition state resulting in only one observed stereochemical outcome (FIG. 4A). If the C9 alcohol is not present, a chair-like transition state is impossible. Therefore, hydroboration would result in a mixture of diastereomers. To overcome this limitation, 9-deoxy BB1 was assembled stereoselectively in a linear fashion starting with a MIDA boronate. This route takes advantage of the ability of MIDA boronates to withstand a variety of common synthetic transformations.[24]

Figure 18:
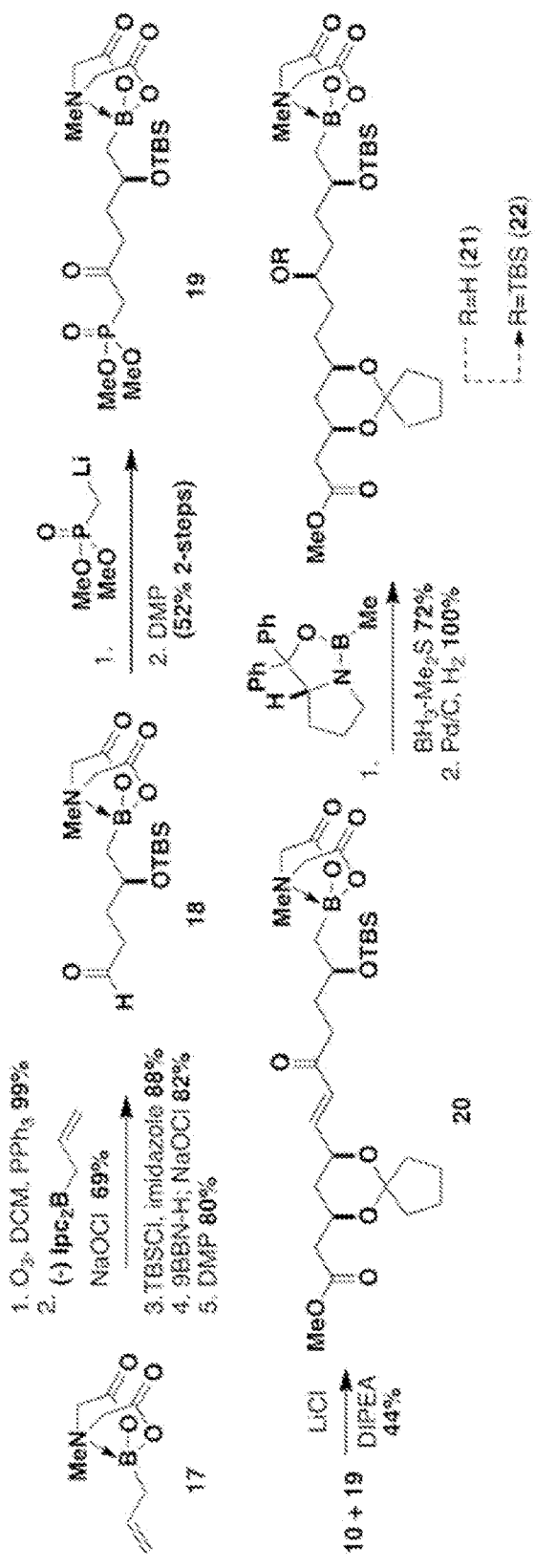
FIG. 18 depicts Scheme 5, a scheme for synthesis of C9-deoxy AmB containing proper oxidation states and stereochemistry at each carbon.

Starting with allyl MIDA boronate 17, a short sequence of ozonolysis, Brown allylation, TBS protection, and hydroboration/oxidation resulted in aldehyde 18 (Scheme 5, FIG. 18). During this initial sequence it was discovered that a bleach, instead of the typical hydrogen peroxide/sodium hydroxide, oxidative workup of the initial brown allylation product efficiently oxidized the carbon-boron bond without decomposition of the MIDA boronate. Exposure of 18 to lithiated dimethyl methyl phosphonate, followed by Dess-Martin oxidation, yielded β-keto phosphonate 19. Demonstrating the convergent nature of the BB1 synthetic strategy, combination of 19 with 10, the same aldehyde used for fully oxidized BB1, in a Horner-Wadsworth-Emmons coupling afforded α-β unsaturated ester 20. Reduction of the carbonyl with the (R)—CBS catalyst, followed by catalytic hydrogenation, yielded 21. This C9 deoxy BB1 intermediate contains the entire carbon framework in the correct oxidation state with all of the stereochemistry preinstalled. Only a TBS protection is required to realize a C9 deoxy BB1 analog ready for MIDA boronate deprotection and coupling with BB2.

Compounds of the Invention

An aspect of the invention is AmBMU or a pharmaceutically acceptable salt thereof

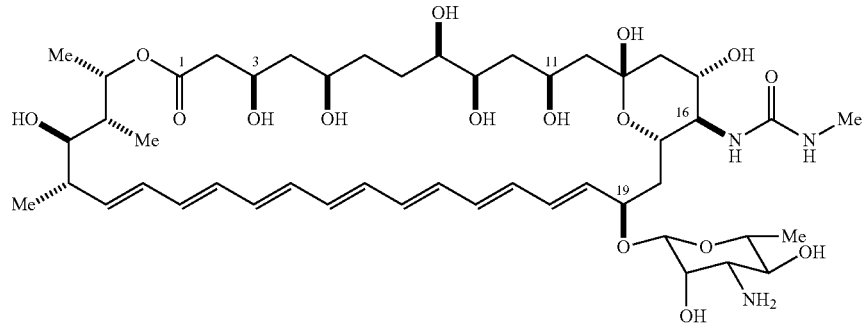

AmBMU

An aspect of the invention is AmBAU or a pharmaceutically acceptable salt thereof

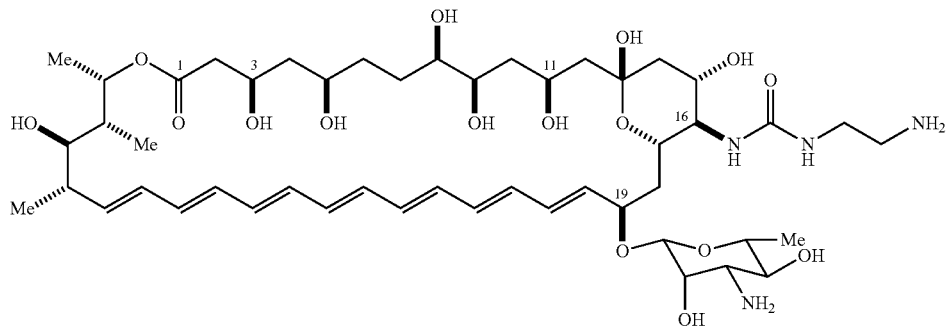

AmBAU

An aspect of the invention is AmBCU or a pharmaceutically acceptable salt thereof

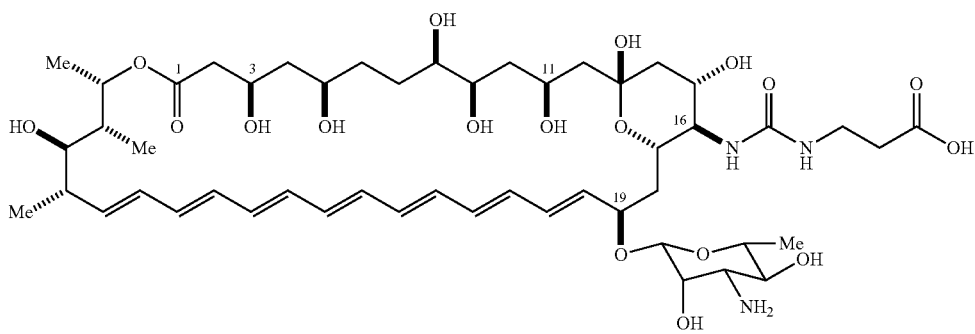

AmBCU

An aspect of the invention is C3deOAmB or a pharmaceutically acceptable salt thereof

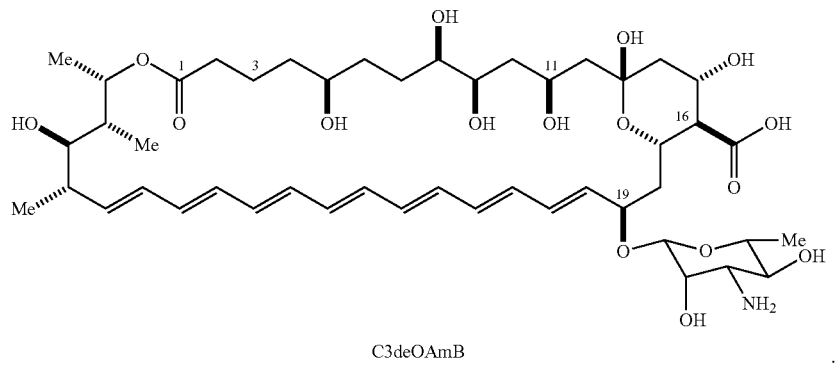

C3deOAmB

An aspect of the invention is C9deOAmB or a pharmaceutically acceptable salt thereof

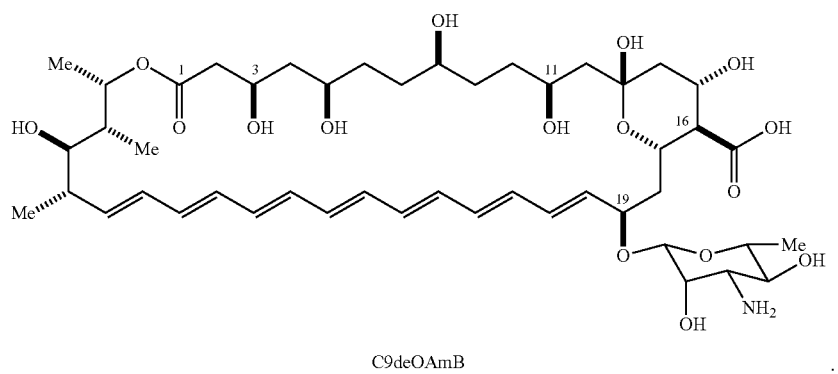

C9deOAmB

An aspect of the invention is C5deOAmB or a pharmaceutically acceptable salt thereof

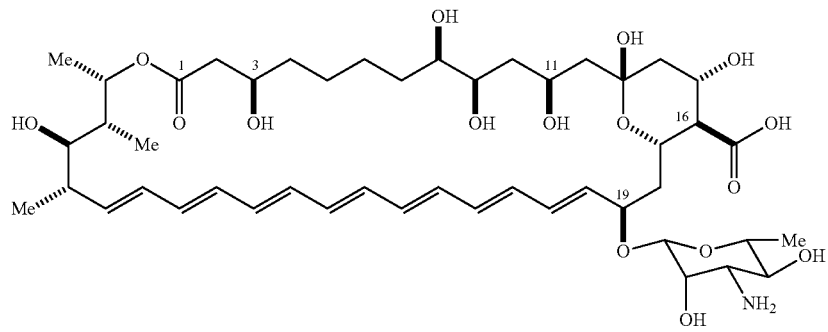

C5deOAmB

An aspect of the invention is C8deOAmB or a pharmaceutically acceptable salt thereof

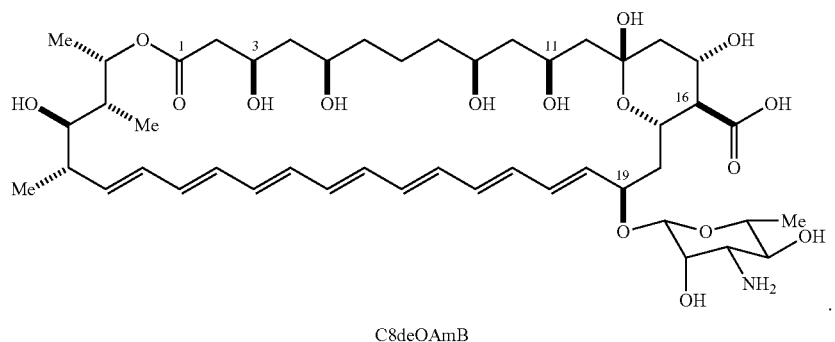
C8deOAmB
An aspect of the invention is C11deOAmB or a pharmaceutically acceptable salt thereof
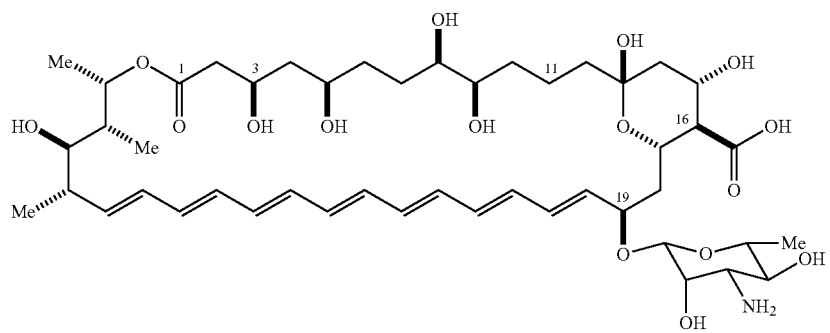
C11deOAmB
An aspect of the invention is C13deOAmB or a pharmaceutically acceptable salt thereof
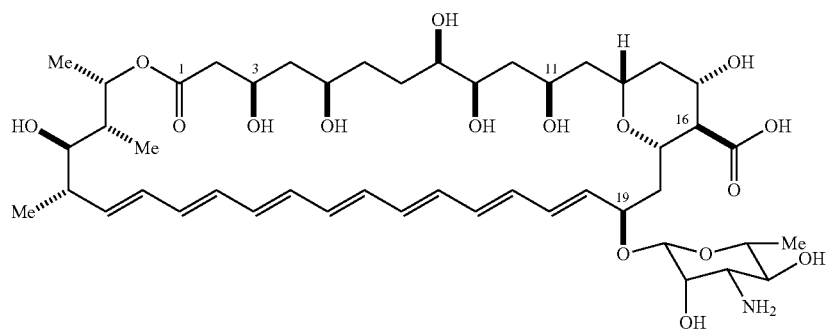
C13deOAmB
An aspect of the invention is C15deOAmB or a pharmaceutically acceptable salt thereof

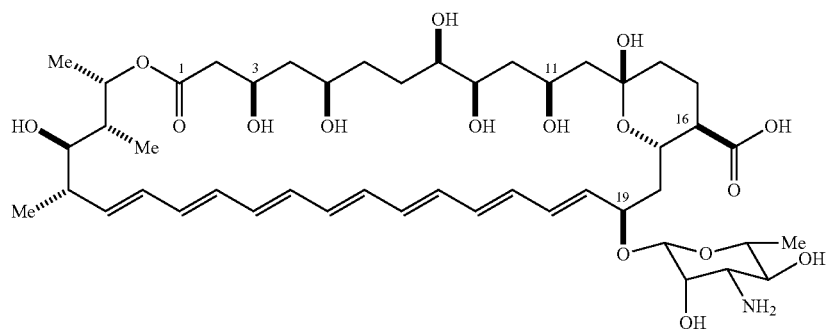
C15deOAmB
An aspect of the invention is C3'deNH$_2$AmB (C3'deamino AmB; C3'deAAmB) or a pharmaceutically acceptable salt thereof
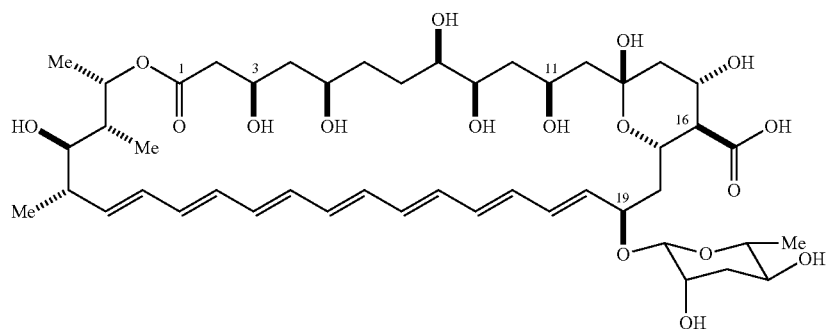
C3'deNH$_2$AmB
An aspect of the invention is C4'deOAmB or a pharmaceutically acceptable salt thereof
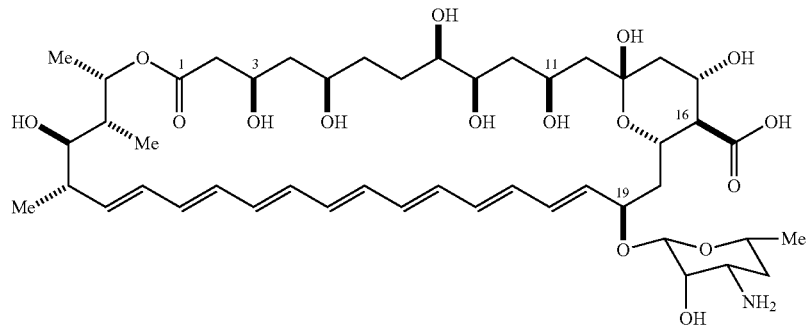
C4'deOAmB An aspect of the invention is Compound X
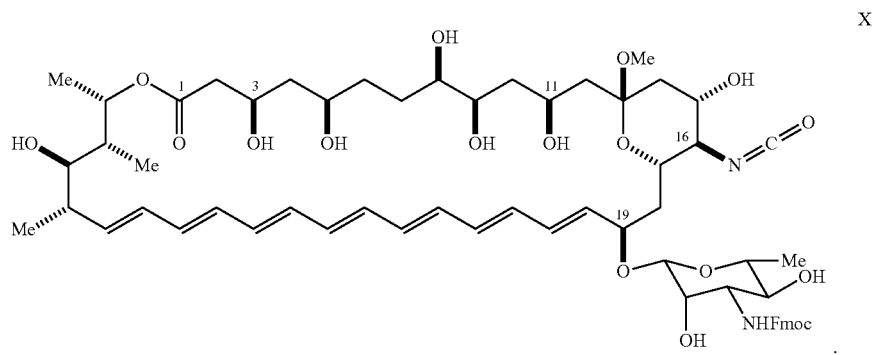
An aspect of the invention is Compound 1
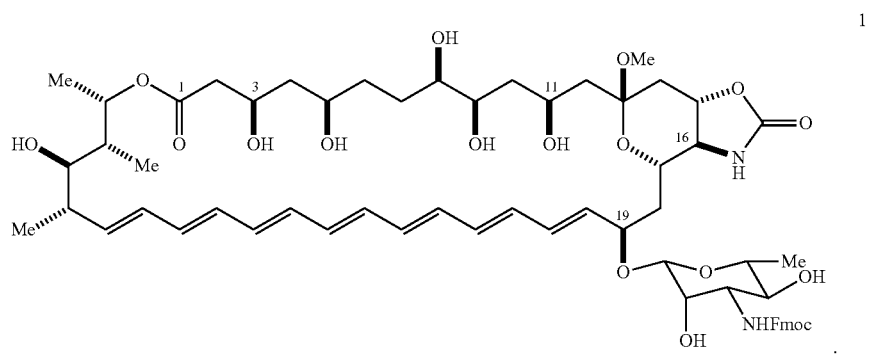
An aspect of the invention is a method of making a C16 urea derivative of amphotericin B according to any one of the six transformations shown in Scheme 2:
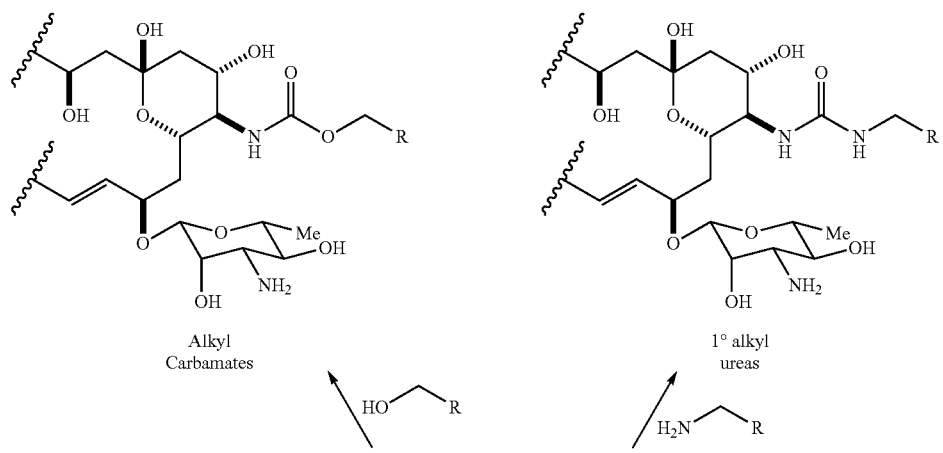

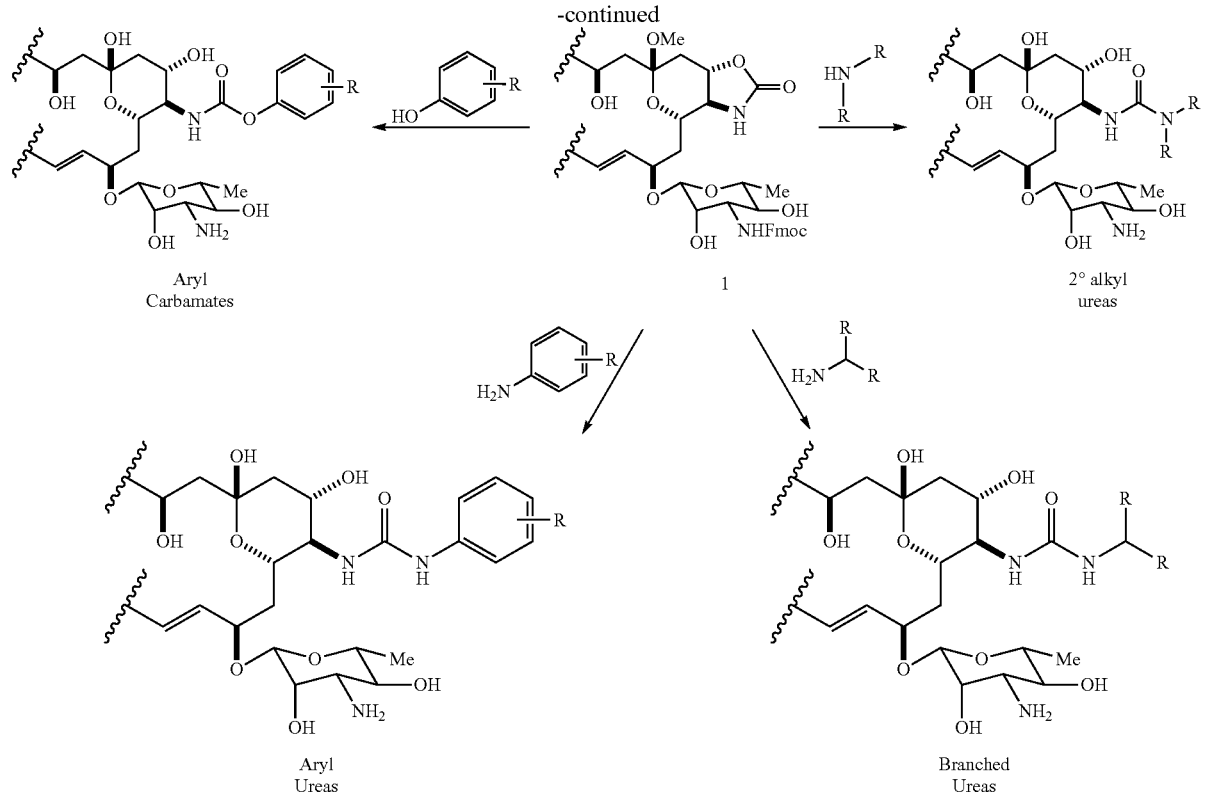

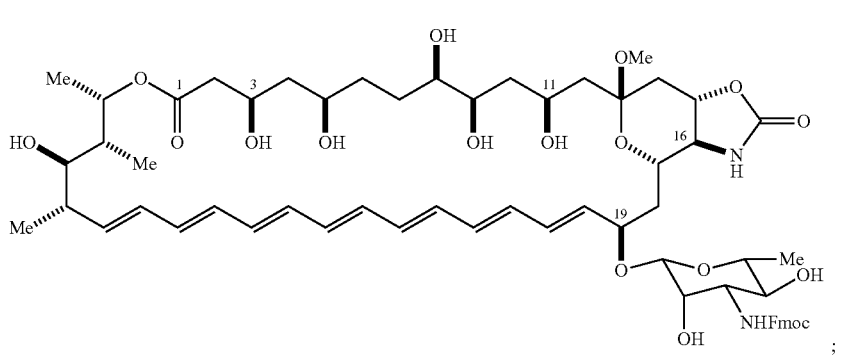

wherein 1 represents and each instance of R is independently selected from the group consisting of hydrogen, halogen, straight- and branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, about 6, or about 7 carbons in the ring structure.

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (i.e., an aromatic or heteroaromatic group).

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "heteroatom" is art-recognized and refers to an atom of any element other than carbon or hydrogen. Illustrative heteroatoms include boron, nitrogen, oxygen, phosphorus, sulfur and selenium.

The term "nitro" is art-recognized and refers to —NO$_2$.

The term "halogen" is art-recognized and refers to —F, —Cl, —Br or —I.

The term "sulfhydryl" is art-recognized and refers to —SH.

The term "hydroxyl" is art-recognized and refers —OH.

The term "sulfonyl" is art-recognized and refers to —SO$_2^-$.

The terms "amine" and "amino" are art-recognized and refer to both unsubstituted and substituted amines, e.g., a moiety that may be represented by the general formulas:

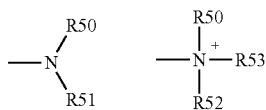

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "amido" is art recognized as an amino-substituted carbonyl and includes a moiety that may be represented by the general formula:

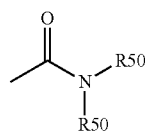

wherein R50 and R51 are as defined above. Certain embodiments of the amide in the present invention will not include imides which may be unstable.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like.

Also provided are pharmaceutical compositions comprising a compound of the invention, or a pharmaceutically acceptable salt thereof, and a pharmaceutically acceptable carrier. Also provided is a method for making such pharmaceutical compositions. The method comprises placing a compound of the invention, or a pharmaceutically acceptable salt thereof, in a pharmaceutically acceptable carrier.

Compounds of the invention and pharmaceutical compositions of the invention are useful for inhibiting the growth of a fungus. In one embodiment, an effective amount of a compound of the invention is contacted with a fungus, thereby inhibiting growth of the fungus. In one embodiment, a compound of the invention, or a pharmaceutically acceptable salt thereof, is added to or included in tissue culture medium.

Compounds of the invention and pharmaceutical compositions of the invention are useful for the treatment of fungal infections in a subject. In one embodiment, a therapeutically effective amount of a compound of the invention, or a pharmaceutically acceptable salt thereof, is administered to a subject in need thereof, thereby treating the fungal infection.

A fungus is a eukaryotic organism classified in the kingdom Fungi. Fungi include yeasts, molds, and larger organisms including mushrooms. Yeasts and molds are of clinical relevance as infectious agents.

Yeasts are eukaryotic organisms classified in the kingdom Fungi. Yeasts are typically described as budding forms of fungi. Of particular importance in connection with the invention are species of yeast that can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic yeasts include, without limitation, various species of the genus *Candida*, as well as of *Cryptococcus*. Of particular note among pathogenic yeasts of the genus *Candida* are *C. albicans, C. tropicalis, C. stellatoidea, C. glabrata, C. krusei, C. parapsilosis, C. guilliermondii, C. viswanathii*, and *C. lusitaniae*. The genus *Cryptococcus* specifically includes *Cryptococcus neoformans*. Yeast can cause infections of mucosal membranes, for example oral, esophageal, and vaginal infections in humans, as well as infections of bone, blood, urogenital tract, and central nervous system. This list is exemplary and is not limiting in any way.

A number of fungi (apart from yeast) can cause infections in mammalian hosts. Such infections most commonly occur in immunocompromised hosts, including hosts with compromised barriers to infection (e.g., burn victims) and hosts with compromised immune systems (e.g., hosts receiving chemotherapy or immune suppressive therapy, and hosts infected with HIV). Pathogenic fungi (apart from yeast) include, without limitation, species of *Aspergillus, Rhizopus, Mucor, Histoplasma, Coccidioides, Blastomyces, Trichophyton, Microsporum*, and *Epidermophyton*. Of particular note among the foregoing are *A. fumigatus, A. flavus, A. niger, H. capsulatum, C. immitis*, and *B. dermatitidis*.

Fungi can cause systemic and deep tissue infections in lung, bone, blood, urogenital tract, and central nervous system, to name a few. Some fungi are responsible for infections of the skin and nails.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

A "fungal infection" as used herein refers to an infection in or of a subject with a fungus as defined herein. In one embodiment the term "fungal infection" includes a yeast infection. A "yeast infection" as used herein refers to an infection in or of a subject with a yeast as defined herein.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

As used herein, a "subject having a yeast or fungal infection" refers to a subject that exhibits at least one objective manifestation of a yeast or fungal infection. In one embodiment a subject having a yeast or fungal infection is a subject that has been diagnosed as having a yeast or fungal infection and is in need of treatment thereof. Methods of diagnosing a yeast or fungal infection are well known and need not be described here in any detail.

As used herein, "administering" has its usual meaning and encompasses administering by any suitable route of administration, including, without limitation, intravenous, intramuscular, intraperitoneal, intrathecal, intraocular (e.g., intravitreal), subcutaneous, direct injection (for example, into a tumor), mucosal, inhalation, oral, and topical.

In one embodiment, the administration is intravenous.

In one embodiment, the administration is oral.

As used herein, the phrase "effective amount" refers to any amount that is sufficient to achieve a desired biological effect.

As used herein, the phrase "therapeutically effective amount" refers to an amount that is sufficient to achieve a desired therapeutic effect, e.g., to treat a yeast or fungal infection.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include other antifungal agents, including AmB, as well as other antibiotics, anti-viral agents, anti-inflammatory agents, immunosuppressive agents, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a compound of the invention may typically be from 0.1 mg/kg/day to 20 mg/kg/day. Intravenous dosing thus may be similar to, or advantageously, may exceed maximal tolerated doses of AmB.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

Amphotericin B is commercially available in a number of formulations, including deoxycholate-based formulations and lipid-based (including liposomal) formulations. Amphotericin B derivative compounds of the invention similarly may be formulated, for example, and without limitation, as deoxycholate-based formulations and lipid-based (including liposomal) formulations.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, inhalation, and topical.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13 (suppl. 5):143-146 (1989) (endothelin-1); Hubbard et al., *Annal Int Med* 3:206-212 (1989) (al-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1. C5-Deoxy AmB

Figure 19:
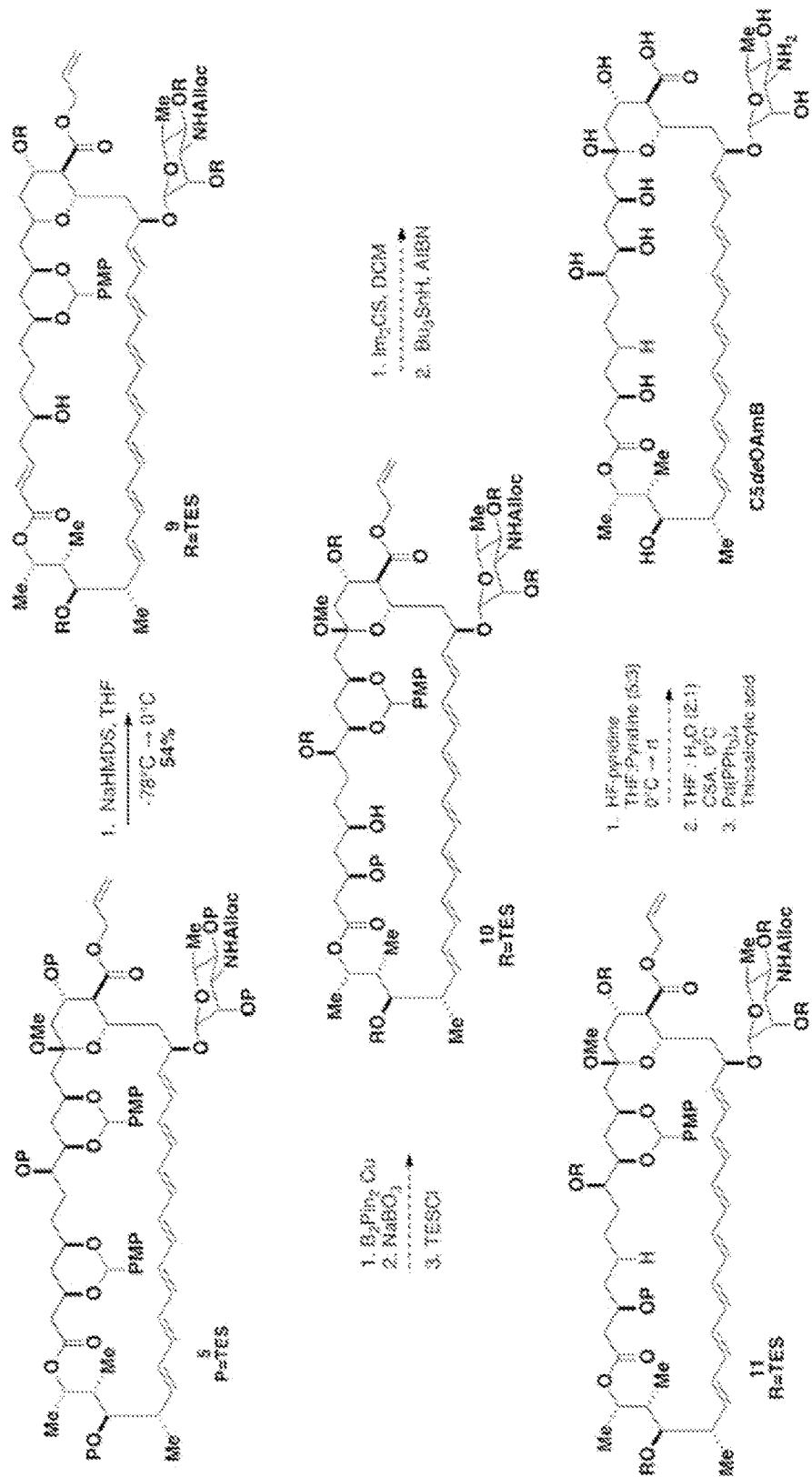
FIG. 19 depicts Scheme 6 in accordance with Example 1.
Figure 20:
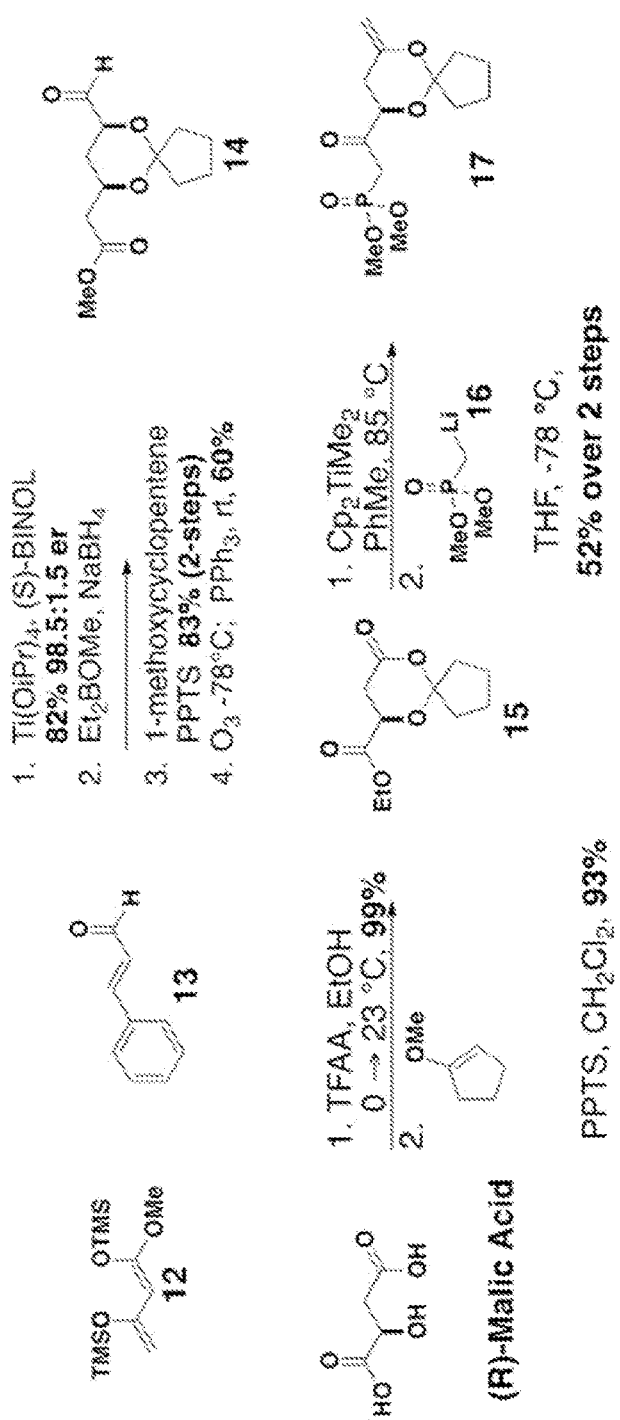
FIG. 20 depicts Scheme 7 in accordance with Example 2.
Figure 20:
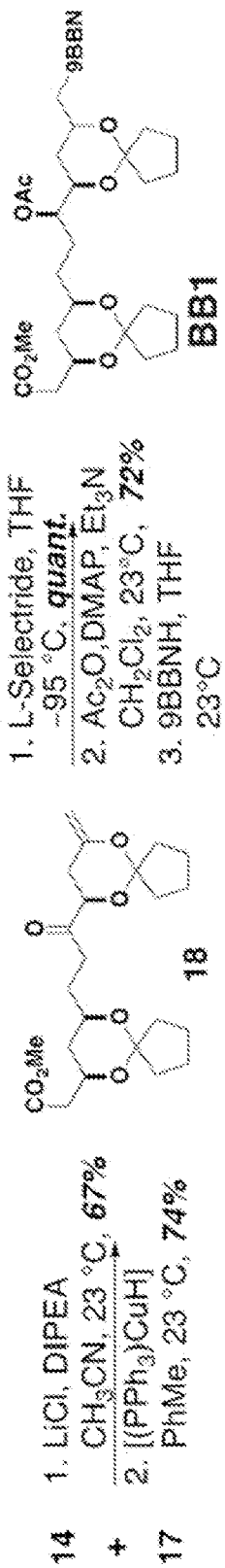
Figure 21:
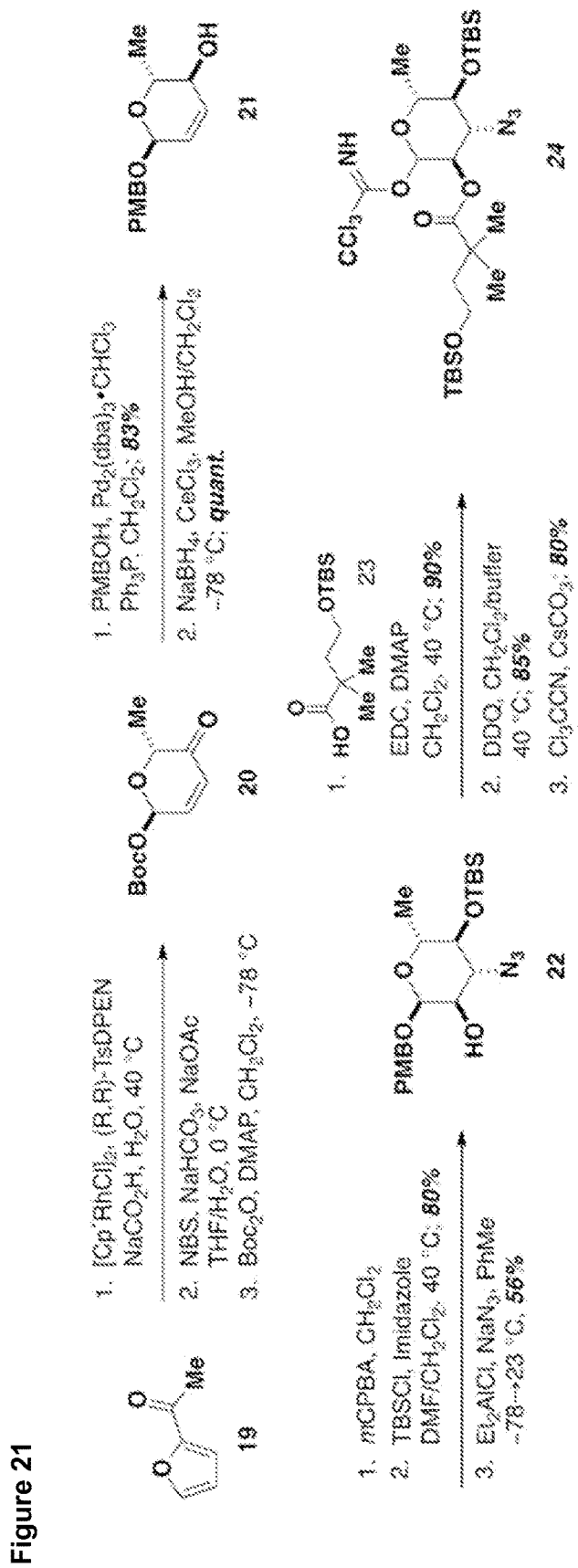
FIG. 21 depicts Scheme 8 in accordance with Example 2.
Figure 22:
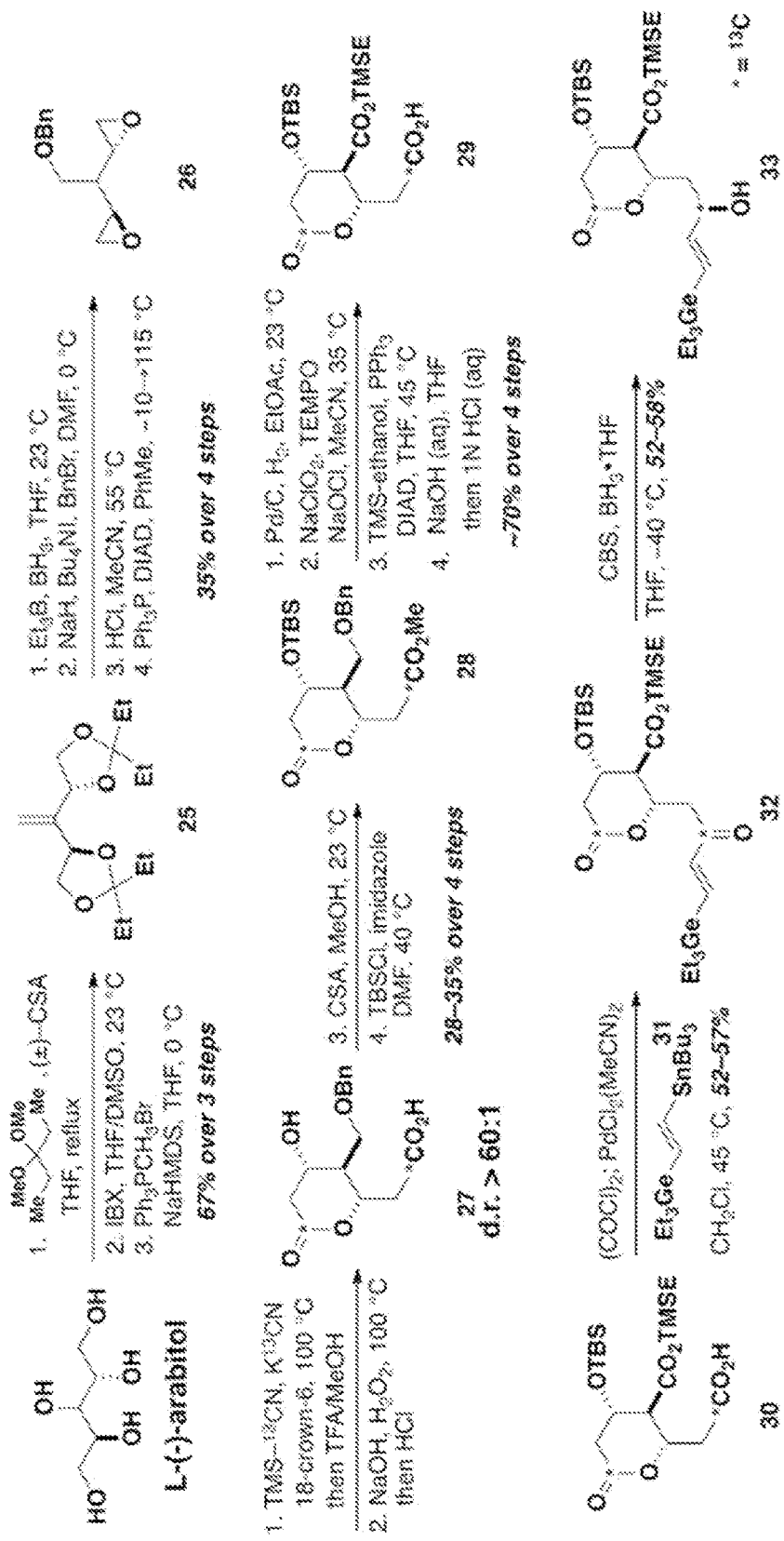
FIG. 22 depicts Scheme 9 in accordance with Example 2.
Figure 23:
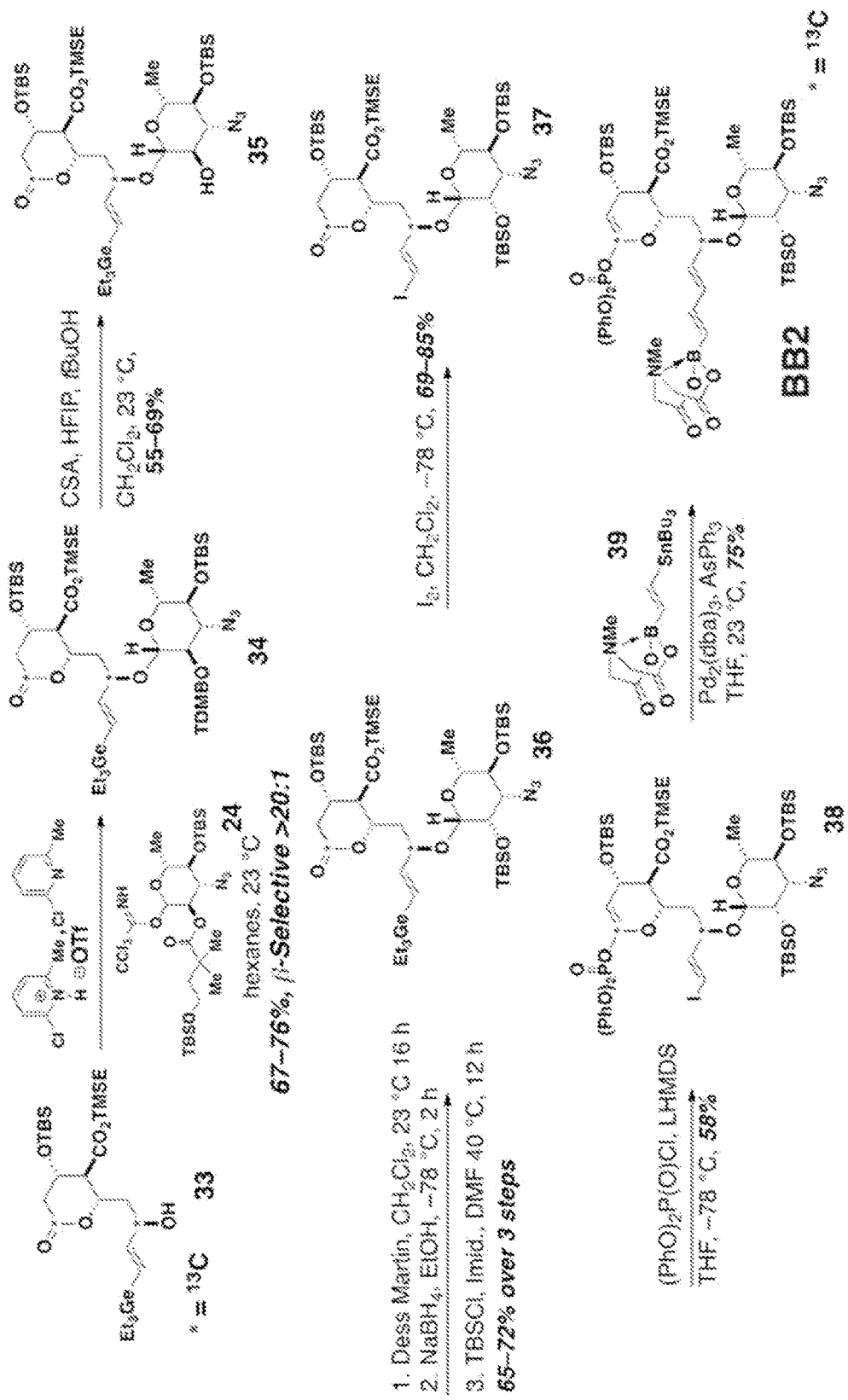
FIG. 23 depicts Scheme 10 in accordance with Example 2.
Figure 24:
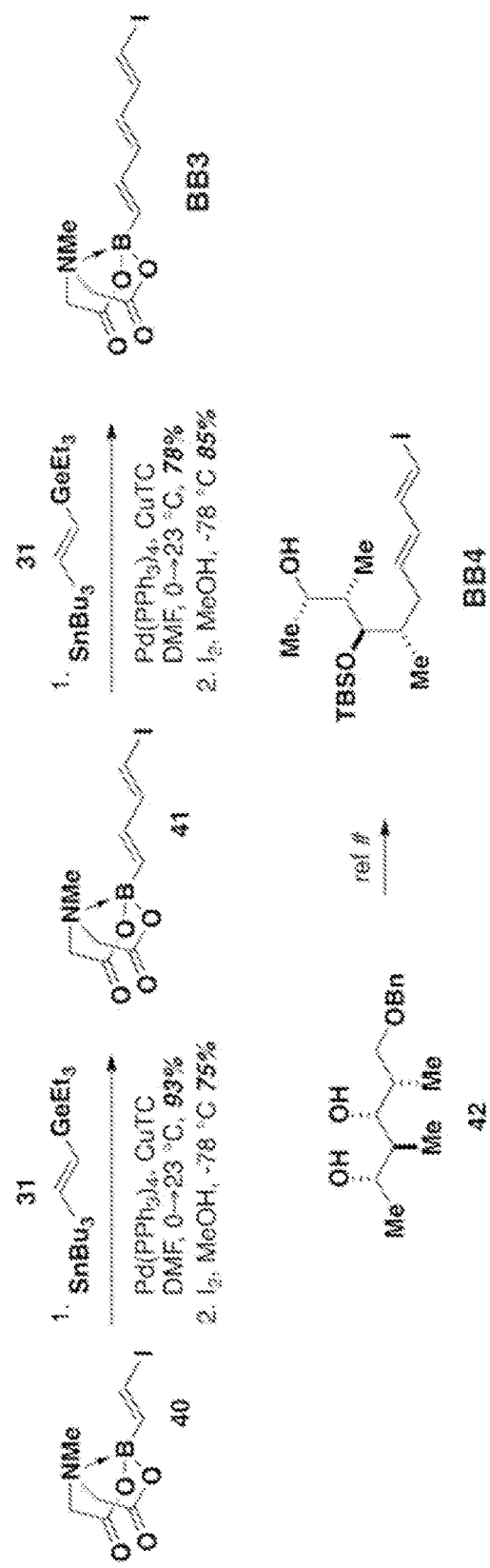
FIG. 24 depicts Scheme 11 in accordance with Example 2.
Figure 25:
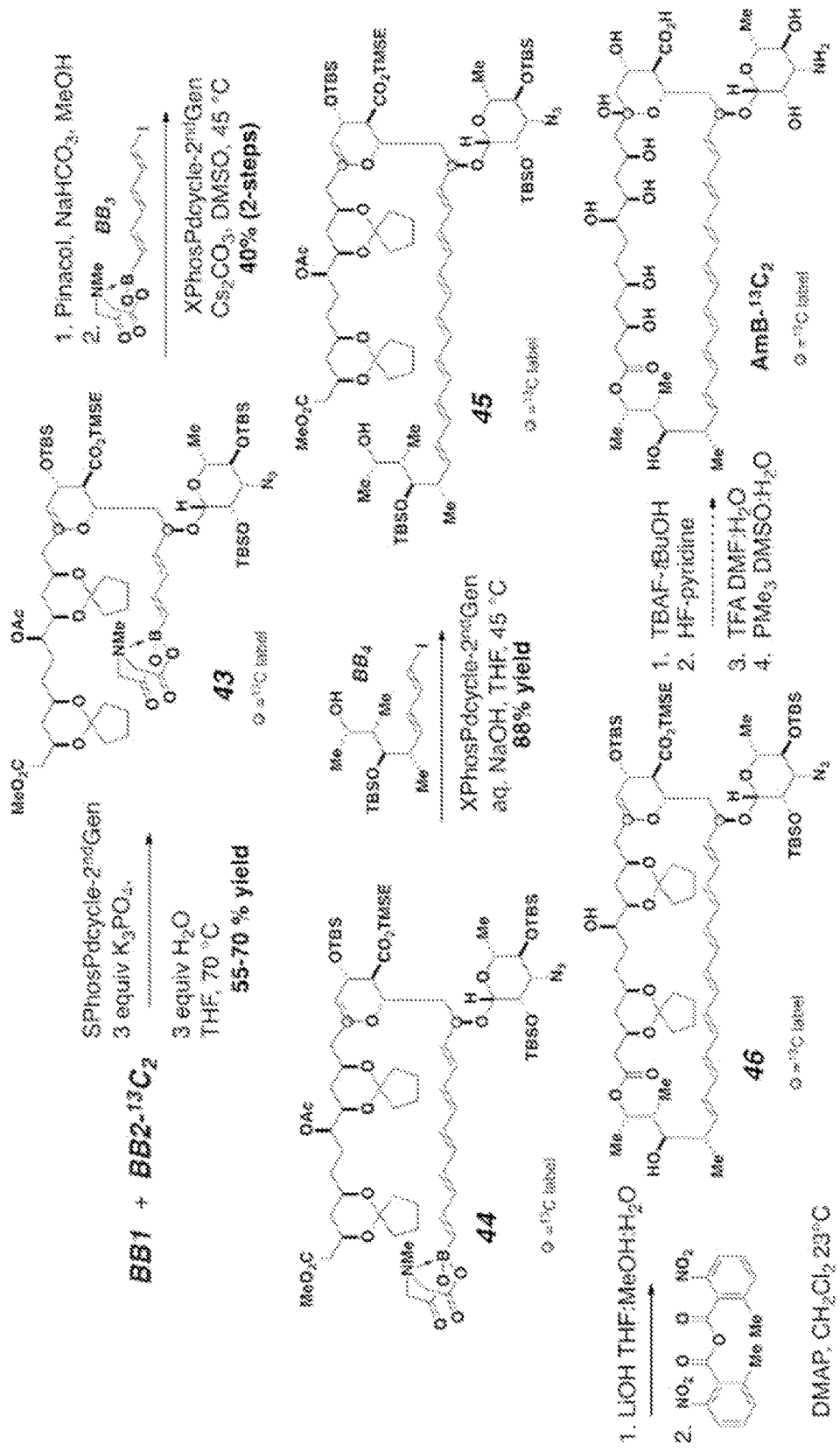
FIG. 25 depicts Scheme 12 in accordance with Example 2.

Degradative Synthesis
See Scheme 6, FIG. 19.
One potential synthetic strategy to gain access to C5-deoxyAmB (C5deOAmB) is a degradative synthesis starting with the natural product AmB. Using fully protected intermediate 5 as a starting point, upon elimination of the C3 alcohol, alpha-beta unsaturated ester 9 is generated. A nucleophilic oxidation of the beta-carbon would re-install the necessary hydroxyl group at C-3, leaving the C-5 alcohol of as the only unprotected alcohol on the AmB framework. From here a Barton-McCombie type deoxygenation could remove the C-5 alcohol. Then a short deprotection sequence could afford C5deOAmB.

Specifically we anticipate using intermediate 3, an intermediate accessible using a sequence similar to that utilized in the synthesis of C3-deoxyAmB. Exposure of 5 to NaHMDS cleanly eliminates the C-3 alcohol in 54% yield. A nucleophilic addition using $B_2Pin_2$ catalyzed by a copper catalyst could selectively borylate at the beta position. Subsequent oxidation with sodium perborate, followed by TBS silylation could potentially re-install the oxidation at C-3 in a protected form. Then, thiocarbonyl formation using thiocarbonyldiimidazole followed by a radical deoxygenation with tributyltin hydride and Azobisisobutyronitrile could generate C-5 deoxygenated AmB framework 11. A deprotection sequence involving HF-pyridine removal of silyl groups, followed by ketal hydrolysis with CSA in $THF:H_2O$ 2:1, and lastly concomitant removal of both the allyl ester and alloc carbamate could quickly generate C5deOAmB.

Example 2. C5-deoxy AmB

Total Synthesis of Doubly $^{13}C$ Labeled AmB Macrolactone
See Schemes 7-12, FIGS. 20-25.
A total synthesis strategy relying on the efficient and flexible iterative Suzuki-Miyaura cross coupling (ICC) platform is envisioned. The ICC strategy takes advantage of bifunctional B-protected haloboronic acids which can be exposed to a suitable boronic acid partner and selectively react under Suzuki-Miyaura cross coupling conditions at only the halide terminus. Deprotection of the MIDA ligand using basic hydrolysis to a free boronic acid readies the building block for the next cycle of cross coupling. As shown in FIG. 3A, AmB is retrosynthetically divided into four building blocks (BB1-BB4). Using only the Suzuki-Miyaura cross coupling in an iterative fashion we aim to form bonds between building blocks 1 and 2, 2 and 3, and 3 and 4. Subsequent macrolactonization and global deprotection would then complete the total synthesis. Using this strategy, synthesis of a deoxygenated derivative only requires the synthesis of a new deoxygenated building block, leaving the remainder of the synthesis unchanged. For instance, synthesis of C5-deoxy AmB could be achieved by simply substituting BB1 with C-5 deoxy BB1.

The synthesis of BB1 arising from the coupling of two smaller fragments, aldehyde 14, and beta-keto phosphonate 17. The synthesis of aldehyde 14 commences with combination of Chan's diene 12 and cinnamaldehyde 13 in the presence of a Titanium/BINOL complex affects an enantioselective extended aldol reaction. Then, a sequence of syn reduction, ketalization and ozonolysis generates desired aldehyde 14 with an overall yield of 40% from 12. The synthesis of the right half of C5deOAmB begins with the selective esterification of (R)-malic acid followed by ketalization to provide cyclopentylidene ketal 15. Exposure of 15, to Petasis' reagent followed by ketone formation upon exposure to lithiated dimethyl methyl phosphonate 16 affords beta-keto phosphonate 17.

Upon generation of both the left and right halves of BB1, a Horner-Wadsworth-Emmons coupling joins fragments 14 and 17. Subsequent Stryker reduction then generates ketone 18. A diastereoselective ketone reduction resulting from exposure of 18 to L-selectride, followed by acylation of the resulting alcohol, and a final hydroboration of the methylene dioxane readies C5deOAmB for Suzuki-Miyaura cross coupling with BB2.

Similar to BB1, BB2 is also divided into two smaller fragments. Sugar donor 24, and glycosyl acceptor 33 will be joined in a diastereoselective glycosylation reaction. First, the two smaller fragments must be synthesized. The synthesis of 24 starts with 2-furyl methyl ketone. Reduction of the ketone followed by an Achmatowicz reaction promoted by NBS and subsequent Boc protection generates dihydropyran 20. Next, exchange of the Boc acetal for a para-methoxybenzyl acetal followed by ketone reduction under Luche conditions provides access to allylic alcohol 21. The allylic alcohol is then used to control the facial selectivity of a mCPBA epoxidation before it is silylated with TBSCl and imidazole. Site selective opening of the epoxide is then achieved by opening with a deithylalumminumazide complex to yield azido-alcohol 22. Next, the free alcohol is esterified with EDC, DMAP, and TDMBA. Lastly, reduction of the PMB alcohol is achieved upon exposure to DDQ and subsequent trichloroacetimidate formation realizes the synthesis of fully protected C2'-epimycosamine sugar donor 24, ready for glycosylation with allylic alcohol 33.

Starting from L-(−)-arabitol, bis ketalization followed by alcohol oxidation with IBX, and Wittig olefination provides 1,1-disubstituted olefin 25. Hydroboration of 25, followed by benzylation, and acid cleavage of both ethyl ketals generates an intermediate capable cyclization to afford bis-epoxide 26. Opening of bis-epoxide 26 with TMSCN and KCN in the presence of 18-crown-6 generates a bis-cyano diol, which upon hydrolysis to a bis-carboxylic acid undergoes an intramolecular diastereotopic group selective lactonization to provide lactone 27. Simple methyl esterification and TBS silylation then provide lactone 28. Debenzylation, upon exposure of 28 to palladium on carbon and hydrogen, followed by Pinnick oxidation, and then Mitsunobu reaction with TMS-ethanol provides a differentially substituted di-ester capable of selective saponification with sodium hydroxide to provide acid 29. Acid chloride formation of 29 with oxalyl chloride followed by Stille coupling with bis-metalated olefin 31 provides alpha-beta unsaturated ketone 32. Diastereoselective reduction of ketone 32 to allylic alcohol 33 is achieved with a CBS reduction ready for glycosylation with 24.

Taking advantage of the anchimeric assistance platform for controlled beta-glycosylation, combination of 24 and 33 in the presence of buffered chloro-methyl pyridinium triflate provides 34 with greater than 20:1 beta to alpha selectivity. The TDMB directing group is then removed upon exposure to CSA in hexafluoroisopropanol, tert-butanol, and methylene chloride revealing free alcohol 35. A three-step sequence of oxidation, reduction of the resulting ketone and silylation accesses TBS ether 36. Iodo-degermylation followed by exposure to diphenyl phosphoryl chloride and LiHMDS grants access to ketene acetal phosphonate 38. A selective Stille coupling to tributyl stannane 39 achieves the synthesis of BB2.

Iodo-triene BB3 is the least complex of the four building blocks. Its synthesis is achieved in four steps, starting trans-vinyl iodide MIDA boronate 40. A Stille coupling with 31 using Pd(PPh$_3$)$_4$ and CUTC, followed by iodo-degermylation provides diene 41. The olefin network is then extended by another vinyl group with a second Stille coupling with 31, and subsequent iodo-degermylation to access BB3. The synthesis of BB4 is achieved rapidly following literature precedent from our group. Lee, S J et al., *J Am Chem Soc* 130:466 (2008); Paterson, I et al., *J Am Chem Soc* 123:9535 (2001).

With all four building blocks in hand, they can now be assembled using the iterative cross coupling platform to rapidly generate the AmB macrolactone. Combination of BB1 and BB2 with Buchwald's $2^{nd}$ generation SPhos palladacycle, potassium phosphate, and 3 equivalents of water effects a Suzuki-Miyaura cross coupling to form BB1-BB2 dimer 43. Pinacol exchange of the MIDA boronate, followed by a second Suzuki coupling with BB3, this time with the XPhos-Generation 2 palladacycle forms pentaene 44. An in-situ release of the MIDA boronate to a free boronic acid with sodium hydroxide in the presence of the palladium $2^{nd}$ generation XPhos palladacycle forms the all carbon linear framework of AmB, 45. After saponification of methyl ester 45 with lithium hydroxide, a macrolactonization then affords the double $^{13}$C labeled macrolactone of AmB, 46. A series of protecting group removals including TMSE deprotection with TBAF-tBuOH complex, global desilylation with HF-pyridine, deketalization with trifluoroacetic acid, and Staudinger reduction of the C3' azide with trimethylphosphine should achieve the synthesis of AmB-$^{13}$C$_2$.

Example 3. C5-deoxy AmB

Total Synthesis of C5deOAmB

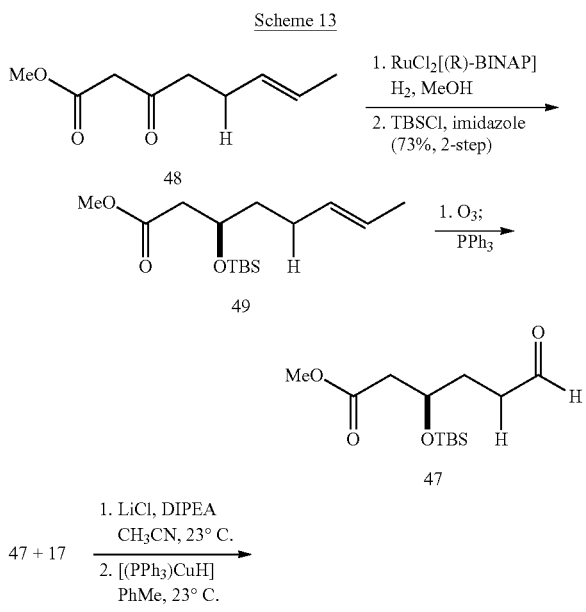

Scheme 13

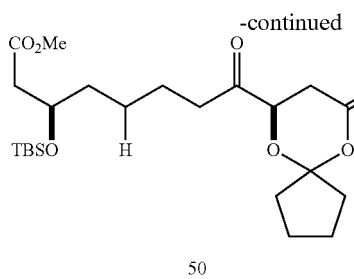

50

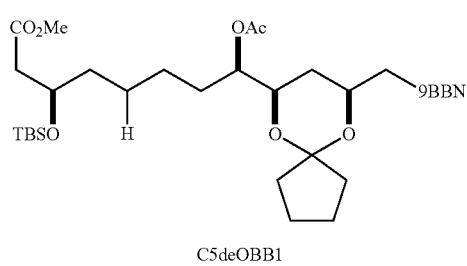

C5deOBB1

An alternative synthetic strategy to access C5-deoxy AmB is through a total synthesis effort. We envision the synthesis of C5deOBB1 arising from the coupling of two smaller fragments, aldehyde 47, and beta-keto phosphonate 17. The synthesis of aldehyde 47 commences with beta-keto ester 48, available after alkylation of methyl acetoacetate. Noyori hydrogenation of 48, followed by TBS silylation provides silyl ether 49. From 49, only an ozonolysis remains to finish the left half of C5deOAmB.

Upon generation of both the left and right halves of C5deOAmB we anticipate a Horner-Wadsworth-Emmons coupling to join fragments 47 and 17. Subsequent Stryker reduction would then generate ketone 50. A diastereoselective ketone reduction resulting from exposure of 50 to L-selectride, followed by acylation of the resulting alcohol, and a final hydroboration readies C5deOBB1 for Suzuki-Miyaura cross coupling with BB2.

Figure 26:
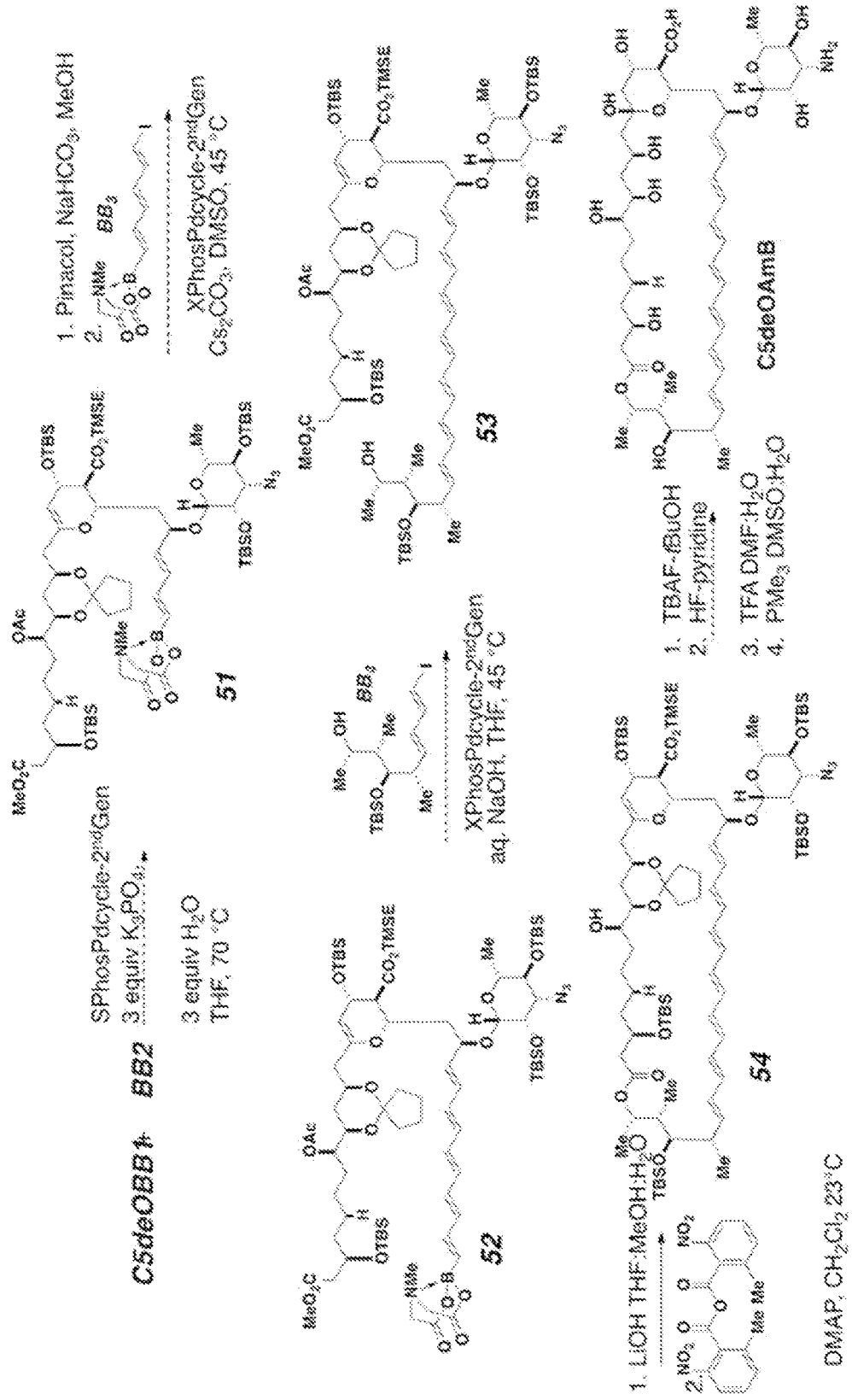
FIG. 26 depicts Scheme 14 in accordance with Example 3.

See Scheme 14, FIG. 26.

With all four building blocks in hand, they can now be assembled using the iterative cross coupling platform to rapidly generate with the C5deOAmB macrolactone. We anticipate combination of C5deOBB1 and BB2 with Buchwald's $2^{nd}$ generation SPhos palladacycle, potassium phosphate, and 3 equivalents of water will effect a Suzuki-Miyaura cross coupling to form C5deOBB1-BB2 dimer 51. Pinacol exchange of the MIDA boronate, followed by a second Suzuki coupling with BB3, this time with the XPhos-Generation 2 palladacycle will form pentaene 52. An in situ release of the MIDA boronate to a free boronic acid with sodium hydroxide in the presence of the palladium $2^{nd}$ generation XPhos palladacycle will form the all carbon linear framework of C5deOAmB 53. After saponification of methyl ester 53 with lithium hydroxide, a macrolactonization should then afford macrolactone 54. A series of protecting group removals including TMSE deprotection with TBAF-tBuOH complex, global desilylation with HF-pyridine, deketalization with trifluoroacetic acid, and Staudinger reduction of the C3' azide with trimethylphosphine should achieve the synthesis of C5deOAmB.

Example 4. C8-deoxy AmB

Total Synthesis of C8deOAmB

Figure 27:
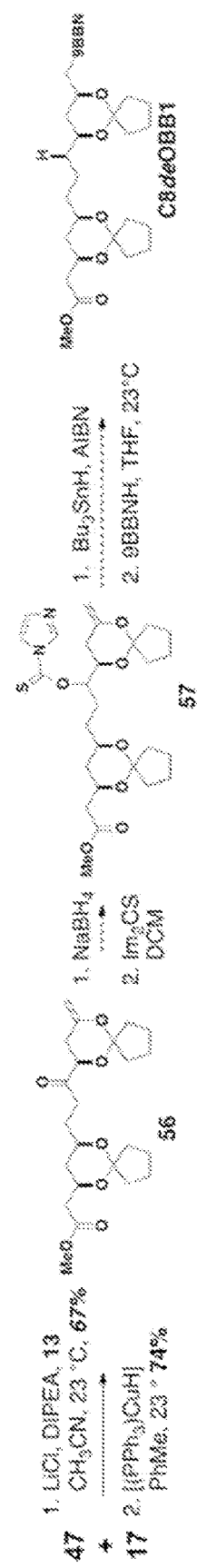
FIG. 27 depicts Scheme 15 in accordance with Example 4.

See Scheme 15, FIG. 27.

Similar to the strategy to access AmB, we envision the synthesis of C8-deoxy AmB arising from a total synthesis effort. To achieve this synthesis, the only change to the AmB synthesis that would need to be made is replacing C5deOBB1 with C8deOBB1. We envision the synthesis of C8deOBB1 arising from the reduction of alpha-beta unsaturated ketone 55, which would be accessed from a Horner-Wadsworth-Emmons coupling of aldehyde 47 and beta-keto phosphonate 17.

An HWE olefination between 47 and 17, followed by Stryker reduction of the resulting alpha-beta unsaturated carbonyl provides ketone 56. We then anticipate reducing the ketone to an alcohol with sodium borohydride and activating the alcohol for removal as thioester 57. Radical mediated removal of the C8-thioester is then achieved upon exposure to tributyltin hydride and AIBN. A hydroboration of the methylene dioxane with 9BBNH then readies C8deOAmB for entrance into the ICC sequence.

Figure 28:
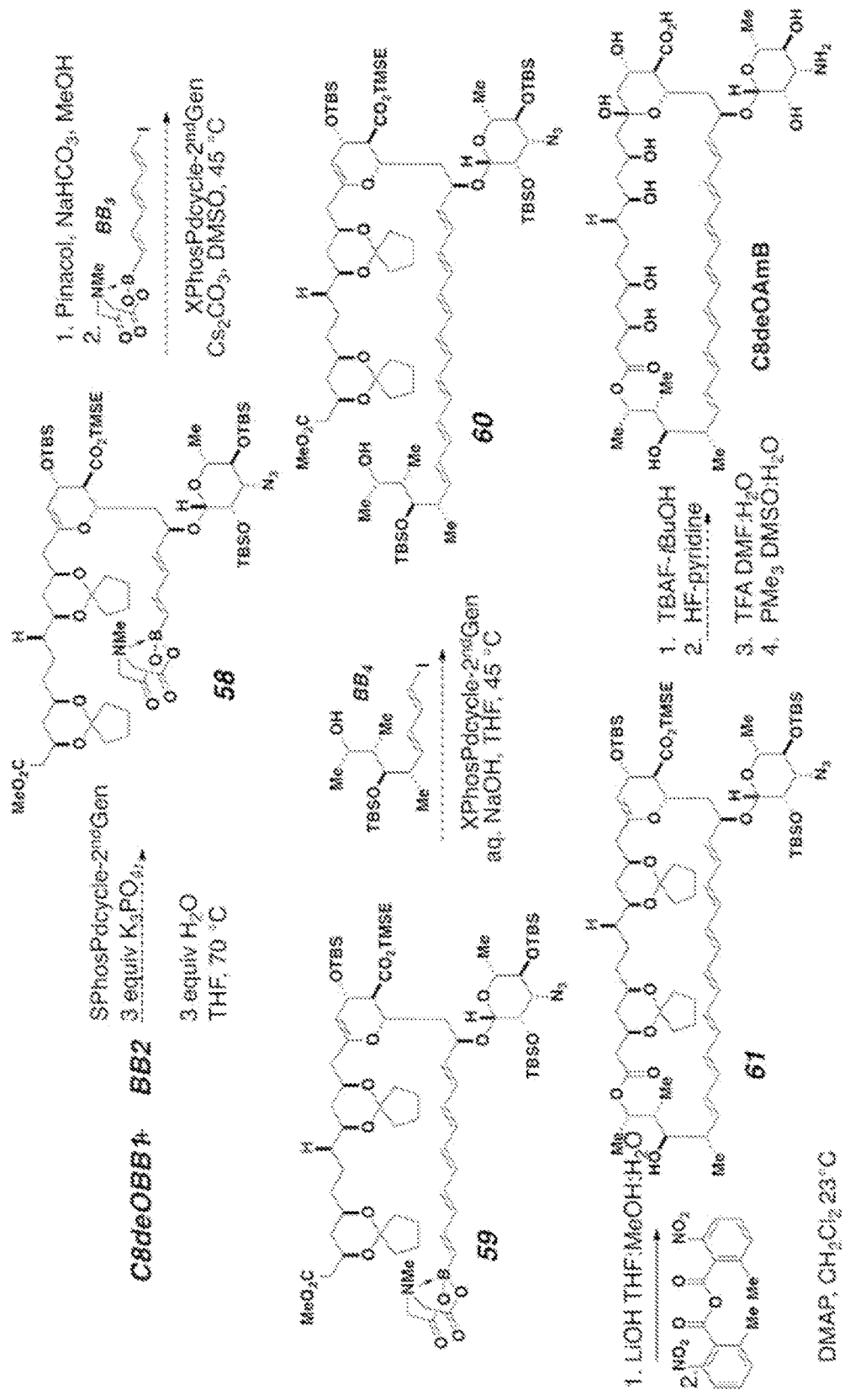
FIG. 28 depicts Scheme 16 in accordance with Example 4.

See Scheme 16, FIG. 28.

With all four building blocks in hand, they can now be assembled using the iterative cross coupling platform to rapidly generate with C8deOAmB macrolactone. We anticipate combination of C8deOBB1 and BB2 with Buchwald's $2^{nd}$ generation SPhos palladacycle, potassium phosphate, and 3 equivalents of water will effect a Suzuki-Miyaura cross coupling to form BB1-BB2 dimer 58. Pinacol exchange of the MIDA boronate, followed by a second Suzuki coupling with BB3, this time with the XPhos-Generation 2 palladacycle will form pentaene 59. An in-situ release of the MIDA boronate to a free boronic acid with sodium hydroxide in the presence of the palladium $2^{nd}$ generation XPhos palladacycle will form the all carbon linear framework of C8deOAmB 56. After saponification of methyl ester 60 with lithium hydroxide, a macrolactonization should then afford macrolactone 61. A series of protecting group removals including TMSE deprotection with TBAF-tBuOH complex, global desilylation with HF-pyridine, deketalization with trifluoroacetic acid, and Staudinger reduction of the C3' azide with trimethylphosphine should achieve the synthesis of C8deOAmB.

Example 5. C9-deoxy AmB

Total Synthesis of C9deOAmB

Figure 29:
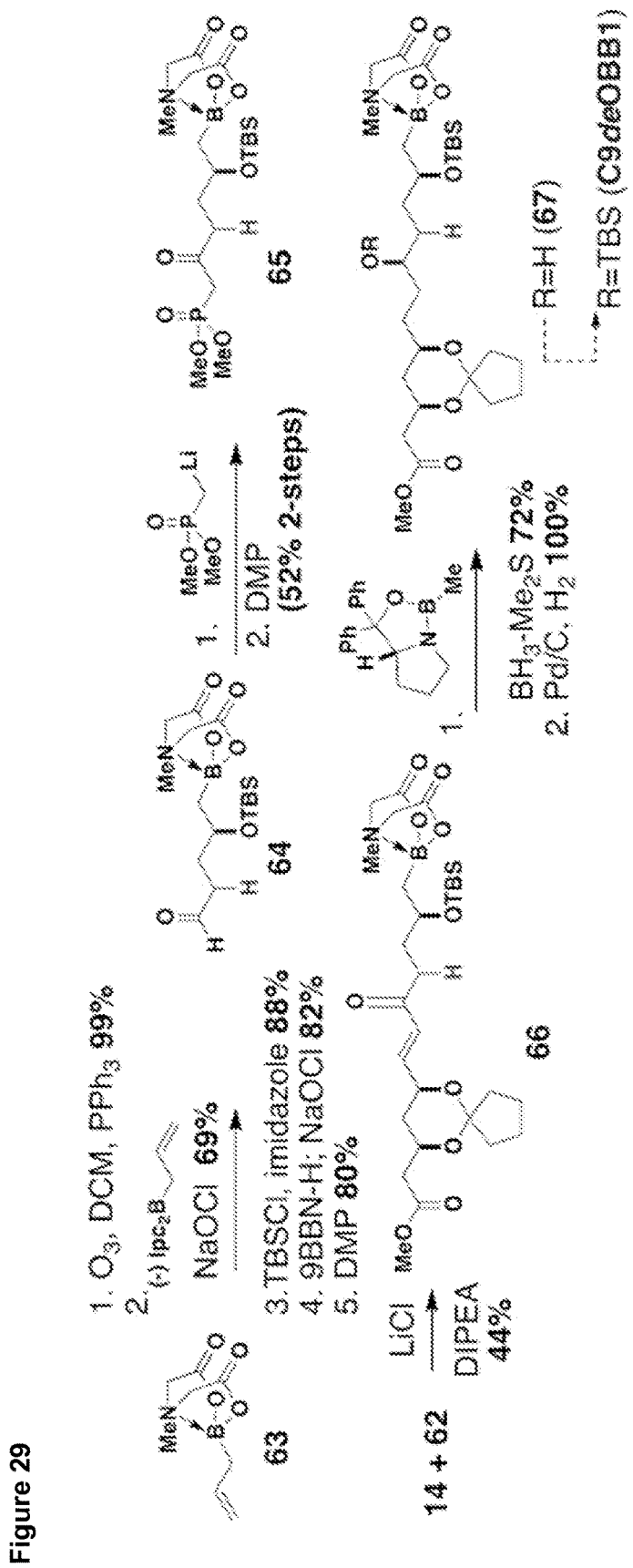
FIG. 29 depicts Scheme 17 in accordance with Example 5.

See Scheme 17, FIG. 29.

Similar to the strategy to access AmB, we envision the synthesis of C9-deoxy AmB arising from a total synthesis effort. To achieve this synthesis, the only change to the AmB synthetic strategy that would need to be made is replacing BB1 with C9deOBB1. We foresee the synthesis of C9deOBB1 arising from a Horner-Wadsworth-Emmons coupling of aldehyde 14 and beta-keto phosphonate 62. The C-11 stereocenter cannot be installed via a diastereoselective hydroboration, therefore to overcome this limitation, 9-deoxy BB1 was assembled stereoselectively in a linear fashion starting with a MIDA boronate. This route takes advantage of the ability of MIDA boronates to withstand a variety of common synthetic transformations.

Starting with allyl MIDA boronate 63, a short sequence of ozonolysis, Brown allylation, TBS protection, and hydroboration/oxidation results in aldehyde 64. During this initial sequence it was discovered that a bleach, instead of the typical hydrogen peroxide/sodium hydroxide, oxidative workup of the initial brown allylation product efficiently oxidizes the carbon-boron bond without decomposition of the MIDA boronate. Exposure of 64 to lithiated dimethyl methyl phosphonate followed by Dess-Martin oxidation yields β-keto phosphonate 65. Demonstrating the convergent nature of the BB1 synthetic strategy, combination of 14 with 62 in a Horner-Wadsworth-Emmons coupling affords α-β unsaturated ester 66. Reduction of the carbonyl with the (R)—CBS catalyst, followed by catalytic hydrogenation yields 67. This C-9 deoxy BB1 intermediate contains the entire carbon framework in the correct oxidation state with all of the stereochemistry preinstalled. Only a TBS protection is required to realize a C-9 deoxy BB1 analog ready for MIDA boronate deprotection and coupling with BB2.

Figure 30:
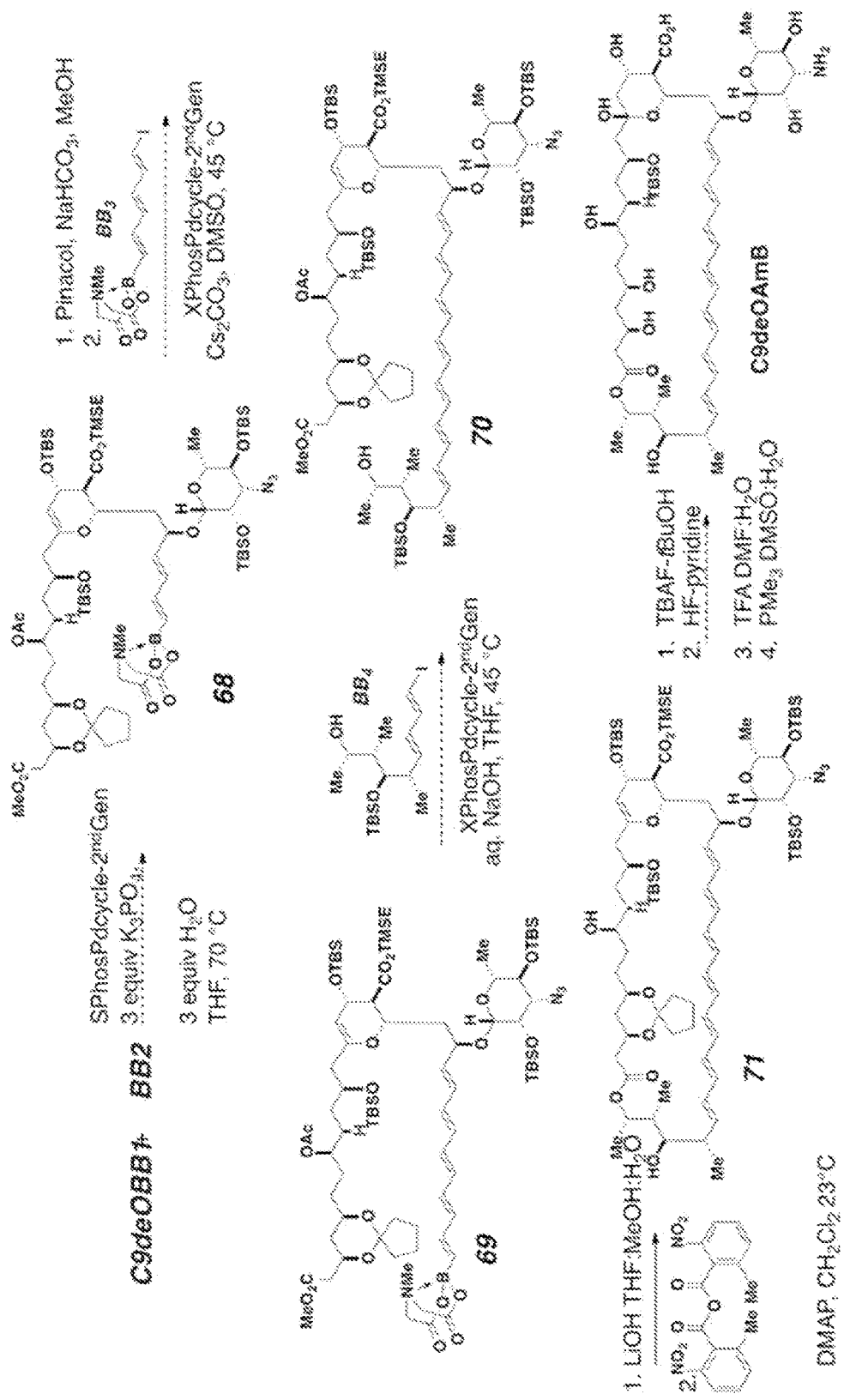
FIG. 30 depicts Scheme 18 in accordance with Example 5.

See Scheme 18, FIG. 30.

With all four building blocks in hand, they can now be assembled using the iterative cross coupling platform to rapidly generate with C9deOAmB macrolactone. We anticipate combination of C9deOAmB, after MIDA boronate hydrolysis with NaOH, and BB2 with Buchwald's $2^{nd}$ generation SPhos palladacycle, potassium phosphate, and 3 equivalents of water will effect a Suzuki-Miyaura cross coupling to form BB1-BB2 dimer 68. Pinacol exchange of the MIDA boronate, followed by a second Suzuki coupling with BB3, this time with the XPhos-Generation 2 palladacycle will form pentaene 69. An in-situ release of the MIDA boronate to a free boronic acid with sodium hydroxide in the presence of the palladium $2^{nd}$ generation XPhos palladacycle will form the all carbon linear framework of C9deOAmB 70. After saponification of methyl ester 70 with lithium hydroxide, a macrolactonization should then afford macrolactone 71. A series of protecting group removals including TMSE deprotection with TBAF-tBuOH complex, global desilylation with HF-pyridine, deketalization with trifluoroacetic acid, and Staudinger reduction of the C3' azide with trimethylphosphine should achieve the synthesis of C9deOAmB.

Example 6. C11-deoxy AmB

Total Synthesis of C11deOAmB

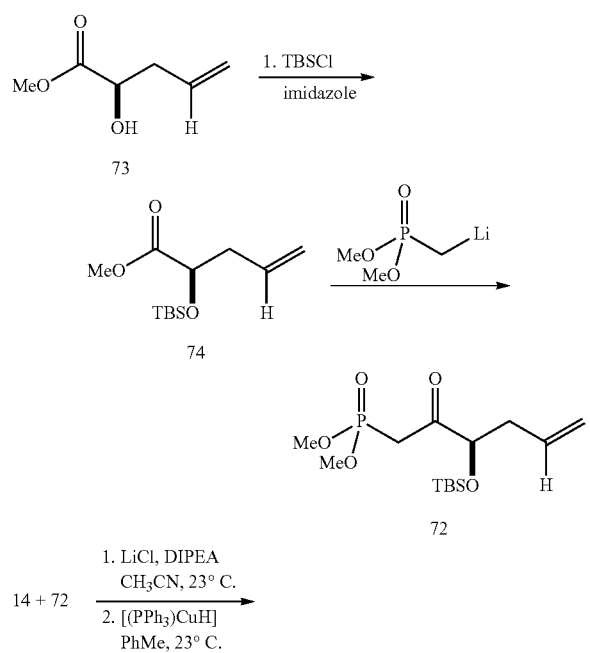

Scheme 19

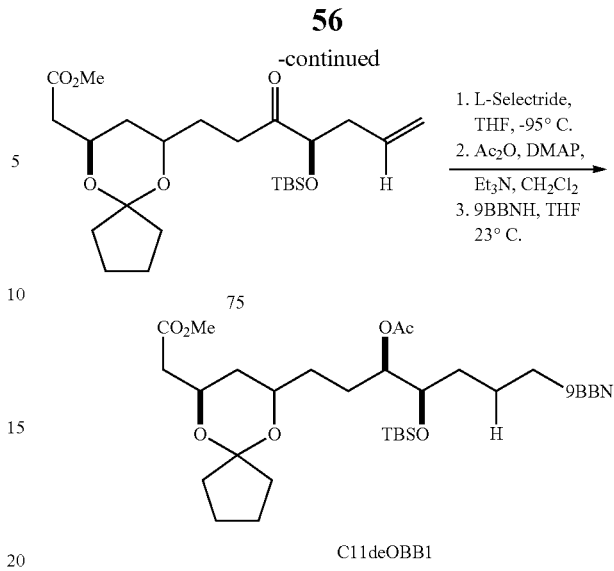

C11deOBB1

Similar to the strategy to access AmB, we envision the synthesis of C8-deoxy AmB arising from a total synthesis effort. To achieve this synthesis, the only change to the AmB synthesis that would need to be made is replacing BB1 with C11deOBB1. We envision the synthesis of C11deOBB1 arising from a Horner-Wadsworth-Emmons coupling of aldehyde 14 and beta-keto phosphonate 72.

We envision the synthesis of C11deOBB1 starting with the TBS silylation of alpha-hydroxy ester 73. Addition of lithiated dimethyl methyl phosphonate 17 into this ester should provide beta-keto phosphonate 72. Under Horner-Wadsworth-Emmons coupling conditions, 72 should react with aldehyde 14. Subsequent reduction of the generated alpha-beta unsaturated carbonyl with Stryker's reagent should provide ketone 75. A diastereoselective ketone reduction resulting from exposure of 75 to L-Selectride, followed by acylation of the resulting alcohol, and hydroboration of the methylene dioxane readies C11deOAmB for Suzuki-Miyaura cross coupling with BB2.

Figure 31:
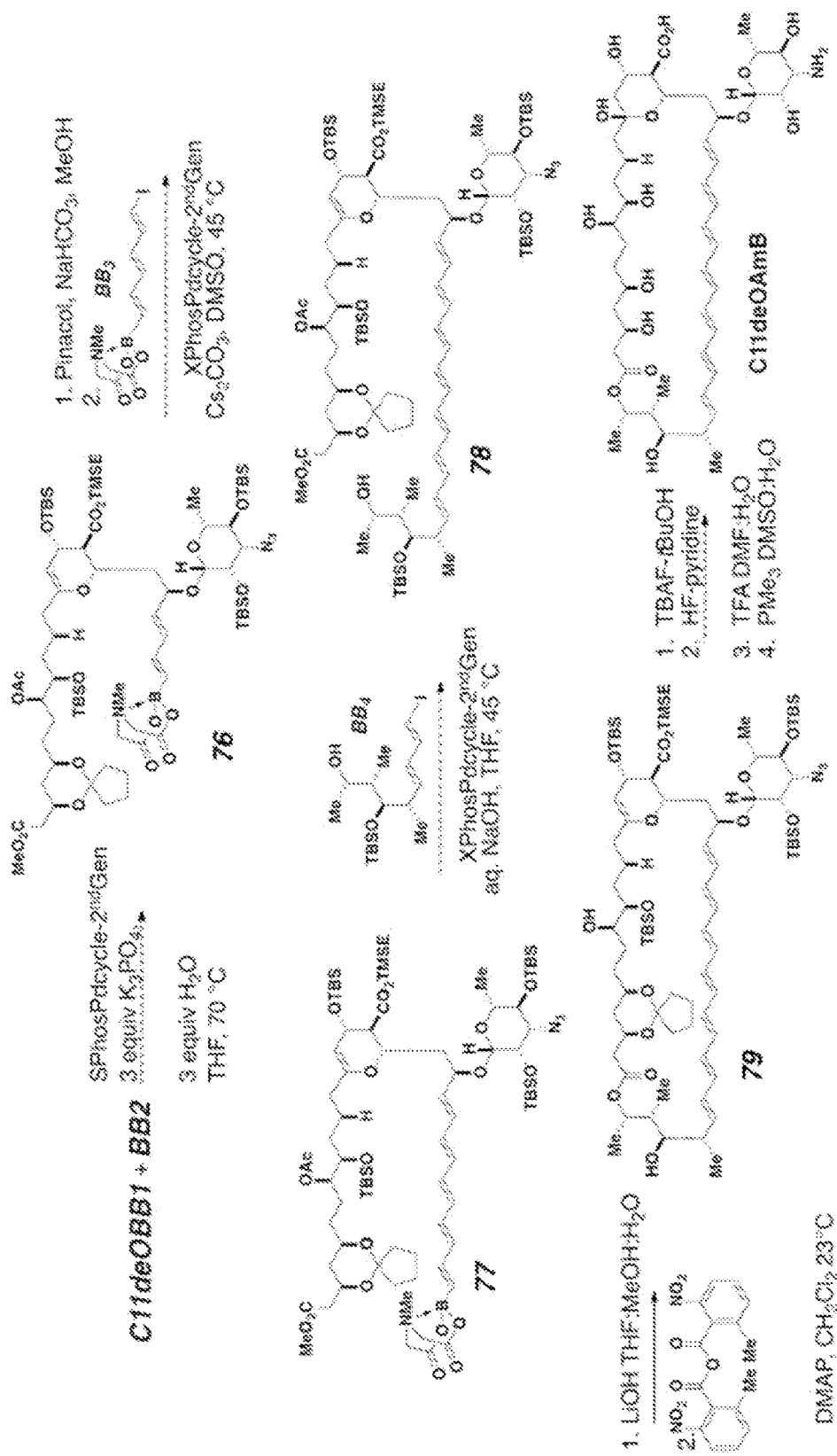
FIG. 31 depicts Scheme 20 in accordance with Example 6.

See Scheme 20, FIG. 31.

With all four building blocks in hand, they can now be assembled using the iterative cross coupling platform to rapidly generate with C11deOAmB macrolactone. We anticipate combination of C11deOBB1 and BB2 with Buchwald's $2^{nd}$ generation SPhos palladacycle, potassium phosphate, and 3 equivalents of water will effect a Suzuki-Miyaura cross coupling to form BB1-BB2 dimer 76. Pinacol exchange of the MIDA boronate, followed by a second Suzuki coupling with BB3, this time with the XPhos-Generation 2 palladacycle will form pentaene 77. An in-situ release of the MIDA boronate to a free boronic acid with sodium hydroxide in the presence of the palladium $2^{nd}$ generation XPhos palladacycle will form the all carbon linear framework of C11deOAmB 78. After saponification of methyl ester 78 with lithium hydroxide, a macrolactonization should then afford macrolactone 79. A series of protecting group removals including TMSE deprotection with TBAF-tBuOH complex, global desilylation with HF-pyridine, deketalization with trifluoroacetic acid, and Staudinger reduction of the C3' azide with trimethylphosphine should achieve the synthesis of C11deOAmB.

Example 7. C13-deoxy AmB

Figure 32:
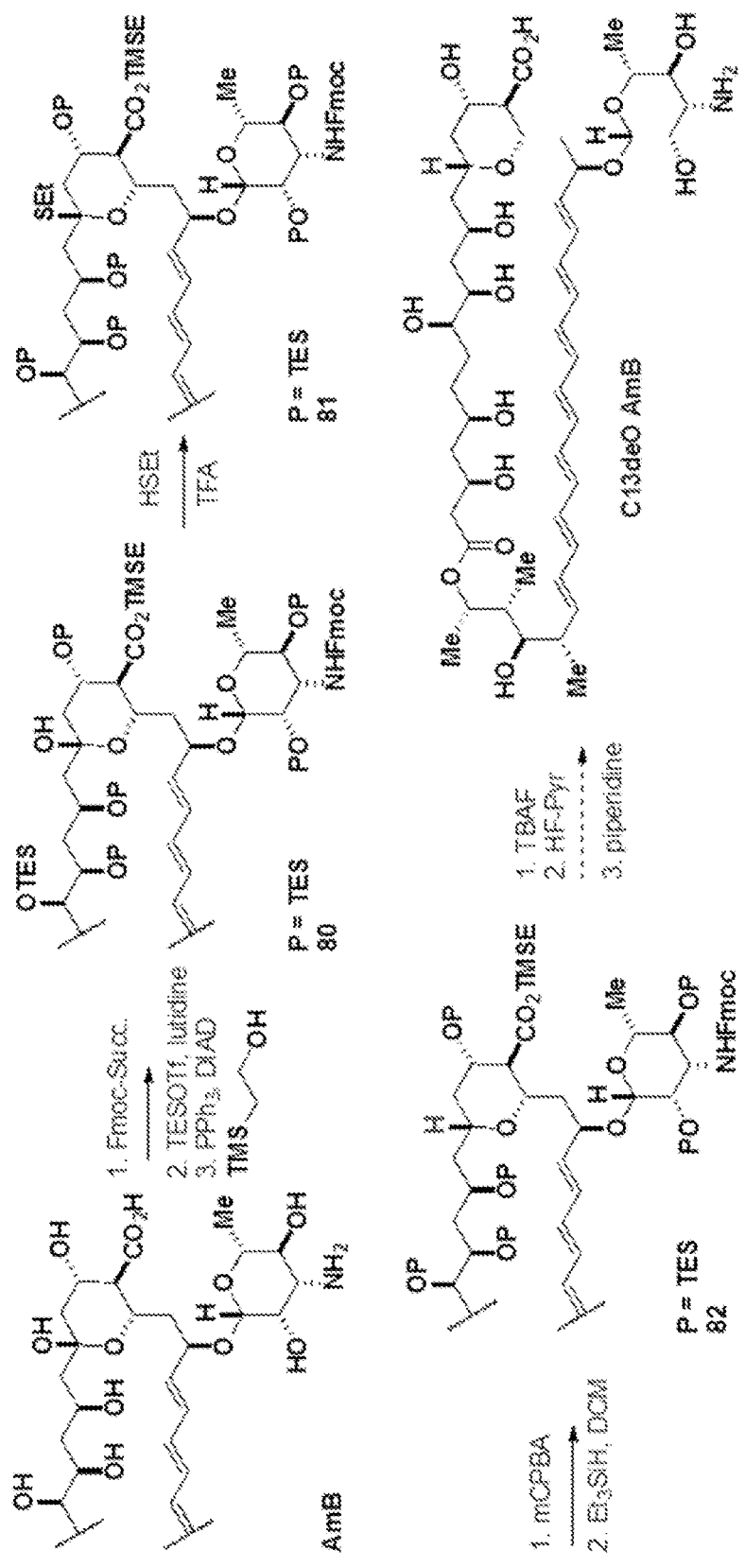
FIG. 32 depicts Scheme 21 in accordance with Example 7.

Total Synthesis of C13deOAmB
See Scheme 21, FIG. 32.

Figure 11:
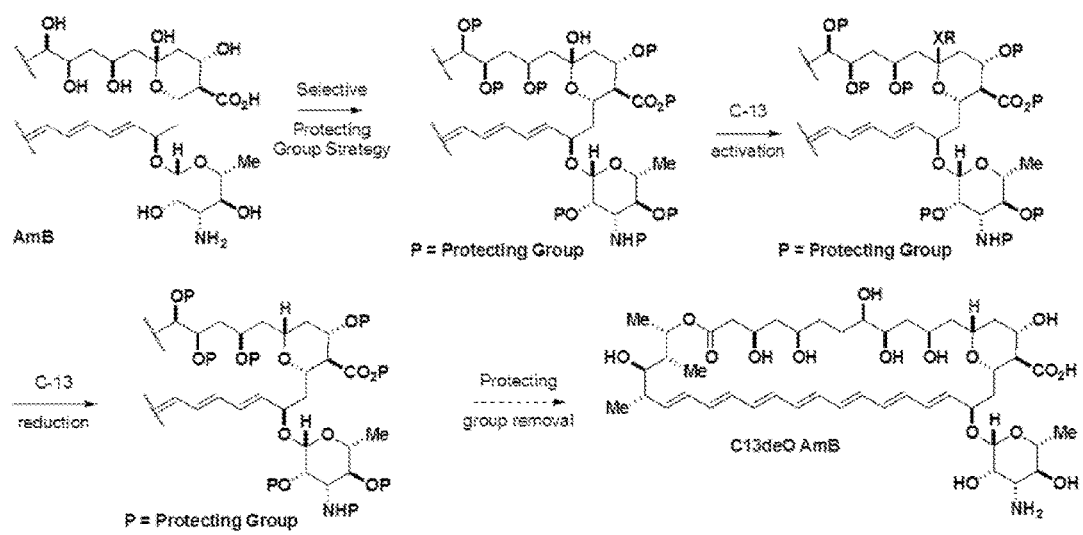
FIG. 11 depicts a degradative strategy to synthesize of C13deOAmb.
Figure 12:
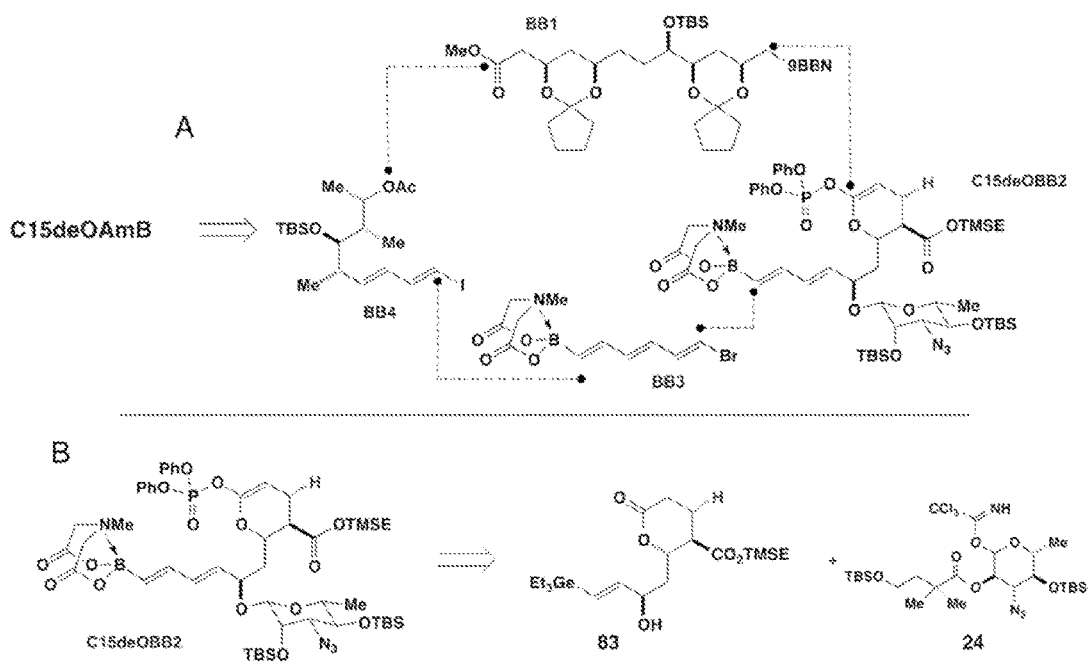
FIG. 12 depicts an iterative cross-coupling-based strategy for synthesis of C15 deOAmB.

One approach to the synthesis of C13deOAmB is presented in FIG. 11. Upon generating a suitably protected intermediate the C-13 alcohol can be activated for reduction either through conversation to another ketal, thioketal, or elimination to a C-13,C-14 dihydropyran. Upon activation of the C-13 alcohol, it could then be reduced to a simple hydrogen atom. Then a series of protecting group removals would complete the synthesis of C13 deOAmB.

The synthesis of C13deOAmB commences with Fmoc protection of the mycosamine nitrogen, persilylation of all alcohols except the C13 ketal as TES silyl ethers, and finally a Misunobu installation of the TMSE ester to provide fully protected intermediate 80. Then, the C-13 position is easily converted with ethane thiol and acid to ethyl thioketal 81. Oxidation of 81 with mCPBA provides a sulfoxide which could be removed under reductive conditions with triethylsilane in DCM. With 82 in hand, a series of protecting group removals including TMSE removal with tetrabutylammonium fluoride, global TES desilylation with HF-pyridine complex, and a final Fmoc deprotection with piperidine could grant access to C13deOAmB.

Example 8. C15-deoxy AmB

Figure 33:
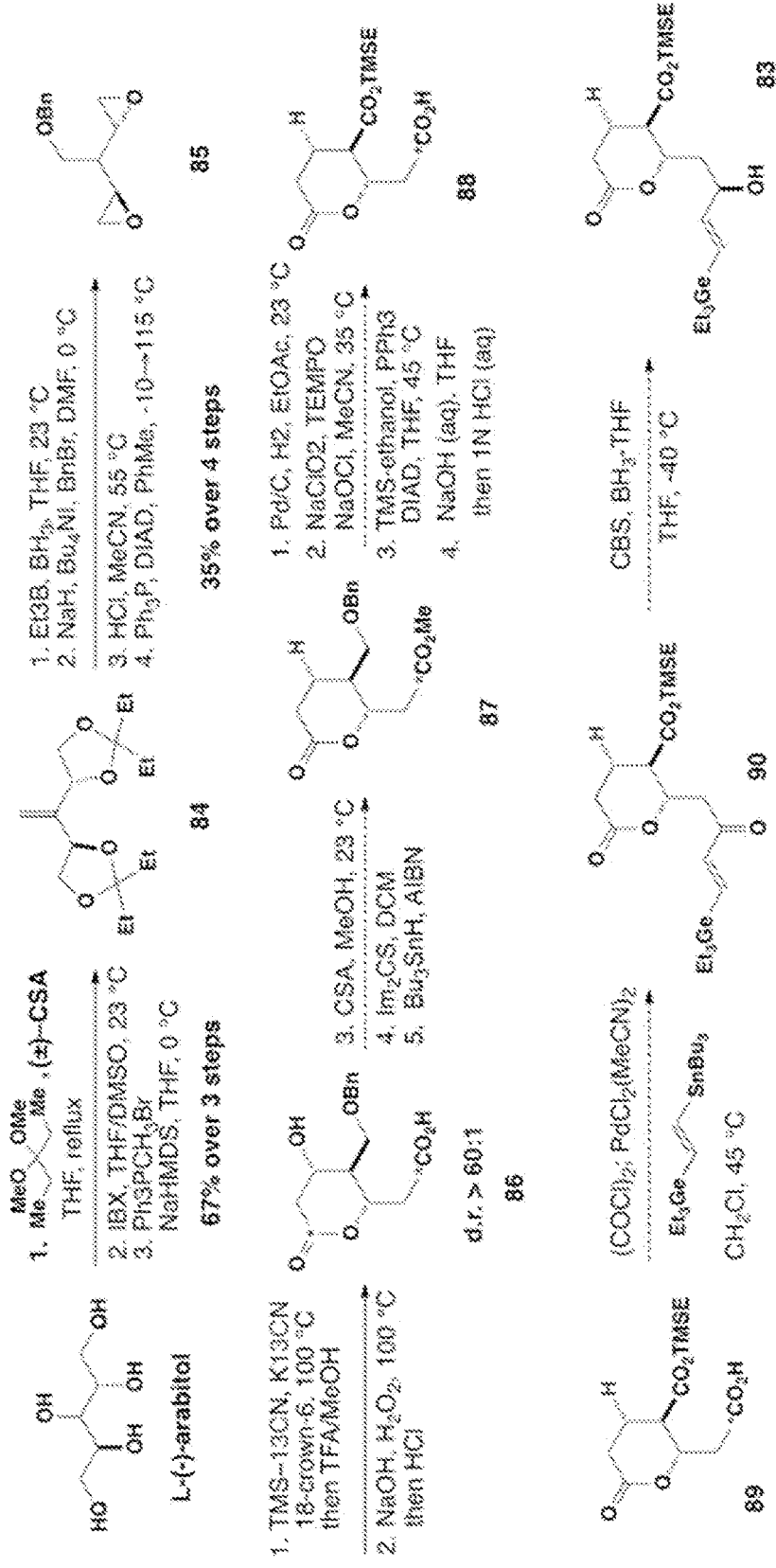
FIG. 33 depicts Scheme 22 in accordance with Example 8.

Total Synthesis of C15deOAmB
See Scheme 22, FIG. 33.

Similar to the strategy to access AmB, we envision the synthesis of C15-deoxy AmB arising from a total synthesis effort. To achieve this synthesis, the only change to the AmB synthetic strategy that would need to be made is replacing BB2 with C15deOAmB. We foresee the synthesis of C15deOBB1 arising from the glycosylation of allylic alcohol 83, lacking the C15 alcohol, with a mycosamine sugar donor 24.

The synthesis of allylic alcohol 83 begins L-(-)-arabitol and proceeds through the same synthetic sequence as BB2 all the way through the diastereotopic group selective lactonization generating lactone 86. From this branching point, methyl esterification, followed by activating the C15-alcohol for removal as the thiocarbonyl, and resulting Barton-McCombie type deoxygenation promoted by tributyltin hydride and AIBN should provide deoxygenated lactone 87.

With lactone 87 in hand, debenzylation, upon exposure of 87 to palladium on carbon and hydrogen, followed by Pinnick oxidation, and then Mitsunobu reaction with TMS-ethanol should provide a differentially substituted di-ester capable of selective saponification with sodium hydroxide to provide acid 88. Acid chloride formation of 88 with oxalyl chloride followed by Stille coupling with bismetalated olefin should provide alpha-beta unsaturated ketone 90. Diastereoselective reduction of ketone 90 to allylic alcohol 83 could be achieved with a CBS reduction ready for glycosylation with 24. Taking advantage of the anchimeric assistance platform for controlled beta-glycosylation, combination of 83 and 24 in the presence of buffered chloro-methyl pyridinium triflate should provide 91 with excellent beta selectivity. The TDMB directing group could then be removed upon exposure to CSA in hexafluoroisopropanol, tert-butanol, and methylene chloride revealing free alcohol 92. A three step sequence of oxidation, reduction of the resulting ketone and silylation should access TBS ether 93. Iododegermylation followed exposure to diphenyl phosphoryl chloride and LiHMDS could access to ketene acetal phosphonate 95. A selective Stille coupling to a tributyl stannane should achieve the synthesis of C15 deOBB2.

Figure 34:
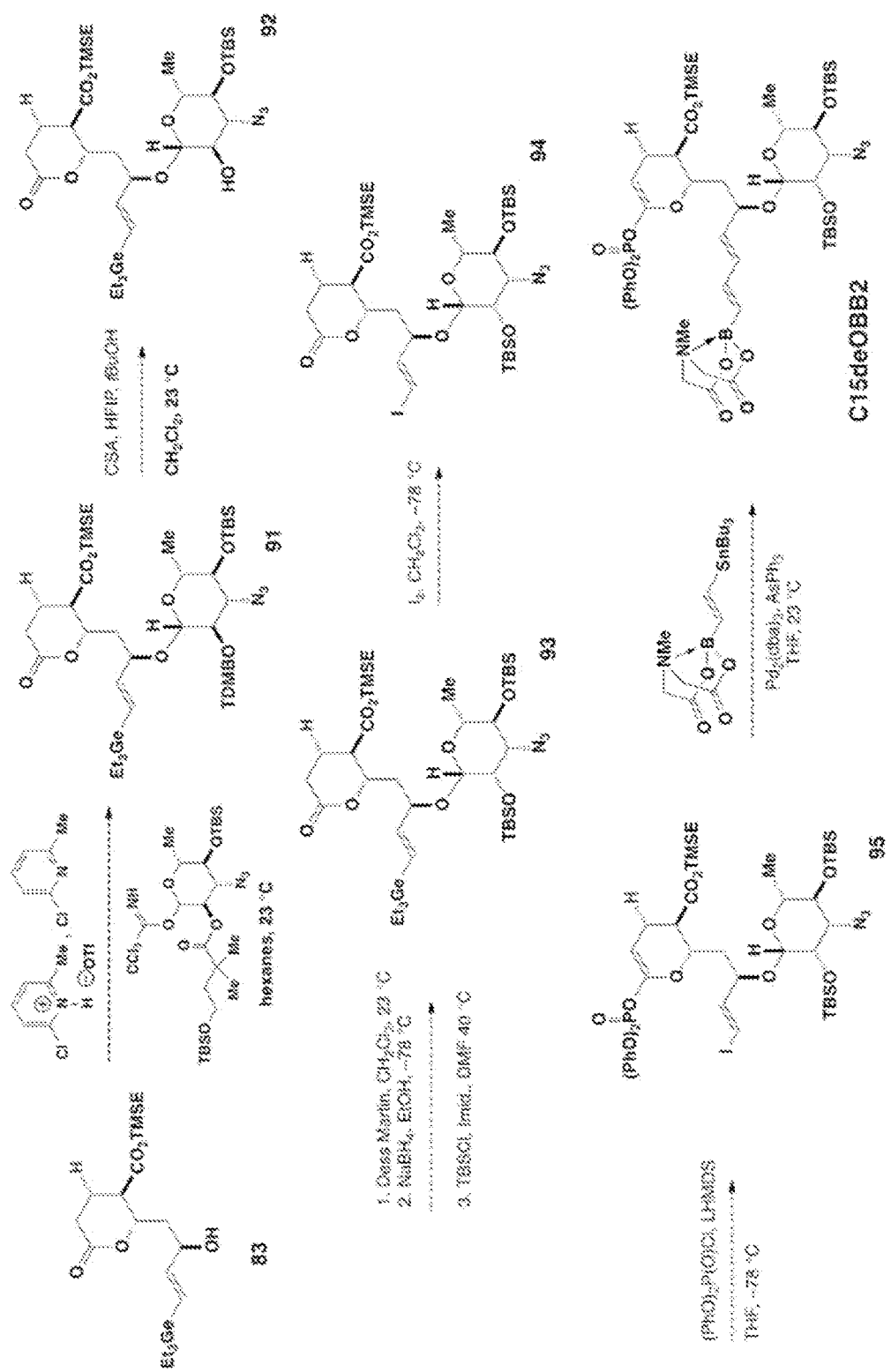
FIG. 34 depicts Scheme 23 in accordance with Example 8.
Figure 35:
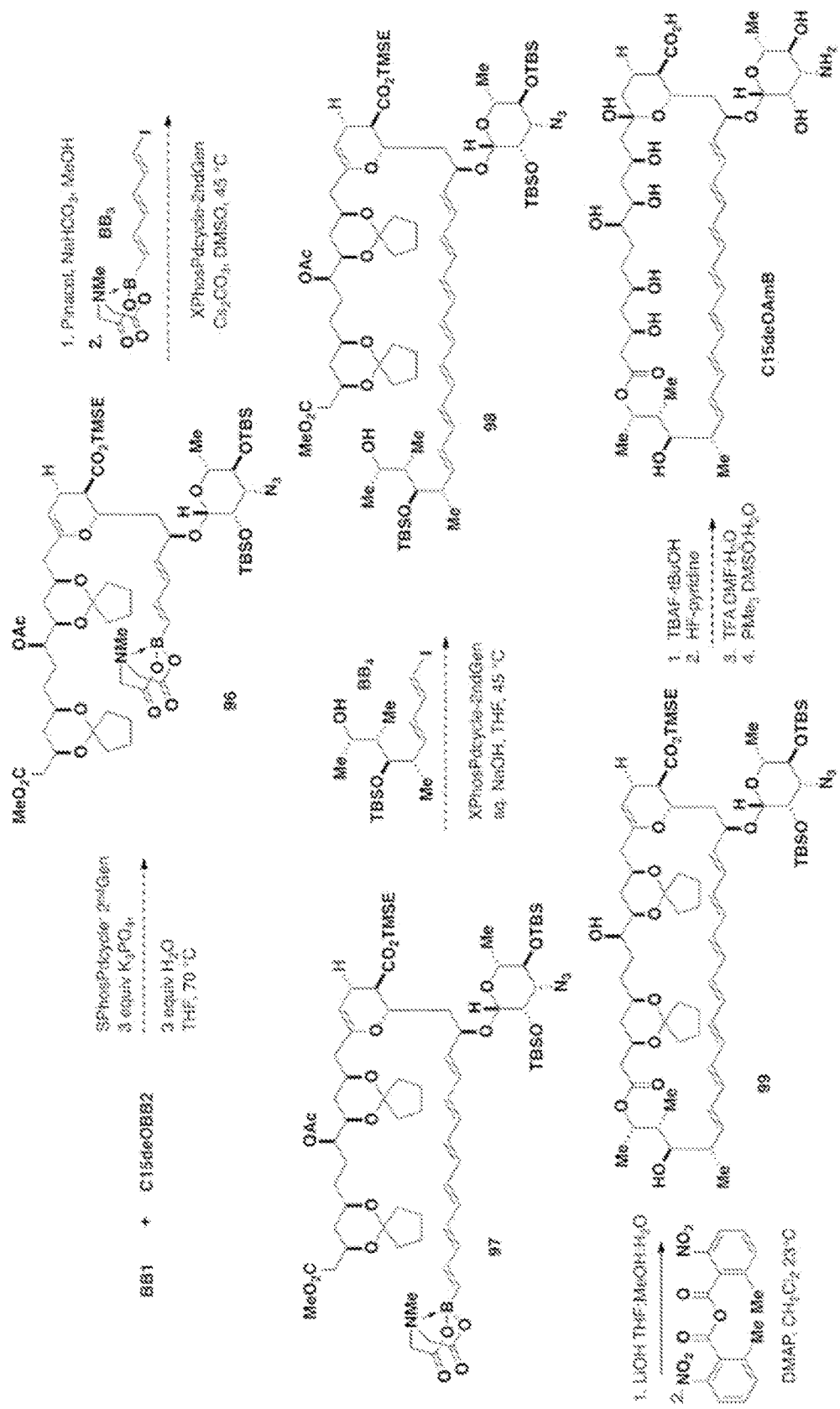
FIG. 35 depicts Scheme 24 in accordance with Example 8.

See Scheme 23, FIG. 34; and Scheme 24, FIG. 35.

With all four building blocks in hand, they can now be assembled using the iterative cross coupling platform to rapidly generate with C15deOAmB macrolactone. We anticipate combination of BB1 and C15deOBB2 with Buchwald's $2^{nd}$ generation SPhos palladacylce, potassium phosphate, and 3 equivalents of water will effect a Suzuki-Miyaura cross coupling to form BB1-BB2 dimer 96. Pinacol exchange of the MIDA boronate, followed by a second Suzuki coupling with BB3, this time with the XPhos-Generation 2 palladacycle will form pentaene 97. An in-situ release of the MIDA boronate to a free boronic acid with sodium hydroxide in the presence of the palladium $2^{nd}$ generation XPhos palladacycle will form the all carbon linear framework of C15deOAmB 98. After saponification of methyl ester 98 with lithium hydroxide, a macrolactonization should then afford macrolactone 99. A series of protecting group removals including TMSE deprotection with TBAF-tBuOH complex, global desilylation with HF-pyridine, deketalization with trifluoroacetic acid, and Staudinger reduction of the C3' azide with trimethylphosphine should achieve the synthesis of C15deOAmB.

Example 9. C15-deoxy AmB

Figure 36:
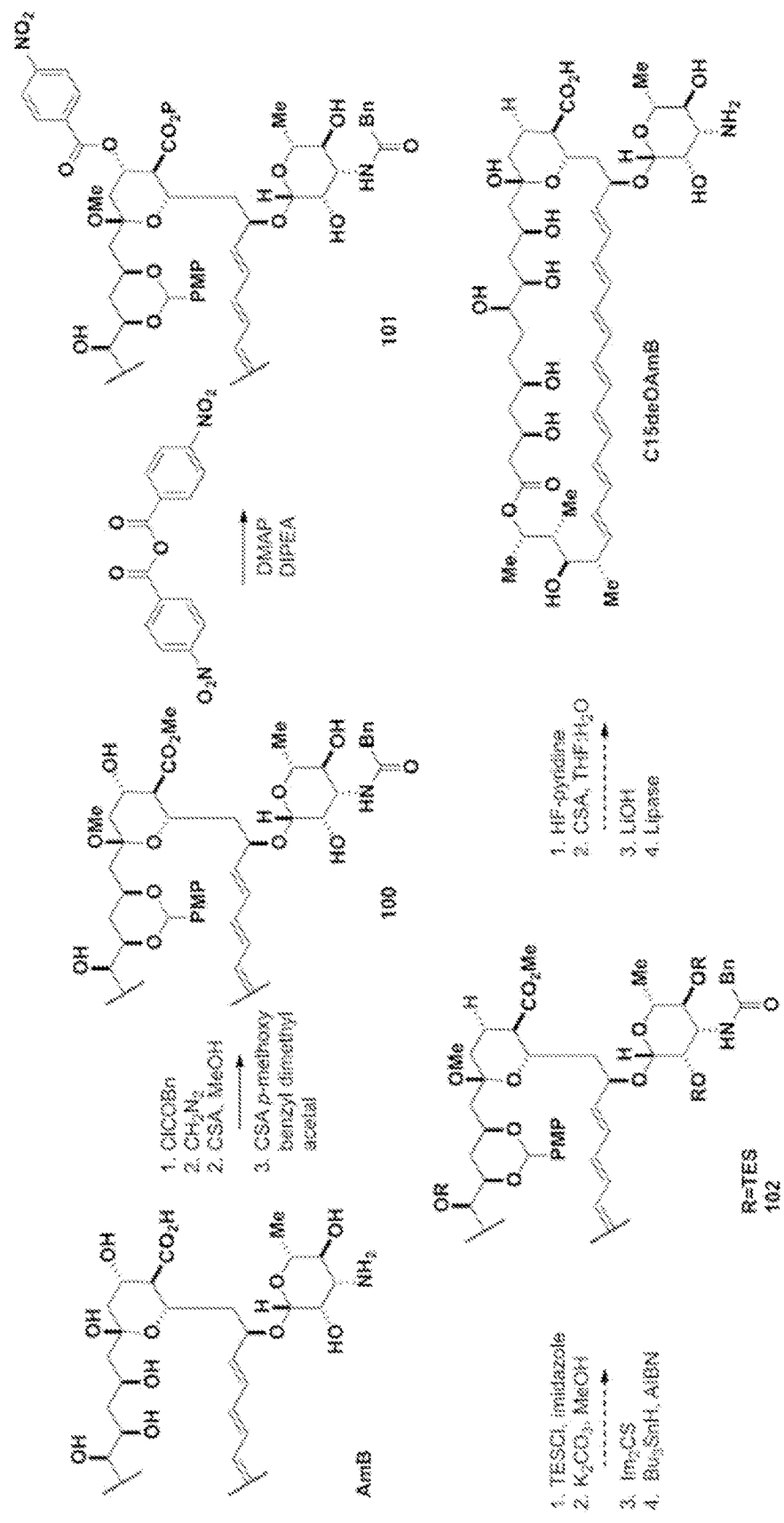
FIG. 36 depicts Scheme 25 in accordance with Example 9.

Selective Acylation
See Scheme 25, FIG. 36.

Figure 13:
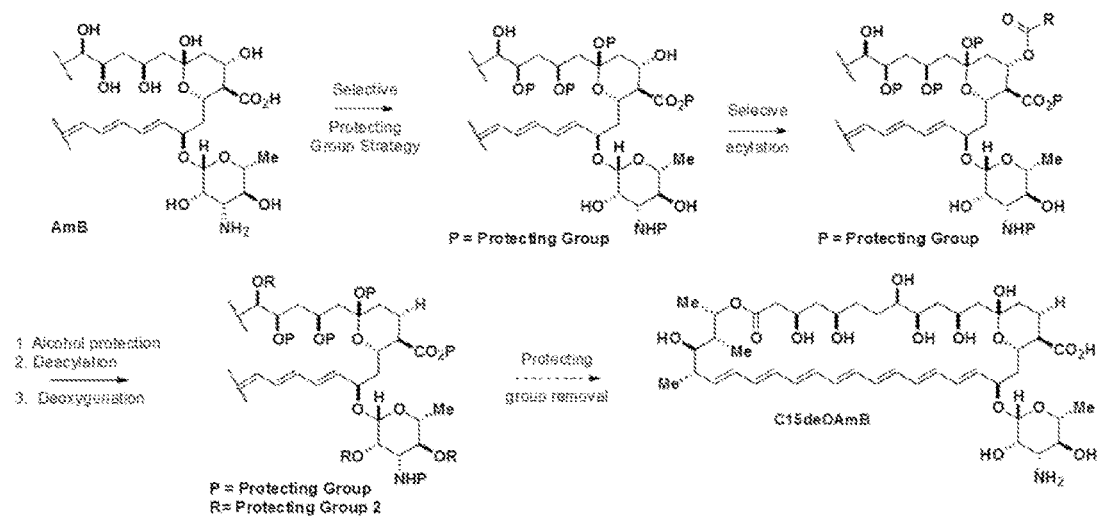
FIG. 13 depicts a selective acylation strategy for synthesis of C15deOAmB.
Figure 14:
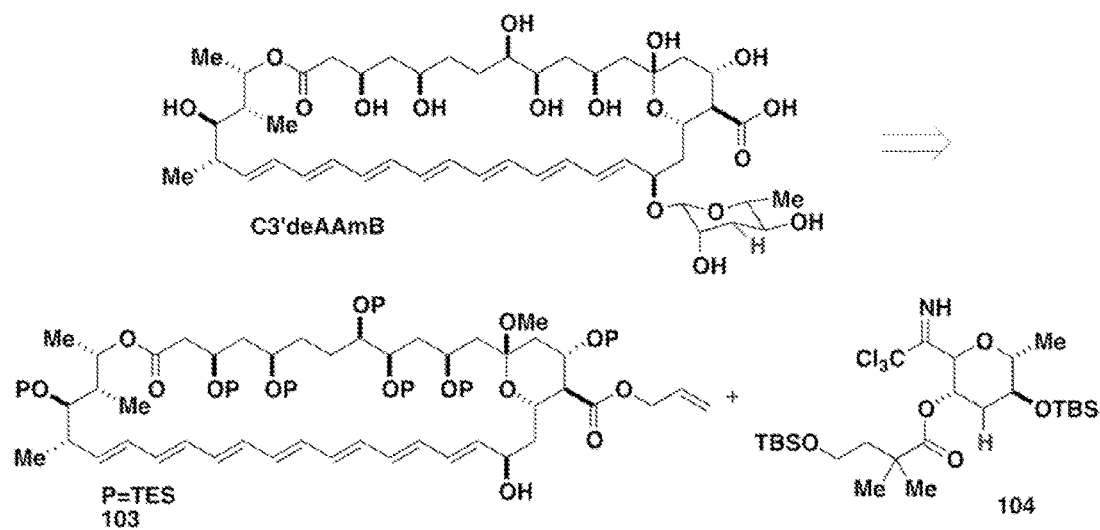
FIG. 14 depicts a scheme for synthesis of C3'-deamino AmB (C3'deAAmB) using a hybrid glycosidation strategy.
Figure 15:
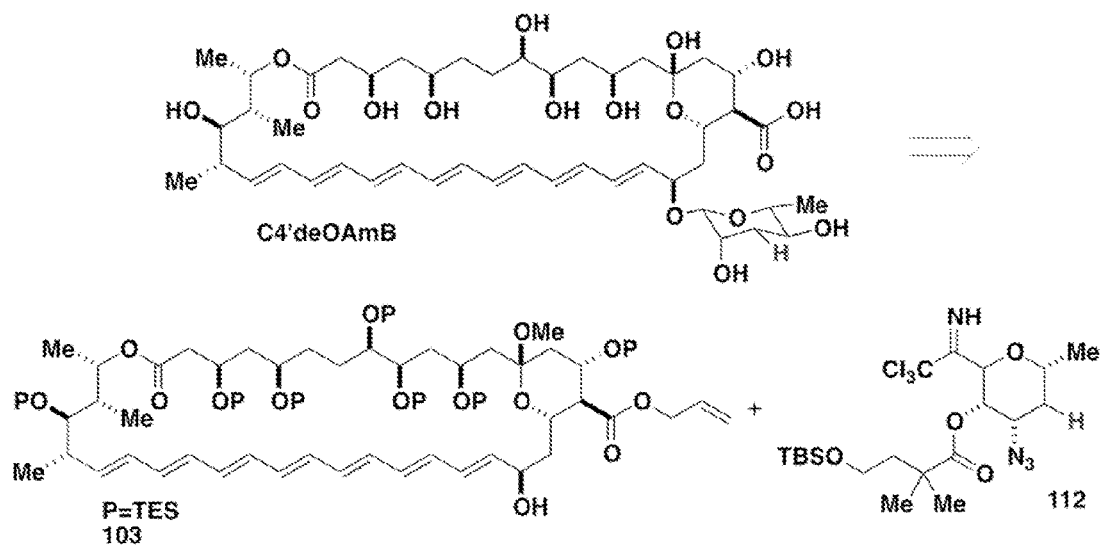
FIG. 15 depicts a scheme for synthesis of C4'deOAmB via a hybrid glycosylation strategy.

A second strategy which could arrive at C15deOAmB is outlined in FIG. 13. Upon producing a suitably protected intermediate, a selective acylation reaction could provide solely a C15 acyl derivative. With this differentially protected alcohol in hand, protection of the remaining alcohols, followed by deacylation and deoxygenation of the now free C-15 alcohol could arrive at an intermediate which is only a series of deprotections away from C15deOAmB.

As shown in Scheme 25, starting with AmB a series of protecting group manipulations including phenyl acyl formation, methyl ketal formation, methyl esterification using diazomethane, and selective acetal formation of both the C,3-C,5 diol and the C,9-C,11 diol as p-methoxy benzyl acetals arrives at suitably protected intermediate 100. Acylation of 100 with p-nitro phenyl anhydride catalyzed by DMAP selectively acylates the C-15 position. With this differentially protected alcohol 101 in hand, a sequence of persilylation of the remaining alcohols, followed by deacylation, activation of the now free C-15 alcohol as a thiocarbonyl, and radical deoxygenation promoted by tributyltin hydride and AIBN should arrive at intermediate 102. A final deprotection sequence of removal of the TES groups with HF-pyridine, followed by CSA catalyzed ketal hydrolysis, methyl ester saponification with lithium hydroxide, and final enzymatic deacylation should provide access to C15deOAmB.

Example 10. C3'-deamino AmB

Figure 37:
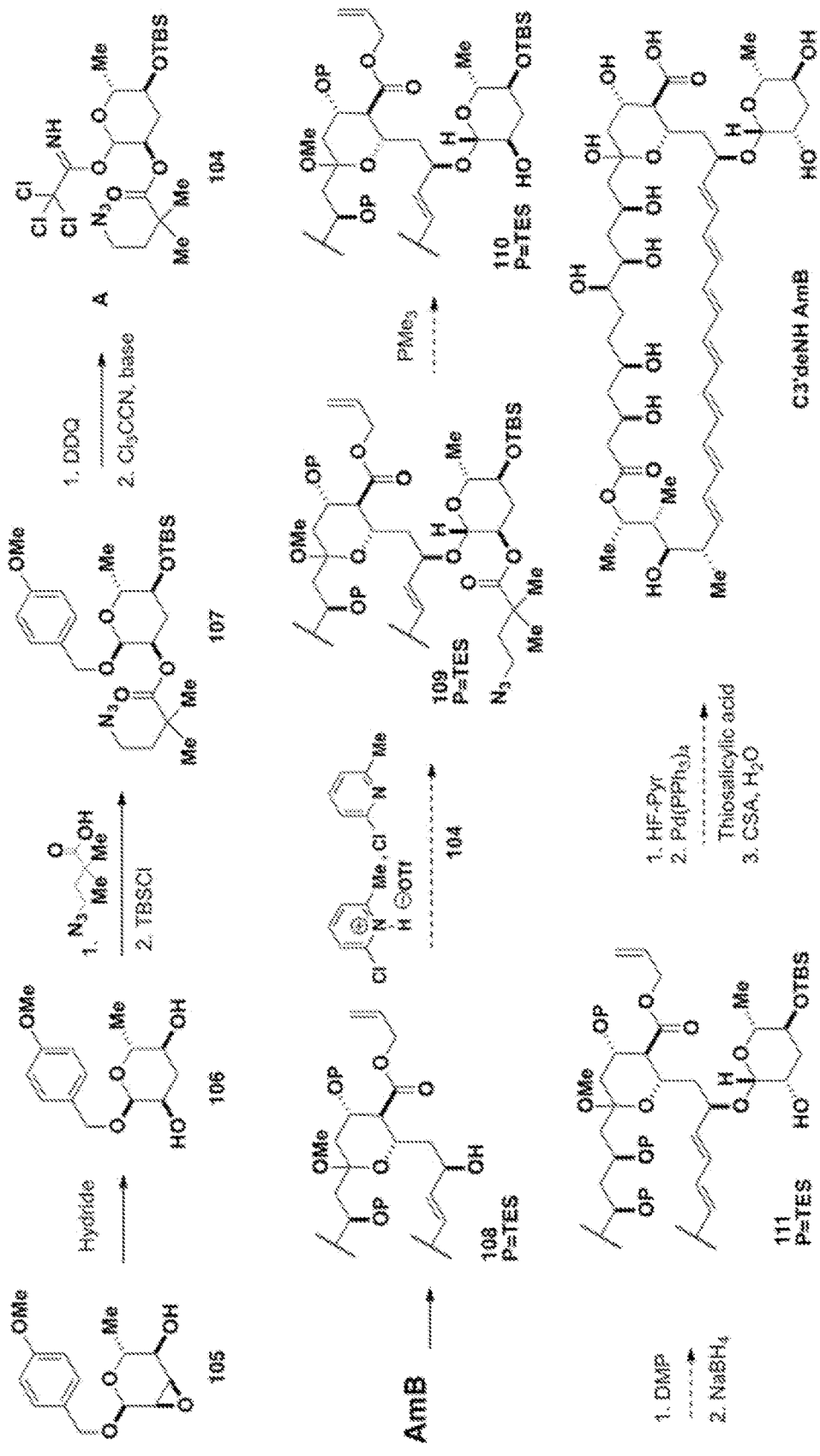
FIG. 37 depicts Scheme 26 in accordance with Example 10.

Hybrid Synthesis
See Scheme 26, FIG. 37.

The synthesis of C3'deAAmB is grounded on the glycosylation of amphoternolide 103 strategy utilized in the synthesis of C2'deoxyAmB by our group previously. Wilcock, B C et al., *J Am Chem Soc* 135:8488 (2013). We anticipate glycosylating 103 with deamino sugar donor 104 to achieve the full carbon framework of C3'deaminoAmB.

Subsequent protecting group removal should provide efficient access to this derivative.

The synthesis of 104 begins with PMB ether 105, accessible from 2-furyl methyl ketone as outlined in Scheme 8. Opening of epoxide 105 with a hydride selectively generates C2' alcohol 106. Introduction of the ZDMB directing group using EDC and DMAP, followed by TBS silylation of the remaining alcohol provides pyran 107. DDQ removal of the PMB protecting group and exchange for a trichloroacetimidate generates C3'deamino sugar donor 104. With 104 in hand, we anticipate glycosylation to proceed with exceptional beta selectivity under buffered chloro-methyl pyridinium triflate conditions to provide 109. We then expect the ZDMB directing group to be removed under Staudinger conditions with trimethylphosphine. An oxidation, reduction sequence of alcohol 110 would then invert the stereochemistry at C2' and provide alcohol 111. A deprotection sequence of desilylation with HF-pyridine, allyl ester removal with Pd(PPh$_3$)$_4$, and thiosalicylic acid, and methyl ketal hydrolysis CSA in water and dimethylsulfoxide (DMSO) should provide access to C3'deAAmB.

Example 11. C4'-deoxy AmB

Figure 38:
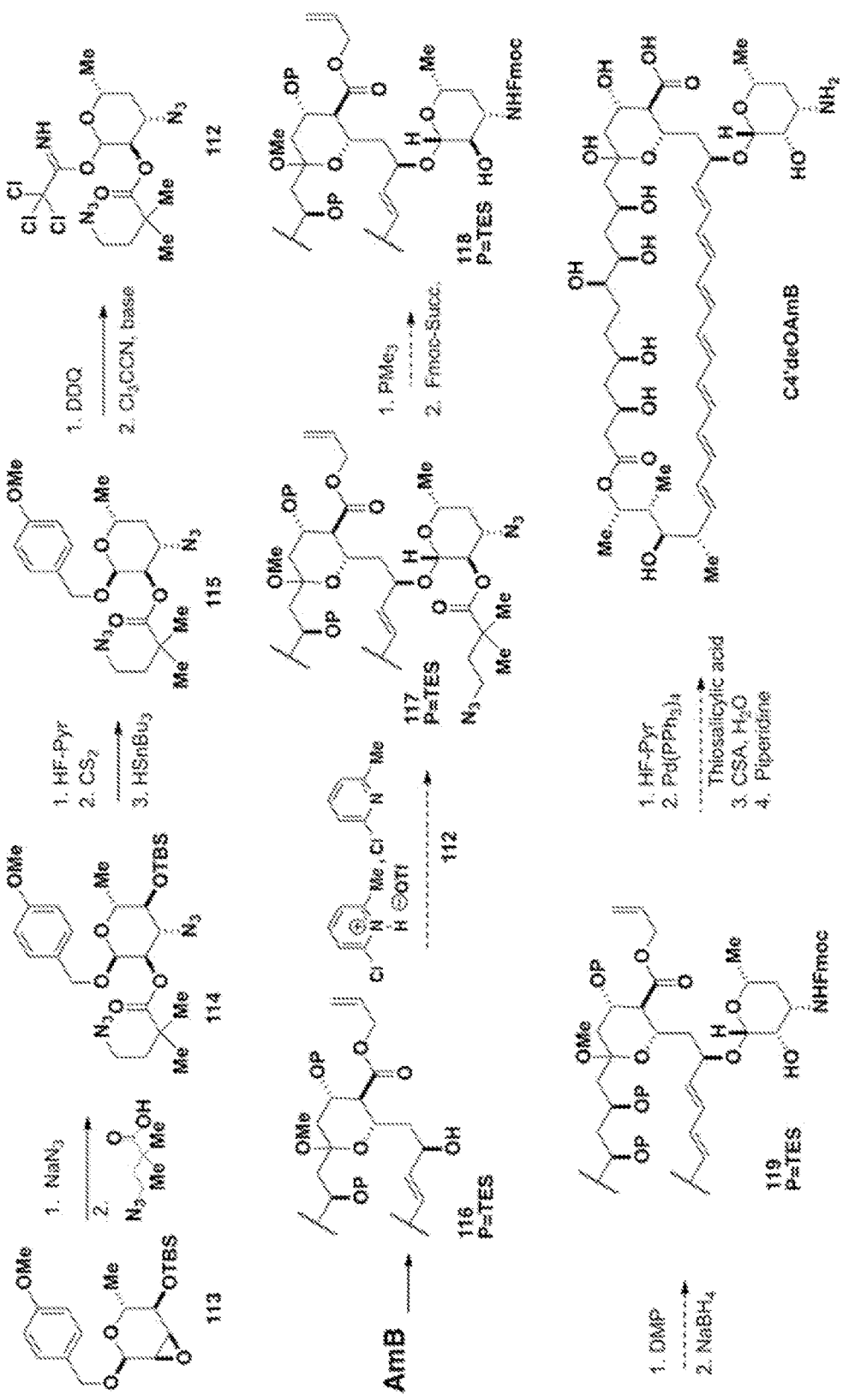
FIG. 38 depicts Scheme 27 in accordance with Example 11.

Hybrid Synthesis
See Scheme 27, FIG. 38.

The synthesis of C4'deOAmB is grounded on the glycosylation of amphoternolide 103 strategy utilized in the synthesis of C2'deoxyAmB by our group previously. Wilcock, B C et al., *J Am Chem Soc* 135:8488 (2013). We anticipate glycosylating 103 with deoxygenated sugar donor 112 to achieve the full carbon framework of C4'deoxyAmB. Subsequent protecting group removal should provide efficient access to this derivative.

The synthesis of 112 begins with PMB ether 113, accessible from 2-furyl methyl ketone as outlined in Scheme 8. Epoxide 113 is efficiently opened with sodium azide, followed by introduction of the ZDMB directing group using EDC and DMAP generating TBS ether 114. We then anticipate desilylation upon treatment with HF providing a free alcohol at C4'. The C4' alcohol could then be removed after a two-step procedure of activation to a thiocarbonyl, followed by radical deoxygenation with tributyltin hydride and AIBN to afford azide 115. DDQ removal of the PMB protecting group and exchange for a trichloroacetimidate would then generate C4'deoxy sugar donor 112. With 112 in hand, we anticipate glycosylation to proceed with exception beta selectivity under buffered chloro-methyl pyridinium triflate conditions to provide 117. We then expect the ZDMB directing group to be removed under Staudinger conditions with trimethylphosphine with concomitant reduction of the C3' azide to an amine. Reprotection with Fmoc-succinimide would then provide alcohol 118. An oxidation, reduction sequence of alcohol # would then invert the stereochemistry at C2' and provide alcohol 119. A deprotection sequence of desilylation with HF-pyridine, allyl ester removal with Pd(PPh$_3$)$_4$, and thiosalicylic acid, and methyl ketal hydrolysis CSA in water and dimethylsulfoxide (DMSO) should provide access to C4'deOAmB.

Example 12. In Vitro Assessment of Biological Activity

Each derivative proposed herein is tested for biological activity against both yeast and human cells to determine its therapeutic index. A broth microdilution experiment determines the MIC (minimum inhibitory concentration) of each derivative against *S. cerevisiae* and the clinically relevant *C. albicans*, thereby establishing the antifungal activity of each novel derivative. To test for toxicity against human cells, each compound is exposed to a hemolysis assay against red blood cells which determines the concentration required to cause 90% lysis of human red blood cells (EH$_{90}$). Additionally, each compound is exposed to human primary renal tubule cells to determine the toxicity of each compound against kidney cells. These assays when compared against the known values of AmB against the same cell lines determine the improvement in therapeutic index of each compound.

Example 13. In Vivo Assessment of Biological Activity

Figure 39:
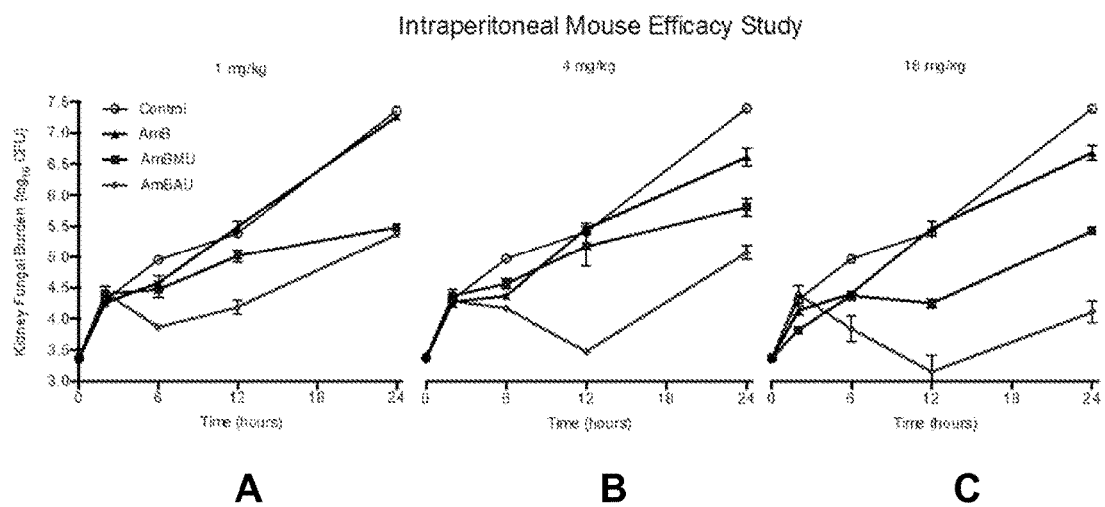
FIG. 39 is a group of three graphs depicting kidney fungal load (colony forming units, cfu) in neutropenic mice inoculated intravenously with C. albicans and then treated two hours later with a single intraperitoneal dose of vehicle control, AmB, AmBMU, or AmBAU.

The antifungal efficacies of AmBMU and AmBAU were tested in a mouse model of disseminated candidiasis. In this experiment neutropenic mice were infected with *C. albicans* via the tail vein, and then 2 hours post infection the mice were treated with a single intraperitoneal injection of AmB, AmBMU, or AmBAU. Then 2, 6, 12, and 24 hours post infection the mice were sacrificed, and the fungal burden present in their kidneys was quantified. Results are shown in FIG. 39. Both AmBMU and AmBAU were substantially more effective than AmB at reducing the fungal burden present in the kidneys at all three tested doses (i.e., 1, 4, and 16 mg/kg). The differences were most pronounced at the 16 mg/kg dose at 24 hours post inoculation. Relative to AmB, AmBMU reduced the fungal burden by 1.2 log units ($p \leq 0.001$), and AmBAU reduced the fungal burden by nearly 3 log units ($p \leq 0.0001$). We speculate that an improved pharmacological profile, potentially due to greatly increased water solubility, may contribute to the unexpected and dramatic improvements in in vivo antifungal activity for the new compounds.

Figure 40:
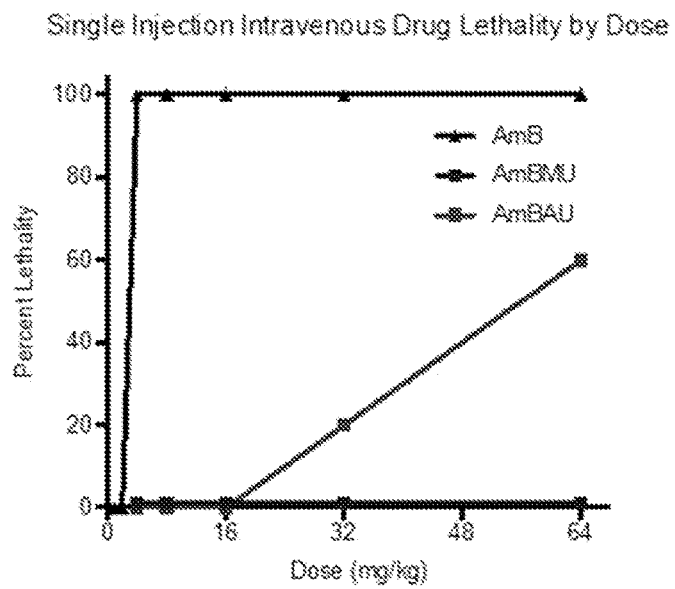
FIG. 40 is a graph depicting lethality in healthy mice of single intravenous administration in the doses indicated of AmB, AmBMU, or AmBAU.

In a separate set of experiments, acute toxicity was evaluated by single intravenous administration of 1, 2, 4, 8, 16, 32, or 64 mg/kg AmB or its derivatives to healthy mice, followed by monitoring for lethality. Results are shown in FIG. 40. All mice in the 4 mg/kg AmB dosage group died within seconds. AmBAU was drastically less toxic with >50% lethality not being reached until the 64 mg/kg dosage group. Strikingly, all mice dosed with 64 mg/kg AmBMU survived with no observable toxicity.

REFERENCES

[1] a) D. Ellis, *Journal of Antimicrobial Chemotherapy* 2002, 49, 7; b) J. R. Rees, R. W. Pinner, R. A. Hajjeh, M. E. Brandt, A. L. Reingold, *Clinical Infectious Diseases* 1998, 27, 1138; c) L. R. Asmundsdottir, H. Erlendsdottir, M. Gottfredsson, *Journal of Clinical Microbiology* 2002, 40, 3489.

[2] a) P. Eggimann, J. Garbino, D. Pittet, *Lancet Infectious Diseases* 2003, 3, 772; b) C. A. Martin, *Journal of Pharmacy Practice* 2005, 18, 9; c) M. M. McNeil, S. L. Nash, R. A. Hajjeh, M. A. Phelan, L. A. Conn, B. D. Plikaytis, D. W. Warnock, *Clinical Infectious Diseases* 2001, 33, 641; d) R. D. Cannon, E. Lamping, A. R. Holmes, K. Niimi, K. Tanabe, M. Niimi, B. C. Monk, *Microbiology-Sgm* 2007, 153, 3211; e) S. J. Howard, I. Webster, C. B. Moore, R. E. Gardiner, S. Park, D. S. Perlin, D. W. Denning, *International Journal of Antimicrobial Agents* 2006, 28, 450.

[3] a) M. A. Pfaller, D. J. Diekema, A. L. Colombo, C. Kibbler, K. P. Ng, D. L. Gibbs, V. A. Newell, *Journal of*

Clinical Microbiology 2006, 44, 3578; b) M. Hakki, J. F. Staab, M. A. Man, *Antimicrobial Agents and Chemotherapy* 2006, 50, 2522; c) K. Barker, P. Rogers, *Current Infectious Disease Reports* 2006, 8, 449.

[4] G. Deray, *Journal of Antimicrobial Chemotherapy* 2002, 49, 37.

[5] J. Mora-Duarte, R. Betts, C. Rotstein, A. L. Colombo, L. Thompson-Moya, J. Smietana, R. Lupinacci, C. Sable, N. Kartsonis, J. Perfect, C. I. C. S, *New England Journal of Medicine* 2002, 347, 2020.

[6] T. J. Walsh, R. W. Finberg, C. Arndt, J. Hiemenz, C. Schwartz, D. Bodensteiner, P.

Pappas, N. Seibel, R. N. Greenberg, S. Dummer, M. Schuster, J. S. Holcenberg, N. I. A. I. D. M. S. Grp, *New England Journal of Medicine* 1999, 340, 764.

[7] a) P. J. Cagnoni, T. J. Walsh, M. M. Prendergast, D. Bodensteiner, M. Hiemenz, R. N. Greenberg, C. A. S. Arndt, M. Schuster, N. Seibel, V. Yeldandi, K. B. Tong, *Journal of Clinical Oncology* 2000, 18, 2476; b) H. W. Murray, *American Journal of Tropical Medicine and Hygiene* 2004, 71, 787.

[8] A. Wong-Beringer, R. A. Jacobs, B. J. Guglielmo, *Clinical Infectious Diseases* 1998, 27, 603.

[9] a) B. C. Monk, A. Goffeau, *Science* 2008, 321, 367; b) J. Bolard, *Biochimica Et Biophysica Acta* 1986, 864, 257.

[10] a) G. R. Keim, P. L. Sibley, Y. H. Yoon, J. S. Kulesza, I. H. Zaidi, M. M. Miller, J. W. Poutsiaka, *Antimicrobial Agents and Chemotherapy* 1976, 10, 687; b) W. G. Ellis, R. A. Sobel, S. L. Nielsen, *The Journal of Infectious Diseases* 1982, 146, 125; c) M. Cheron, B. Cybulska, J. Mazerski, J. Grzybowska, A. Czerwinski, E. Borowski, *Biochemical Pharmacology* 1988, 37, 827; d) M. J. Driver, A. R. Greenlees, D. T. MacPherson, *Journal of the Chemical Society, Perkin Transactions 1* 1992, 3155; e) M. Slisz, B. Cybulska, J. Mazerski, J. Grzybowska, E. Borowski, *The Journal of Antibiotics* 2004, 57, 669; f) A. M. Szpilman, D. M. Cereghetti, J. M. Manthorpe, N. R. Wurtz, E. M. Carreira, *Chemistry—A European Journal* 2009, 15, 7117; g) A. Finkelstein, R. Holz, *Aqueous pores created in thin lipid membranes by the polyene antibiotics nystatin and AmB membranes. Lipid Bilayers and Antibiotics*, Dekker, New York, 1973; h) T. E. Andreoli, *Annals of the New York Academy of Sciences* 1974, 235, 448; i) B. De Kruijff, W. J. Gerritsen, A. Oerlemans, R. A. Demel, L. L. M. van Deenen, *Biochimica et Biophysica Acta (BBA)—Biomembranes* 1974, 339, 30; j) M. Baginski, H. Resat, E. Borowski, *Biochimica et Biophysica Acta (BBA)—Biomembranes* 2002, 1567, 63; k) D. M. Cereghetti, E. M. Carreira, *Synthesis* 2006, 6, 914; l) R. Zietse, R. Zoutendijk, E. J. Hoorn, *Nat Rev Nephrol* 2009, 5, 193.

[11] K. C. Gray, D. S. Palacios, I. Dailey, M. M. Endo, B. E. Uno, B. C. Wilcock, M. D. Burke, *Proceedings of the National Academy of Sciences of the United States of America* 2012, 109, 2234.

[13] a) K. C. Duggan, D. J. Hermanson, J. Musee, J. J. Prusakiewicz, J. L. Scheib, B. D. Carter, S. Banerjee, J. A. Oates, L. J. Marnett, *Nature Chemical Biology* 2011, 7, 803; b) I. J. Letourneau, A. J. Slot, R. G. Deeley, S. P. C. Cole, *Drug Metabolism and Disposition* 2007, 35, 1372; c) K. Koike, C. J. Oleschuk, A. Haimeur, S. L. Olsen, R. G. Deeley, S. P. C. Cole, *Journal of Biological Chemistry* 2002, 277, 49495; d) B. S. Hendriks, K. M. Seidl, J. R. Chabot, *Bmc Systems Biology* 2010, 4; e) Z. A. Knight, K. M. Shokat, *Chemistry & Biology* 2005, 12, 621; OW. Davidson, L. Frego, G. W. Peet, R. R. Kroe, M. E. Labadia, S. M. Lukas, R. J. Snow, S. Jakes, C. A. Grygon, C. Pargellis, B. G. Werneburg, *Biochemistry* 2004, 43, 11658; g) M. Neant-Fery, R. D. Garcia-Ordonez, T. P. Logan, D. J. Selkoe, L. Li, L. Reinstatler, M. A. Leissring, *Proceedings of the National Academy of Sciences of the United States of America* 2008, 105, 9582.

[14] a) P. Ganis, Avitabil. G, Mechlins. W, Schaffne. Cp, *Journal of the American Chemical Society* 1971, 93, 4560; b) K. N. Jarzembska, D. Kaminski, A. A. Hoser, M. Malinska, B. Senczyna, K. Wozniak, M. Gagos, *Crystal Growth & Design* 2012, 12, 2336.

[15] a) W. Mechlinski, C. Schaffner, P., *The Journal of Antibiotics* 1972, 25, 256; b) L. Falkowski, A. Jarzebski, B. Stefanka, E. Bylec, E. Borowski, *The Journal of Antibiotics* 1980, 33, 103; c) D. T. MacPherson, D. F. Corbett, B. C. Costello, M. J. Driver, A. R. Greenlees, W. S. Maclachlan, C. T. Shanks, A. W. Taylor, *Recent advances in the chemistry of anti-infective agents*, Royal Society of Chemistry, 1993; d) D. Corbett, F., D. K. Dean, A. R. Greenlees, D. T. MacPherson, *The Journal of Antibiotics* 1995, 48, 509; e) D. S. Palacios, T. M. Anderson, M. D. Burke, *Journal of the American Chemical Society* 2007, 129, 13804; f) D. S. Palacios, I. Dailey, D. M. Siebert, B. C. Wilcock, M. D. Burke, *Proceedings of the National Academy of Sciences* 2011, 108, 6733.

[16] H. Maeda, M. Suzuki, H. Sugano, K. Matsumoto, *Synthesis* 1988, 5, 401.

[17] Y. Ichikawa, Y. Matsukawa, M. Isobe, *Journal of the American Chemical Society* 2006, 128, 3934.

[18] D. S. Palacios, University of Illinois at Urbana-Champaign (Urbana, Ill.), 2011.

[19] a) V. Paquet, E. M. Carreira, *Organic Letters* 2006, 8, 1807; b) V. Paquet, A. A. Volmer, E. M. Carreira, *Chemistry—a European Journal* 2008, 14, 2465.

[20] a) K. C. Nicolaou, R. A. Daines, Y. Ogawa, T. K. Chakraborty, *Journal of the American Chemical Society* 1988, 110, 4696; b) K. C. Nicolaou, R. A. Daines, T. K. Chakraborty, Y. Ogawa, *Journal of the American Chemical Society* 1988, 110, 4685; c) K. C. Nicolaou, R. A. Daines, J. Uenishi, W. S. Li, D. P. Papahatjis, T. K. Chakraborty, *Journal of the American Chemical Society* 1988, 110, 4672.

[21] a) E. P. Gillis, M. D. Burke, *Journal of the American Chemical Society* 2007, 129, 6716; b) K. C. G. Suk Joong Lee, James S. Paek, and Martin D. Burke, *Journal of the American Chemical Society* 2008, 130, 466; c) E. M. Woerly, A. H. Cherney, E. K. Davis, M. D. Burke, *Journal of the American Chemical Society* 2010, 132, 6941; d) S. Fujii, S. Y. Chang, M. D. Burke, *Angewandte Chemie-International Edition* 2011, 50, 7862; e) E. P. Gillis, M. D. Burke, *Aldrichimica Acta* 2009, 42, 17.

[22] Y. Gu, B. B. Snider, *Organic Letters* 2003, 5, 4385.

[23] A. Soriente, M. De Rosa, M. Stanzione, R. Villano, A. Scettri, *Tetrahedron: Asymmetry* 2001, 12, 959.

[24] E. P. Gillis, M. D. Burke, *Journal of the American Chemical Society* 2008, 130, 14084.

We claim:

1. Compound X

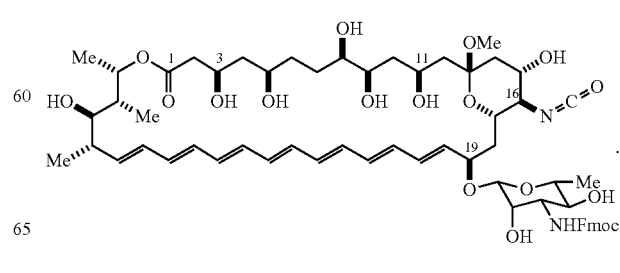

2. Compound 1
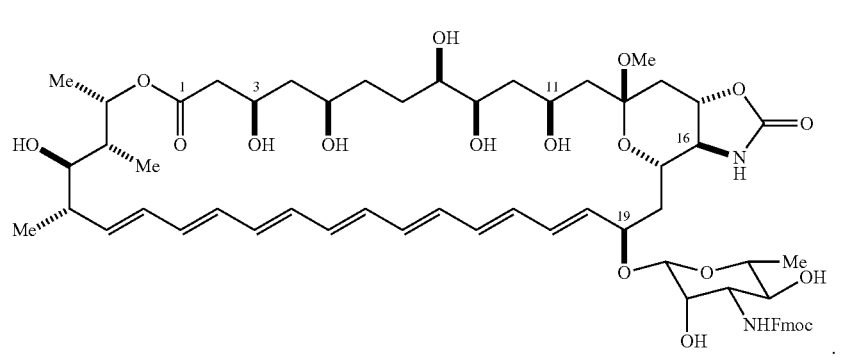
3. A method of making a C16 derivative of amphotericin B according to any one of the six transformations shown in Scheme 2:
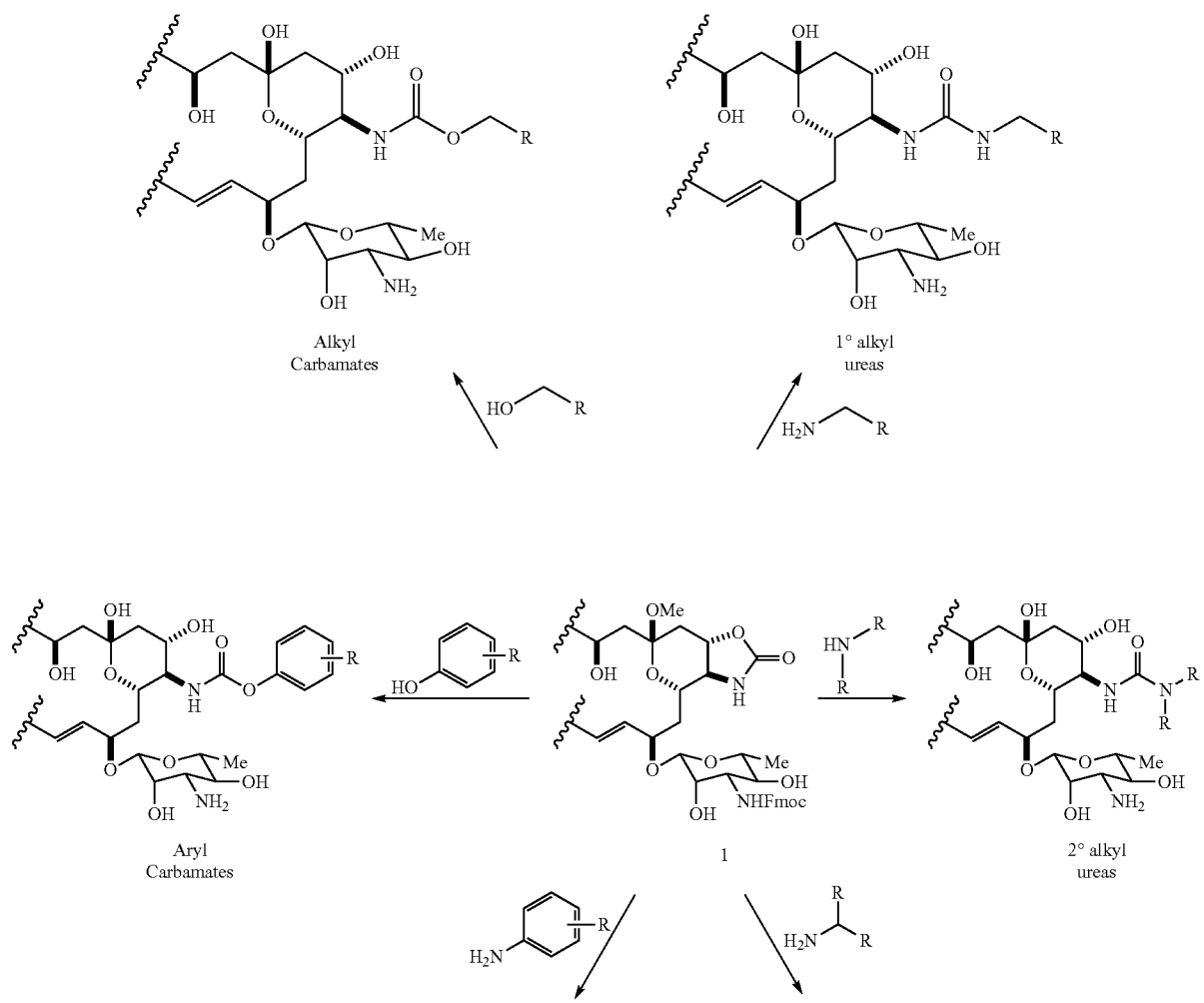

-continued

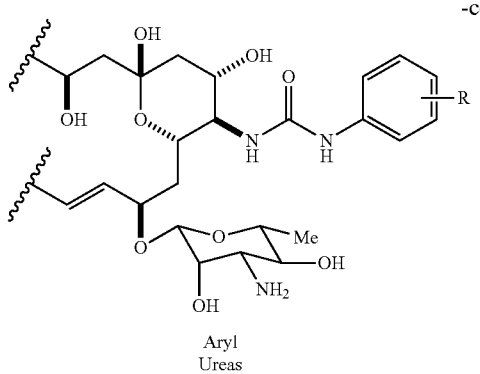

Aryl Ureas

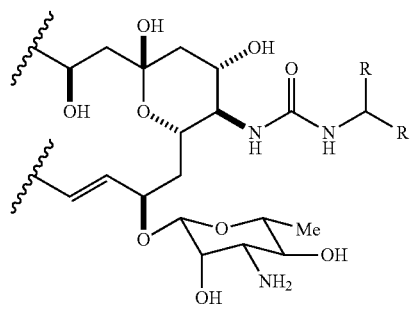

Branched Ureas wherein 1 represents

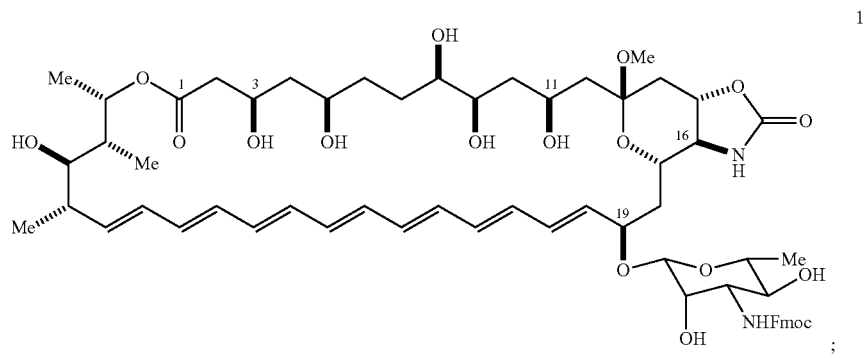

1; and each instance of R is independently selected from the group consisting of hydrogen, halogen, straight- and branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

4. The method of claim 3, wherein the transformation is represented by:

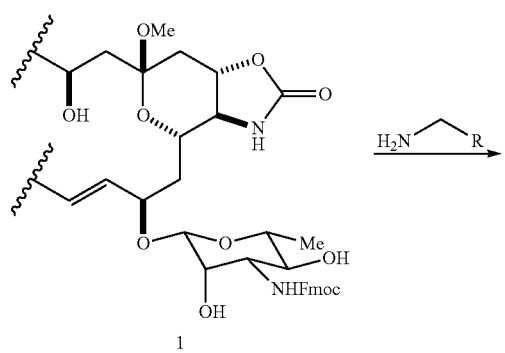

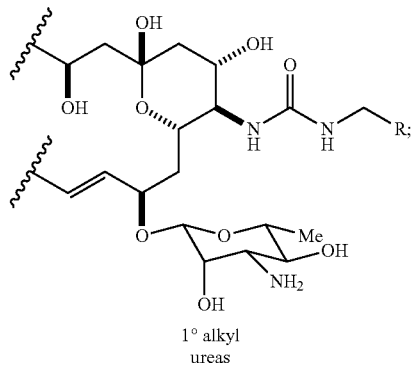

1° alkyl ureas and

R is selected from the group consisting of hydrogen, straight- and branched-chain alkyl, cycloalkyl, cycloalkylalkyl, heterocyclyl, aryl, heteroaryl, aralkyl, heteroaralkyl, carboxyl, amido, aminoalkyl, and alkoxyl.

5. The method of claim 3, wherein the transformation is represented by:

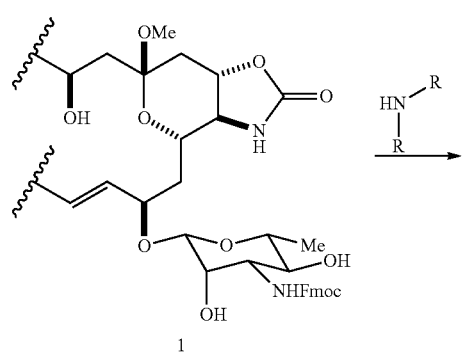

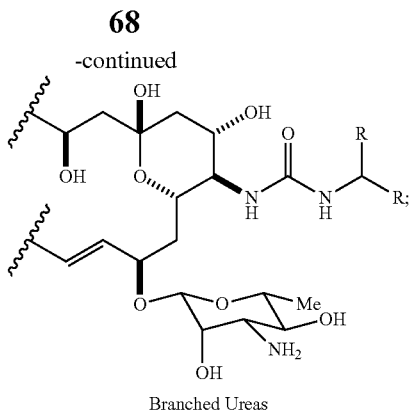

-continued

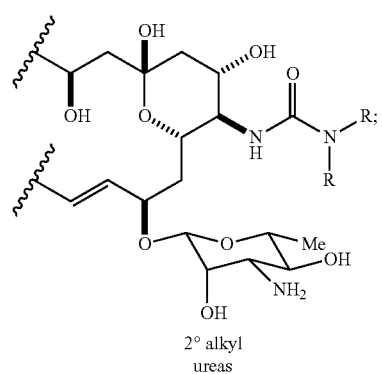

2° alkyl ureas and each instance of R is independently selected from the group consisting of hydrogen, straight- and branched-chain alkyl, cycloalkyl, cycloalkylalkyl, heterocyclyl, aryl, heteroaryl, aralkyl, heteroaralkyl, amino, amido, aminoalkyl, and alkoxyl.

6. The method of claim 3, wherein the transformation is represented by:

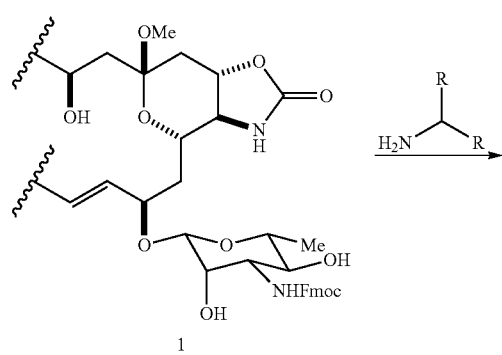

Branched Ureas and each instance of R is independently selected from the group consisting of hydrogen, straight- and branched-chain alkyl, cycloalkyl, cycloalkylalkyl, heterocyclyl, aryl, heteroaryl, aralkyl, heteroaralkyl, carboxyl, amido, aminoalkyl, and alkoxyl.

7. The method of claim 3, wherein the transformation is represented by:

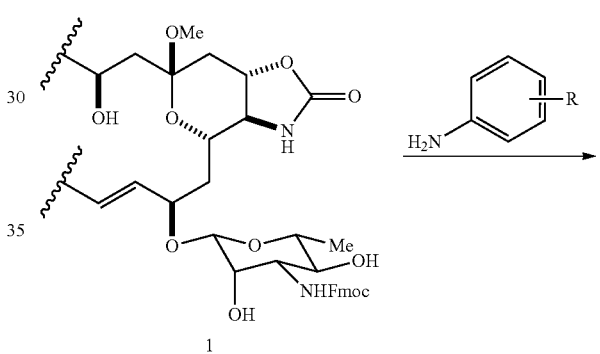

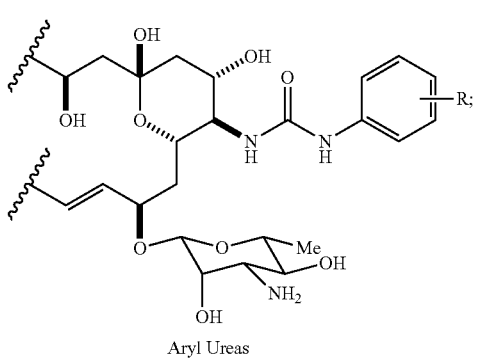

Aryl Ureas and

R is selected from the group consisting of hydrogen, halogen, straight- and branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

8. The method of claim 3, wherein the transformation is represented by:

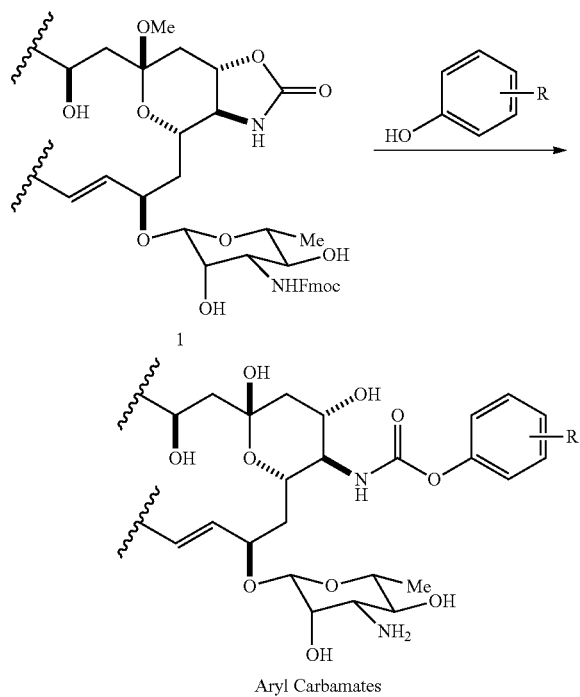

Aryl Carbamates

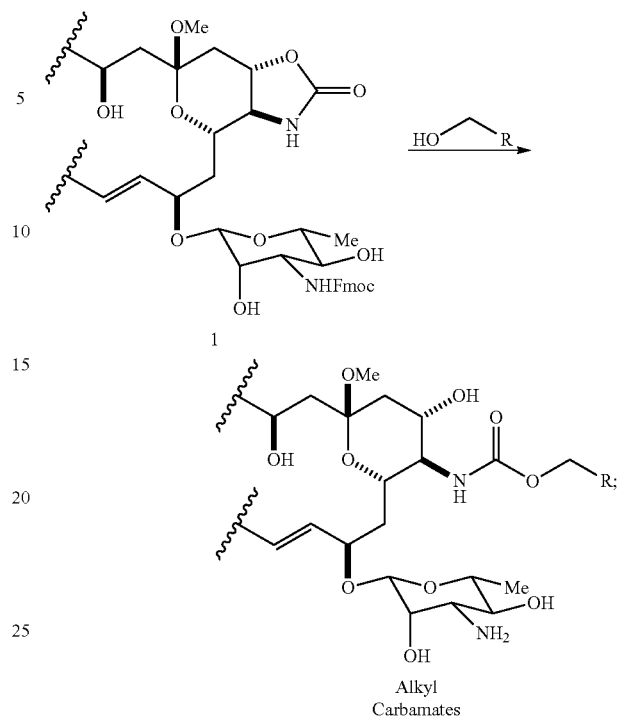

Alkyl Carbamates and

R is selected from the group consisting of hydrogen, halogen, straight- and branched-chain alkyl, cycloalkyl, cycloalkylalkyl, heterocyclyl, aryl, heteroaryl, aralkyl, heteroaralkyl, hydroxyl, sulfhydryl, carboxyl, amino, amido, azido, nitro, cyano, aminoalkyl, and alkoxyl.

9. The method of claim 3, wherein the transformation is represented by:

and

R is selected from the group consisting of hydrogen, straight- and branched-chain alkyl, cycloalkyl, cycloalkylalkyl, heterocyclyl, aryl, heteroaryl, aralkyl, heteroaralkyl, carboxyl, amido, aminoalkyl, and alkoxyl.

\* \* \* \* \*